(12) United States Patent
Guo et al.

(10) Patent No.: US 11,726,474 B2
(45) Date of Patent: Aug. 15, 2023

(54) VEHICLE PATH-PLANNER MONITOR AND CONTROLLER

(71) Applicant: NIO Technology (Anhui) Co., Ltd., Hefei (CN)

(72) Inventors: Bo Guo, San Jose, CA (US); Xiaodong Liu, San Jose, CA (US)

(73) Assignee: NIO TECHNOLOGY (ANHUI) CO., LTD., Hefei (CN)

( * ) Notice: Subject to any disclaimer, the term of this patent is extended or adjusted under 35 U.S.C. 154(b) by 400 days.

(21) Appl. No.: 16/826,873

(22) Filed: Mar. 23, 2020

(65) Prior Publication Data

US 2020/0225661 A1    Jul. 16, 2020

Related U.S. Application Data

(63) Continuation of application No. 15/786,373, filed on Oct. 17, 2017, now Pat. No. 10,635,109.

(51) Int. Cl.
  G05D 1/00 (2006.01)
  B60W 50/14 (2020.01)
  (Continued)

(52) U.S. Cl.
  CPC ......... G05D 1/0088 (2013.01); A61B 5/6893 (2013.01); B60K 28/02 (2013.01);
  (Continued)

(58) Field of Classification Search
  CPC .. G05D 1/0088; G05D 1/0061; A61B 5/6893; A61B 5/02; B60W 40/08; B60W 10/20; B60W 50/02; B60W 50/14
  (Continued)

(56) References Cited

U.S. PATENT DOCUMENTS

| 4,361,202 A | 11/1982 | Minovitch |
| 4,476,954 A | 10/1984 | Johnson et al. |

(Continued)

FOREIGN PATENT DOCUMENTS

| CN | 1417755 | 5/2003 |
| CN | 1847817 | 10/2006 |

(Continued)

OTHER PUBLICATIONS

Final Action for U.S. Appl. No. 15/848,851, dated Jun. 10, 2020, 19 pages.

(Continued)

*Primary Examiner* — Yazan A Soofi
(74) *Attorney, Agent, or Firm* — Sheridan Ross, PC

(57) ABSTRACT

Systems of an autonomous vehicle and the operations thereof are provided. Autonomous vehicles may rely on data inputs, processes, and output commands. Errors due to translation errors, failed or faulty equipment, connections, and other components may cause a dynamic vehicle path to approach a dynamic safe zone or vice versa. If so, a warning message may be sent and processed by the motion control system, when the vehicle is responding to commands correctly, or actuator control, when the vehicle is not responding to commands correctly. Should a safe zone be redrawn to exclude the vehicle's path, a failure message is sent to the appropriate system for mitigation.

20 Claims, 17 Drawing Sheets

(51) Int. Cl.
  *B60W 10/20* (2006.01)
  *B60W 40/08* (2012.01)
  *B60W 50/02* (2012.01)
  *B60K 28/02* (2006.01)
  *A61B 5/00* (2006.01)
  *A61B 5/02* (2006.01)

(52) U.S. Cl.
  CPC .............. *B60W 10/20* (2013.01); *B60W 40/08* (2013.01); *B60W 50/02* (2013.01); *B60W 50/14* (2013.01); *G05D 1/0061* (2013.01); *A61B 5/02* (2013.01)

(58) Field of Classification Search
  USPC .......................................................... 701/23
  See application file for complete search history.

(56) References Cited

U.S. PATENT DOCUMENTS

| | | |
|---|---|---|
| 4,754,255 A | 6/1988 | Sanders et al. |
| 4,875,391 A | 10/1989 | Leising et al. |
| 5,035,302 A | 7/1991 | Thangavelu |
| 5,136,498 A | 8/1992 | McLaughlin et al. |
| 5,204,817 A | 4/1993 | Yoshida |
| 5,363,306 A | 11/1994 | Kuwahara et al. |
| 5,508,689 A | 4/1996 | Rado et al. |
| 5,521,815 A | 5/1996 | Rose |
| 5,529,138 A | 6/1996 | Shaw et al. |
| 5,531,122 A | 7/1996 | Chatham et al. |
| 5,572,450 A | 11/1996 | Worthy |
| 5,610,821 A | 3/1997 | Gazis et al. |
| 5,648,769 A | 7/1997 | Sato et al. |
| 5,710,702 A | 1/1998 | Hayashi et al. |
| 5,794,164 A | 8/1998 | Beckert et al. |
| 5,797,134 A | 8/1998 | McMillan et al. |
| 5,812,067 A | 9/1998 | Bergholz et al. |
| 5,825,283 A | 10/1998 | Camhi |
| 5,838,251 A | 11/1998 | Brinkmeyer et al. |
| 5,847,661 A | 12/1998 | Ricci |
| 5,890,080 A | 3/1999 | Coverdill et al. |
| 5,928,294 A | 7/1999 | Zeiinkovsky |
| 5,949,345 A | 9/1999 | Beckert et al. |
| 5,983,161 A | 11/1999 | Lemelson et al. |
| 5,986,575 A | 11/1999 | Jones et al. |
| 6,038,426 A | 3/2000 | Williams, Jr. |
| 6,081,756 A | 6/2000 | Mio et al. |
| D429,684 S | 8/2000 | Johnson |
| 6,128,003 A | 10/2000 | Smith et al. |
| 6,137,425 A | 10/2000 | Oster et al. |
| 6,141,620 A | 10/2000 | Zyburt et al. |
| 6,148,261 A | 11/2000 | Obradovich et al. |
| 6,152,514 A | 11/2000 | McLellen |
| 6,157,321 A | 12/2000 | Ricci |
| 6,198,996 B1 | 3/2001 | Berstis |
| 6,199,001 B1 | 3/2001 | Ohta et al. |
| 6,202,008 B1 | 3/2001 | Beckert et al. |
| 6,252,544 B1 | 6/2001 | Hoffberg |
| 6,253,161 B1 | 6/2001 | Arias-Estrada |
| 6,267,428 B1 | 7/2001 | Baidas et al. |
| 6,302,438 B1 | 10/2001 | Stopper, Jr. et al. |
| 6,310,542 B1 | 10/2001 | Gehlot |
| 6,317,058 B1 | 11/2001 | Lemelson et al. |
| 6,339,826 B2 | 1/2002 | Hayes, Jr. et al. |
| 6,356,838 B1 | 3/2002 | Paul |
| 6,388,579 B1 | 5/2002 | Adcox et al. |
| 6,393,137 B1 | 5/2002 | Chen et al. |
| 6,480,224 B1 | 11/2002 | Brown |
| 6,480,762 B1 | 11/2002 | Uchikubo et al. |
| 6,502,022 B1 | 12/2002 | Chastain et al. |
| 6,519,519 B1 | 2/2003 | Stopczynski |
| 6,557,752 B1 | 5/2003 | Yacoob |
| 6,563,910 B2 | 5/2003 | Menard et al. |
| 6,587,739 B1 | 7/2003 | Abrams et al. |
| 6,598,227 B1 | 7/2003 | Berry et al. |
| 6,607,212 B1 | 8/2003 | Reimer et al. |
| 6,617,981 B2 | 9/2003 | Basinger |
| 6,633,800 B1 | 10/2003 | Ward et al. |
| 6,662,077 B2 | 12/2003 | Haag |
| 6,675,081 B2 | 1/2004 | Shuman et al. |
| 6,678,747 B2 | 1/2004 | Goossen et al. |
| 6,681,176 B2 | 1/2004 | Funk et al. |
| 6,690,260 B1 | 2/2004 | Ashihara |
| 6,690,940 B1 | 2/2004 | Brown et al. |
| 6,724,920 B1 | 4/2004 | Berenz et al. |
| 6,754,580 B1 | 6/2004 | Ask et al. |
| 6,757,593 B2 | 6/2004 | Mori et al. |
| 6,762,684 B1 | 7/2004 | Camhi |
| 6,765,495 B1 | 7/2004 | Dunning et al. |
| 6,778,888 B2 | 8/2004 | Cataldo et al. |
| 6,782,240 B1 | 8/2004 | Tabe |
| 6,785,531 B2 | 8/2004 | Lepley et al. |
| 6,816,783 B2 | 11/2004 | Hashima et al. |
| 6,820,259 B1 | 11/2004 | Kawamata et al. |
| 6,944,533 B2 | 9/2005 | Obradovich et al. |
| 6,950,022 B2 | 9/2005 | Breed |
| 6,958,707 B1 | 10/2005 | Siegel |
| 6,992,580 B2 | 1/2006 | Kotzin et al. |
| 7,019,641 B1 | 3/2006 | Lakshmanan et al. |
| 7,020,544 B2 | 3/2006 | Shinada et al. |
| 7,021,691 B1 | 4/2006 | Schmidt et al. |
| 7,042,345 B2 | 5/2006 | Ellis |
| 7,047,129 B2 | 5/2006 | Uotani |
| 7,058,898 B2 | 6/2006 | McWalter et al. |
| 7,096,431 B2 | 8/2006 | Tambata et al. |
| 7,142,696 B1 | 11/2006 | Engelsberg et al. |
| 7,164,117 B2 | 1/2007 | Breed et al. |
| 7,187,947 B1 | 3/2007 | White et al. |
| 7,203,598 B1 | 4/2007 | Whitsell |
| 7,233,861 B2 | 6/2007 | Van Buer et al. |
| 7,239,960 B2 | 7/2007 | Yokota et al. |
| 7,277,454 B2 | 10/2007 | Mocek et al. |
| 7,284,769 B2 | 10/2007 | Breed |
| 7,289,645 B2 | 10/2007 | Yamamoto et al. |
| 7,295,921 B2 | 11/2007 | Spencer et al. |
| 7,313,547 B2 | 12/2007 | Mocek et al. |
| 7,333,012 B1 | 2/2008 | Nguyen |
| 7,343,148 B1 | 3/2008 | O'Neil |
| 7,386,376 B2 | 6/2008 | Basir et al. |
| 7,386,799 B1 | 6/2008 | Clanton et al. |
| 7,432,829 B2 | 10/2008 | Poltorak |
| 7,474,264 B2 | 1/2009 | Bolduc et al. |
| 7,493,140 B2 | 2/2009 | Michmerhuizen et al. |
| 7,526,539 B1 | 4/2009 | Hsu |
| 7,548,815 B2 | 6/2009 | Watkins et al. |
| 7,566,083 B2 | 7/2009 | Vitito |
| 7,606,660 B2 | 10/2009 | Diaz et al. |
| 7,606,867 B1 | 10/2009 | Singhal et al. |
| 7,643,913 B2 | 1/2010 | Taki et al. |
| 7,650,234 B2 | 1/2010 | Obradovich et al. |
| 7,671,764 B2 | 3/2010 | Uyeki et al. |
| 7,680,596 B2 | 3/2010 | Uyeki et al. |
| 7,683,771 B1 | 3/2010 | Loeb |
| 7,711,468 B1 | 5/2010 | Levy |
| 7,734,315 B2 | 6/2010 | Rathus et al. |
| 7,748,021 B2 | 6/2010 | Obradovich et al. |
| RE41,449 E | 7/2010 | Krahnstoever et al. |
| 7,791,499 B2 | 9/2010 | Mohan et al. |
| 7,796,190 B2 | 9/2010 | Basso et al. |
| 7,802,832 B2 | 9/2010 | Carnevali |
| 7,821,421 B2 | 10/2010 | Tamir et al. |
| 7,832,762 B2 | 11/2010 | Breed |
| 7,864,073 B2 | 1/2011 | Lee et al. |
| 7,872,591 B2 | 1/2011 | Kane et al. |
| 7,873,471 B2 | 1/2011 | Gieseke |
| 7,881,703 B2 | 2/2011 | Roundtree et al. |
| 7,891,004 B1 | 2/2011 | Gelvin et al. |
| 7,891,719 B2 | 2/2011 | Carnevali |
| 7,894,951 B2 | 2/2011 | Norris et al. |
| 7,899,610 B2 | 3/2011 | McClellan |
| 7,966,678 B2 | 6/2011 | Ten Eyck et al. |
| 7,969,290 B2 | 6/2011 | Waeller et al. |
| 7,969,324 B2 | 6/2011 | Chevion et al. |
| 8,060,631 B2 | 11/2011 | Collart et al. |

(56) References Cited

U.S. PATENT DOCUMENTS

| | | |
|---|---|---|
| 8,064,925 B1 | 11/2011 | Sun et al. |
| 8,066,313 B2 | 11/2011 | Carnevali |
| 8,098,170 B1 | 1/2012 | Szczerba et al. |
| 8,113,564 B2 | 2/2012 | Carnevali |
| 8,131,419 B2 | 3/2012 | Ampunan et al. |
| 8,157,310 B2 | 4/2012 | Carnevali |
| 8,162,368 B2 | 4/2012 | Carnevali |
| 8,175,802 B2 | 5/2012 | Forstall et al. |
| 8,233,919 B2 | 7/2012 | Haag et al. |
| 8,245,609 B1 | 8/2012 | Greenwald et al. |
| 8,306,514 B1 | 11/2012 | Nunally |
| 8,334,847 B2 | 12/2012 | Tomkins |
| 8,346,233 B2 | 1/2013 | Aaron et al. |
| 8,346,432 B2 | 1/2013 | Van Wiemeersch et al. |
| 8,350,721 B2 | 1/2013 | Carr |
| 8,352,282 B2 | 1/2013 | Jensen et al. |
| 8,369,263 B2 | 2/2013 | Dowling et al. |
| 8,391,554 B2 | 3/2013 | Lee et al. |
| 8,417,449 B1 | 4/2013 | Denise |
| 8,428,843 B2 | 4/2013 | Lee et al. |
| 8,432,260 B2 | 4/2013 | Talty et al. |
| 8,442,389 B2 | 5/2013 | Kashima et al. |
| 8,442,758 B1 | 5/2013 | Rovik et al. |
| 8,467,965 B2 | 6/2013 | Chang |
| 8,497,842 B2 | 7/2013 | Tomkins et al. |
| 8,498,809 B2 | 7/2013 | Bill |
| 8,509,982 B2 | 8/2013 | Montemerlo et al. |
| 8,521,410 B2 | 8/2013 | Mizuno et al. |
| 8,527,143 B2 | 9/2013 | Tan |
| 8,527,146 B1 | 9/2013 | Jackson et al. |
| 8,532,574 B2 | 9/2013 | Kirsch |
| 8,543,330 B2 | 9/2013 | Taylor et al. |
| 8,547,340 B2 | 10/2013 | Sizelove et al. |
| 8,548,669 B2 | 10/2013 | Naylor |
| 8,559,183 B1 | 10/2013 | Davis |
| 8,577,600 B1 | 11/2013 | Pierfelice |
| 8,578,279 B2 | 11/2013 | Chen et al. |
| 8,583,292 B2 | 11/2013 | Preston et al. |
| 8,589,073 B2 | 11/2013 | Guha et al. |
| 8,600,611 B2 | 12/2013 | Seize |
| 8,613,385 B1 | 12/2013 | Hulet et al. |
| 8,621,645 B1 | 12/2013 | Spackman |
| 8,624,727 B2 | 1/2014 | Saigh et al. |
| 8,634,980 B1 | 1/2014 | Urmson et al. |
| 8,634,984 B2 | 1/2014 | Sumizawa |
| 8,644,165 B2 | 2/2014 | Saarimaki et al. |
| 8,660,735 B2 | 2/2014 | Tengler et al. |
| 8,671,068 B2 | 3/2014 | Harber et al. |
| 8,688,372 B2 | 4/2014 | Bhogal et al. |
| 8,698,639 B2 | 4/2014 | Fung et al. |
| 8,705,527 B1 | 4/2014 | Addepalli et al. |
| 8,706,143 B1 | 4/2014 | Elias |
| 8,718,797 B1 | 5/2014 | Addepalli et al. |
| 8,718,910 B2 | 5/2014 | Gueziec |
| 8,725,311 B1 | 5/2014 | Breed |
| 8,730,033 B2 | 5/2014 | Yarnold et al. |
| 8,737,986 B2 | 5/2014 | Rhoads et al. |
| 8,761,673 B2 | 6/2014 | Sakata |
| 8,774,842 B2 | 7/2014 | Jones et al. |
| 8,779,947 B2 | 7/2014 | Tengler et al. |
| 8,782,262 B2 | 7/2014 | Collart et al. |
| 8,793,065 B2 | 7/2014 | Seltzer et al. |
| 8,798,918 B2 | 8/2014 | Onishi et al. |
| 8,805,110 B2 | 8/2014 | Rhoads et al. |
| 8,812,171 B2 | 8/2014 | Filev et al. |
| 8,817,761 B2 | 8/2014 | Gruberman et al. |
| 8,825,031 B2 | 9/2014 | Aaron et al. |
| 8,825,277 B2 | 9/2014 | McClellan et al. |
| 8,825,382 B2 | 9/2014 | Liu |
| 8,826,261 B1 | 9/2014 | Anand Ag et al. |
| 8,838,088 B1 | 9/2014 | Henn et al. |
| 8,862,317 B2 | 10/2014 | Shin et al. |
| 8,972,090 B2 | 3/2015 | Weslati et al. |
| 8,977,408 B1 | 3/2015 | Cazanas et al. |
| 9,043,016 B2 | 5/2015 | Filippov et al. |
| 9,163,952 B2 | 10/2015 | Viola et al. |
| 9,180,783 B1 | 11/2015 | Penilia et al. |
| 9,188,985 B1 | 11/2015 | Hobbs et al. |
| 9,229,905 B1 | 1/2016 | Penilia et al. |
| 9,285,240 B2 | 3/2016 | Yenamandra et al. |
| 9,299,251 B2 | 3/2016 | Scofield et al. |
| 9,360,342 B2 | 6/2016 | Ignatin |
| 9,371,007 B1 | 6/2016 | Penilla et al. |
| 9,488,493 B2 | 11/2016 | MacNeille et al. |
| 9,581,460 B1 | 2/2017 | McNew et al. |
| 9,663,118 B1 | 5/2017 | Palmer et al. |
| 9,714,837 B2 | 7/2017 | North et al. |
| 9,969,404 B2 | 5/2018 | McNew |
| 10,077,056 B1 | 9/2018 | Fields et al. |
| 10,216,190 B2 | 2/2019 | Bostick et al. |
| 10,217,160 B2 | 2/2019 | Penilla et al. |
| 10,234,302 B2 | 3/2019 | Singhal et al. |
| 10,272,793 B2 | 4/2019 | Perry et al. |
| 10,281,296 B2 | 5/2019 | MacNeille et al. |
| 10,286,915 B2 | 5/2019 | Xiao et al. |
| 10,339,621 B2 | 7/2019 | Hirose et al. |
| 10,360,518 B2 | 7/2019 | Hirose et al. |
| 10,410,250 B2 | 9/2019 | Singhal et al. |
| 10,471,829 B2 | 11/2019 | Yellambalase et al. |
| 10,606,274 B2 | 3/2020 | Yalla et al. |
| 10,635,109 B2 | 4/2020 | Guo et al. |
| 2001/0010516 A1 | 8/2001 | Roh et al. |
| 2001/0015888 A1 | 8/2001 | Shaler et al. |
| 2002/0009978 A1 | 1/2002 | Dukach et al. |
| 2002/0023010 A1 | 2/2002 | Rittmaster et al. |
| 2002/0026278 A1 | 2/2002 | Feldman et al. |
| 2002/0045484 A1 | 4/2002 | Eck et al. |
| 2002/0065046 A1 | 5/2002 | Mankins et al. |
| 2002/0077985 A1 | 6/2002 | Kobata et al. |
| 2002/0095249 A1 | 7/2002 | Lang |
| 2002/0097145 A1 | 7/2002 | Tumey et al. |
| 2002/0103622 A1 | 8/2002 | Burge |
| 2002/0105968 A1 | 8/2002 | Pruzan et al. |
| 2002/0126876 A1 | 9/2002 | Paul et al. |
| 2002/0128774 A1 | 9/2002 | Takezaki et al. |
| 2002/0143461 A1 | 10/2002 | Burns et al. |
| 2002/0143643 A1 | 10/2002 | Catan |
| 2002/0152010 A1 | 10/2002 | Colmenarez et al. |
| 2002/0154217 A1 | 10/2002 | Ikeda |
| 2002/0169531 A1 | 11/2002 | Kawazoe et al. |
| 2002/0169551 A1 | 11/2002 | Inoue et al. |
| 2002/0174021 A1 | 11/2002 | Chu et al. |
| 2003/0004624 A1 | 1/2003 | Wilson et al. |
| 2003/0007227 A1 | 1/2003 | Ogino |
| 2003/0055557 A1 | 3/2003 | Dutta et al. |
| 2003/0060937 A1 | 3/2003 | Shinada et al. |
| 2003/0060977 A1 | 3/2003 | Jijina et al. |
| 2003/0065432 A1 | 4/2003 | Shuman et al. |
| 2003/0101451 A1 | 5/2003 | Bentolila et al. |
| 2003/0109972 A1 | 6/2003 | Tak |
| 2003/0125846 A1 | 7/2003 | Yu et al. |
| 2003/0132666 A1 | 7/2003 | Bond et al. |
| 2003/0149530 A1 | 8/2003 | Stopczynski |
| 2003/0158638 A1 | 8/2003 | Yakes et al. |
| 2003/0182435 A1 | 9/2003 | Redlich et al. |
| 2003/0202683 A1 | 10/2003 | Ma et al. |
| 2003/0204290 A1 | 10/2003 | Sadler et al. |
| 2003/0209893 A1 | 11/2003 | Breed et al. |
| 2003/0230443 A1 | 12/2003 | Cramer et al. |
| 2004/0017292 A1 | 1/2004 | Reese et al. |
| 2004/0024502 A1 | 2/2004 | Squires et al. |
| 2004/0036622 A1 | 2/2004 | Dukach et al. |
| 2004/0039500 A1 | 2/2004 | Amendola et al. |
| 2004/0039504 A1 | 2/2004 | Coffee et al. |
| 2004/0068364 A1 | 4/2004 | Zhao et al. |
| 2004/0070920 A1 | 4/2004 | Flueli |
| 2004/0093155 A1 | 5/2004 | Simonds et al. |
| 2004/0117494 A1 | 6/2004 | Mitchell et al. |
| 2004/0128062 A1 | 7/2004 | Ogino et al. |
| 2004/0153356 A1 | 8/2004 | Lockwood et al. |
| 2004/0162019 A1 | 8/2004 | Horita et al. |
| 2004/0180653 A1 | 9/2004 | Royalty |
| 2004/0182574 A1 | 9/2004 | Adnan et al. |
| 2004/0193347 A1 | 9/2004 | Harumoto et al. |

(56) References Cited

U.S. PATENT DOCUMENTS

| | | |
|---|---|---|
| 2004/0203974 A1 | 10/2004 | Seibel |
| 2004/0204837 A1 | 10/2004 | Singleton |
| 2004/0209594 A1 | 10/2004 | Naboulsi |
| 2004/0217850 A1 | 11/2004 | Perttunen et al. |
| 2004/0225557 A1 | 11/2004 | Phelan et al. |
| 2004/0249568 A1 | 12/2004 | Endo et al. |
| 2004/0255123 A1 | 12/2004 | Noyama et al. |
| 2004/0257208 A1 | 12/2004 | Huang et al. |
| 2004/0260470 A1 | 12/2004 | Rast |
| 2005/0012599 A1 | 1/2005 | DeMatteo |
| 2005/0031100 A1 | 2/2005 | Iggulden et al. |
| 2005/0038598 A1 | 2/2005 | Oesterling et al. |
| 2005/0042999 A1 | 2/2005 | Rappaport |
| 2005/0065678 A1 | 3/2005 | Smith et al. |
| 2005/0065711 A1 | 3/2005 | Dahlgren et al. |
| 2005/0086051 A1 | 4/2005 | Brulle-Drews |
| 2005/0092542 A1 | 5/2005 | Turner |
| 2005/0093717 A1 | 5/2005 | Lilja |
| 2005/0097541 A1 | 5/2005 | Holland |
| 2005/0114864 A1 | 5/2005 | Race |
| 2005/0122235 A1 | 6/2005 | Teffer et al. |
| 2005/0124211 A1 | 6/2005 | Diessner et al. |
| 2005/0130744 A1 | 6/2005 | Eck et al. |
| 2005/0144156 A1 | 6/2005 | Barber |
| 2005/0149752 A1 | 7/2005 | Johnson et al. |
| 2005/0153760 A1 | 7/2005 | Varley |
| 2005/0159853 A1 | 7/2005 | Takahashi et al. |
| 2005/0159892 A1 | 7/2005 | Chung |
| 2005/0192727 A1 | 9/2005 | Shostak et al. |
| 2005/0197748 A1 | 9/2005 | Holst et al. |
| 2005/0197767 A1 | 9/2005 | Nortrup |
| 2005/0234614 A1* | 10/2005 | Sakurai .......... B62D 5/049 701/43 |
| 2005/0234679 A1 | 10/2005 | Karlsson |
| 2005/0251324 A1 | 11/2005 | Wiener et al. |
| 2005/0261815 A1 | 11/2005 | Cowelchuk et al. |
| 2005/0278093 A1 | 12/2005 | Kameyama |
| 2005/0283284 A1 | 12/2005 | Grenier et al. |
| 2006/0015819 A1 | 1/2006 | Hawkins et al. |
| 2006/0036358 A1 | 2/2006 | Hale et al. |
| 2006/0044119 A1 | 3/2006 | Egelhaaf |
| 2006/0047386 A1 | 3/2006 | Kanevsky et al. |
| 2006/0058948 A1 | 3/2006 | Blass et al. |
| 2006/0059229 A1 | 3/2006 | Bain et al. |
| 2006/0125631 A1 | 6/2006 | Sharony |
| 2006/0130033 A1 | 6/2006 | Stoffels et al. |
| 2006/0142933 A1 | 6/2006 | Feng |
| 2006/0173841 A1 | 8/2006 | Bill |
| 2006/0175403 A1 | 8/2006 | McConnell et al. |
| 2006/0184319 A1 | 8/2006 | Seick et al. |
| 2006/0212909 A1 | 9/2006 | Girard et al. |
| 2006/0217864 A1 | 9/2006 | Johnson et al. |
| 2006/0241836 A1 | 10/2006 | Kachouh et al. |
| 2006/0243056 A1 | 11/2006 | Sundermeyer et al. |
| 2006/0250272 A1 | 11/2006 | Puamau |
| 2006/0253307 A1 | 11/2006 | Warren et al. |
| 2006/0259210 A1 | 11/2006 | Tanaka et al. |
| 2006/0274829 A1 | 12/2006 | Siemens et al. |
| 2006/0282204 A1 | 12/2006 | Breed |
| 2006/0287807 A1 | 12/2006 | Teffer |
| 2006/0287865 A1 | 12/2006 | Cross et al. |
| 2006/0288382 A1 | 12/2006 | Vitito |
| 2006/0290516 A1 | 12/2006 | Muehlsteff et al. |
| 2006/0293856 A1 | 12/2006 | Foessel et al. |
| 2007/0001831 A1 | 1/2007 | Raz et al. |
| 2007/0002032 A1 | 1/2007 | Powers et al. |
| 2007/0010942 A1 | 1/2007 | Bill |
| 2007/0015485 A1 | 1/2007 | DeBiasio et al. |
| 2007/0028370 A1 | 2/2007 | Seng |
| 2007/0032225 A1 | 2/2007 | Konicek et al. |
| 2007/0057781 A1 | 3/2007 | Breed |
| 2007/0061057 A1 | 3/2007 | Huang et al. |
| 2007/0067614 A1 | 3/2007 | Berry et al. |
| 2007/0069880 A1 | 3/2007 | Best et al. |
| 2007/0083298 A1 | 4/2007 | Pierce et al. |
| 2007/0088488 A1 | 4/2007 | Reeves et al. |
| 2007/0103328 A1 | 5/2007 | Lakshmanan et al. |
| 2007/0115101 A1 | 5/2007 | Creekbaum et al. |
| 2007/0118301 A1 | 5/2007 | Andarawis et al. |
| 2007/0120697 A1 | 5/2007 | Ayoub et al. |
| 2007/0135995 A1 | 6/2007 | Kikuchi et al. |
| 2007/0156317 A1 | 7/2007 | Breed |
| 2007/0182625 A1 | 8/2007 | Kerai et al. |
| 2007/0182816 A1 | 8/2007 | Fox |
| 2007/0185969 A1 | 8/2007 | Davis |
| 2007/0192486 A1 | 8/2007 | Wilson et al. |
| 2007/0194902 A1 | 8/2007 | Blanco et al. |
| 2007/0194944 A1 | 8/2007 | Galera et al. |
| 2007/0195997 A1 | 8/2007 | Paul et al. |
| 2007/0200663 A1 | 8/2007 | White et al. |
| 2007/0208860 A1 | 9/2007 | Zellner et al. |
| 2007/0213090 A1 | 9/2007 | Holmberg |
| 2007/0228826 A1 | 10/2007 | Jordan et al. |
| 2007/0233341 A1 | 10/2007 | Logsdon |
| 2007/0250228 A1 | 10/2007 | Reddy et al. |
| 2007/0257815 A1 | 11/2007 | Gunderson et al. |
| 2007/0276596 A1 | 11/2007 | Solomon et al. |
| 2007/0280505 A1 | 12/2007 | Breed |
| 2008/0005974 A1 | 1/2008 | Delgado Vazquez et al. |
| 2008/0023253 A1 | 1/2008 | Prost-Fin et al. |
| 2008/0027337 A1 | 1/2008 | Dugan et al. |
| 2008/0033635 A1 | 2/2008 | Obradovich et al. |
| 2008/0042824 A1 | 2/2008 | Kates |
| 2008/0051957 A1 | 2/2008 | Breed et al. |
| 2008/0052627 A1 | 2/2008 | Oguchi |
| 2008/0071465 A1 | 3/2008 | Chapman et al. |
| 2008/0082237 A1 | 4/2008 | Breed |
| 2008/0086455 A1 | 4/2008 | Meisels et al. |
| 2008/0090522 A1 | 4/2008 | Oyama |
| 2008/0104227 A1 | 5/2008 | Birnie et al. |
| 2008/0119994 A1 | 5/2008 | Kameyama |
| 2008/0129475 A1 | 6/2008 | Breed et al. |
| 2008/0143085 A1 | 6/2008 | Breed et al. |
| 2008/0147280 A1 | 6/2008 | Breed |
| 2008/0148374 A1 | 6/2008 | Spaur et al. |
| 2008/0154712 A1 | 6/2008 | Wellman |
| 2008/0154957 A1 | 6/2008 | Taylor et al. |
| 2008/0161986 A1 | 7/2008 | Breed |
| 2008/0164985 A1 | 7/2008 | Iketani et al. |
| 2008/0169940 A1 | 7/2008 | Lee et al. |
| 2008/0174451 A1 | 7/2008 | Harrington et al. |
| 2008/0212215 A1 | 9/2008 | Schofield et al. |
| 2008/0216067 A1 | 9/2008 | Villing |
| 2008/0228358 A1 | 9/2008 | Wang et al. |
| 2008/0234919 A1 | 9/2008 | Ritter et al. |
| 2008/0252487 A1 | 10/2008 | McClellan et al. |
| 2008/0253613 A1 | 10/2008 | Jones et al. |
| 2008/0255721 A1 | 10/2008 | Yamada |
| 2008/0255722 A1 | 10/2008 | McClellan et al. |
| 2008/0269958 A1 | 10/2008 | Filev et al. |
| 2008/0281508 A1 | 11/2008 | Fu |
| 2008/0300778 A1 | 12/2008 | Kuznetsov |
| 2008/0305780 A1 | 12/2008 | Williams et al. |
| 2008/0319602 A1 | 12/2008 | McClellan et al. |
| 2009/0006525 A1 | 1/2009 | Moore |
| 2009/0024251 A1 | 1/2009 | Myeong et al. |
| 2009/0024419 A1 | 1/2009 | McClellan et al. |
| 2009/0037719 A1 | 2/2009 | Sakthikumar et al. |
| 2009/0040026 A1 | 2/2009 | Tanaka |
| 2009/0055178 A1 | 2/2009 | Coon |
| 2009/0082951 A1 | 3/2009 | Graessley |
| 2009/0099720 A1 | 4/2009 | Elgali |
| 2009/0112393 A1 | 4/2009 | Maten et al. |
| 2009/0112452 A1 | 4/2009 | Buck et al. |
| 2009/0119657 A1 | 5/2009 | Link, II |
| 2009/0125174 A1 | 5/2009 | Delean |
| 2009/0132294 A1 | 5/2009 | Haines |
| 2009/0138336 A1 | 5/2009 | Ashley et al. |
| 2009/0144622 A1 | 6/2009 | Evans et al. |
| 2009/0157312 A1 | 6/2009 | Black et al. |
| 2009/0158200 A1 | 6/2009 | Palahnuk et al. |
| 2009/0180668 A1 | 7/2009 | Jones et al. |
| 2009/0189373 A1 | 7/2009 | Schramm et al. |
| 2009/0189979 A1 | 7/2009 | Smyth |

(56) References Cited

U.S. PATENT DOCUMENTS

| | | |
|---|---|---|
| 2009/0195370 A1 | 8/2009 | Huffman et al. |
| 2009/0210257 A1 | 8/2009 | Chalfant et al. |
| 2009/0216935 A1 | 8/2009 | Flick |
| 2009/0222200 A1 | 9/2009 | Link et al. |
| 2009/0224931 A1 | 9/2009 | Dietz et al. |
| 2009/0224942 A1 | 9/2009 | Goudy et al. |
| 2009/0234578 A1 | 9/2009 | Newby et al. |
| 2009/0241883 A1 | 10/2009 | Nagoshi et al. |
| 2009/0254446 A1 | 10/2009 | Chernyak |
| 2009/0264849 A1 | 10/2009 | La Croix |
| 2009/0275321 A1 | 11/2009 | Crowe |
| 2009/0278750 A1 | 11/2009 | Man et al. |
| 2009/0278915 A1 | 11/2009 | Kramer et al. |
| 2009/0279839 A1 | 11/2009 | Nakamura et al. |
| 2009/0284359 A1 | 11/2009 | Huang et al. |
| 2009/0287405 A1 | 11/2009 | Liu et al. |
| 2009/0299572 A1 | 12/2009 | Fujikawa et al. |
| 2009/0312998 A1 | 12/2009 | Berckmans et al. |
| 2009/0319181 A1 | 12/2009 | Khosravy et al. |
| 2010/0004856 A1 | 1/2010 | Kobori et al. |
| 2010/0008053 A1 | 1/2010 | Osternack et al. |
| 2010/0023204 A1 | 1/2010 | Basir et al. |
| 2010/0035620 A1 | 2/2010 | Naden et al. |
| 2010/0036560 A1 | 2/2010 | Wright et al. |
| 2010/0036606 A1 | 2/2010 | Jones |
| 2010/0042498 A1 | 2/2010 | Schalk |
| 2010/0049397 A1 | 2/2010 | Liu et al. |
| 2010/0052945 A1 | 3/2010 | Breed |
| 2010/0057337 A1 | 3/2010 | Fuchs |
| 2010/0066498 A1 | 3/2010 | Fenton |
| 2010/0069115 A1 | 3/2010 | Liu |
| 2010/0070338 A1 | 3/2010 | Siotia et al. |
| 2010/0077094 A1 | 3/2010 | Howarter et al. |
| 2010/0087987 A1 | 4/2010 | Huang et al. |
| 2010/0090817 A1 | 4/2010 | Yamaguchi et al. |
| 2010/0097178 A1 | 4/2010 | Pisz et al. |
| 2010/0097239 A1 | 4/2010 | Campbell et al. |
| 2010/0097458 A1 | 4/2010 | Zhang et al. |
| 2010/0106344 A1 | 4/2010 | Edwards et al. |
| 2010/0106418 A1 | 4/2010 | Kindo et al. |
| 2010/0118025 A1 | 5/2010 | Smith et al. |
| 2010/0121570 A1 | 5/2010 | Tokue et al. |
| 2010/0121645 A1 | 5/2010 | Seitz et al. |
| 2010/0125387 A1 | 5/2010 | Sehyun et al. |
| 2010/0125405 A1 | 5/2010 | Chae et al. |
| 2010/0125811 A1 | 5/2010 | Moore et al. |
| 2010/0127847 A1 | 5/2010 | Evans et al. |
| 2010/0131300 A1 | 5/2010 | Collopy et al. |
| 2010/0134302 A1 | 6/2010 | Ahn et al. |
| 2010/0134958 A1 | 6/2010 | Disaverio et al. |
| 2010/0136944 A1 | 6/2010 | Taylor et al. |
| 2010/0137037 A1 | 6/2010 | Basir |
| 2010/0144284 A1 | 6/2010 | Chutorash et al. |
| 2010/0145700 A1 | 6/2010 | Kennewick et al. |
| 2010/0145987 A1 | 6/2010 | Harper et al. |
| 2010/0152976 A1 | 6/2010 | White et al. |
| 2010/0169432 A1 | 7/2010 | Santori et al. |
| 2010/0174474 A1 | 7/2010 | Nagase |
| 2010/0179712 A1 | 7/2010 | Pepitone et al. |
| 2010/0185341 A1 | 7/2010 | Wilson et al. |
| 2010/0188831 A1 | 7/2010 | Oriel |
| 2010/0197359 A1 | 8/2010 | Harris |
| 2010/0202346 A1 | 8/2010 | Sitzes et al. |
| 2010/0211259 A1 | 8/2010 | McClellan |
| 2010/0211282 A1 | 8/2010 | Nakata et al. |
| 2010/0211300 A1 | 8/2010 | Jaffe et al. |
| 2010/0211304 A1 | 8/2010 | Hwang et al. |
| 2010/0211441 A1 | 8/2010 | Sprigg et al. |
| 2010/0217458 A1 | 8/2010 | Schweiger et al. |
| 2010/0222939 A1 | 9/2010 | Namburu et al. |
| 2010/0228404 A1 | 9/2010 | Link et al. |
| 2010/0234071 A1 | 9/2010 | Shabtay et al. |
| 2010/0235042 A1 | 9/2010 | Ying |
| 2010/0235744 A1 | 9/2010 | Schultz |
| 2010/0235891 A1 | 9/2010 | Oglesbee et al. |
| 2010/0250071 A1 | 9/2010 | Pala et al. |
| 2010/0253493 A1 | 10/2010 | Szczerba et al. |
| 2010/0256836 A1 | 10/2010 | Mudalige |
| 2010/0265104 A1 | 10/2010 | Zlojutro |
| 2010/0268426 A1 | 10/2010 | Pathak et al. |
| 2010/0274410 A1 | 10/2010 | Tsien et al. |
| 2010/0280751 A1 | 11/2010 | Breed |
| 2010/0287303 A1 | 11/2010 | Smith et al. |
| 2010/0289632 A1 | 11/2010 | Seder et al. |
| 2010/0289643 A1 | 11/2010 | Trundle et al. |
| 2010/0291427 A1 | 11/2010 | Zhou |
| 2010/0295676 A1 | 11/2010 | Khachaturov et al. |
| 2010/0304640 A1 | 12/2010 | Sofman et al. |
| 2010/0305807 A1 | 12/2010 | Basir et al. |
| 2010/0306080 A1 | 12/2010 | Trandal et al. |
| 2010/0306309 A1 | 12/2010 | Santori et al. |
| 2010/0306435 A1 | 12/2010 | Nigoghosian et al. |
| 2010/0315218 A1 | 12/2010 | Cades et al. |
| 2010/0321151 A1 | 12/2010 | Matsuura et al. |
| 2010/0325626 A1 | 12/2010 | Greschler et al. |
| 2010/0332130 A1 | 12/2010 | Shimizu et al. |
| 2011/0000961 A1 | 1/2011 | McNeal |
| 2011/0015853 A1 | 1/2011 | DeKock et al. |
| 2011/0018736 A1 | 1/2011 | Carr |
| 2011/0021213 A1 | 1/2011 | Carr |
| 2011/0021234 A1 | 1/2011 | Tibbits et al. |
| 2011/0028138 A1 | 2/2011 | Davies-Moore et al. |
| 2011/0032110 A1 | 2/2011 | Taguchi |
| 2011/0035098 A1 | 2/2011 | Goto et al. |
| 2011/0035141 A1 | 2/2011 | Barker et al. |
| 2011/0040438 A1 | 2/2011 | Kluge et al. |
| 2011/0050589 A1 | 3/2011 | Yan et al. |
| 2011/0053506 A1 | 3/2011 | Lemke et al. |
| 2011/0077808 A1 | 3/2011 | Hyde et al. |
| 2011/0078024 A1 | 3/2011 | Messier et al. |
| 2011/0080282 A1 | 4/2011 | Kleve et al. |
| 2011/0082615 A1 | 4/2011 | Small et al. |
| 2011/0084824 A1 | 4/2011 | Tewari et al. |
| 2011/0090078 A1 | 4/2011 | Kim et al. |
| 2011/0092159 A1 | 4/2011 | Park et al. |
| 2011/0093154 A1 | 4/2011 | Moinzadeh et al. |
| 2011/0093158 A1 | 4/2011 | Theisen et al. |
| 2011/0093438 A1 | 4/2011 | Poulsen |
| 2011/0093846 A1 | 4/2011 | Moinzadeh et al. |
| 2011/0105097 A1 | 5/2011 | Tadayon et al. |
| 2011/0106375 A1 | 5/2011 | Sundaram et al. |
| 2011/0112717 A1 | 5/2011 | Resner |
| 2011/0112969 A1 | 5/2011 | Zaid et al. |
| 2011/0117933 A1 | 5/2011 | Andersson |
| 2011/0119344 A1 | 5/2011 | Eustis |
| 2011/0130915 A1 | 6/2011 | Wright et al. |
| 2011/0134749 A1 | 6/2011 | Speks et al. |
| 2011/0137520 A1 | 6/2011 | Rector et al. |
| 2011/0145331 A1 | 6/2011 | Christie et al. |
| 2011/0172873 A1 | 7/2011 | Szwabowski et al. |
| 2011/0175754 A1 | 7/2011 | Karpinsky |
| 2011/0183658 A1 | 7/2011 | Zellner |
| 2011/0187520 A1 | 8/2011 | Filev et al. |
| 2011/0190972 A1 | 8/2011 | Timmons et al. |
| 2011/0193707 A1 | 8/2011 | Ngo |
| 2011/0193726 A1 | 8/2011 | Szwabowski et al. |
| 2011/0195699 A1 | 8/2011 | Tadayon et al. |
| 2011/0197187 A1 | 8/2011 | Roh |
| 2011/0205047 A1 | 8/2011 | Patel et al. |
| 2011/0209079 A1 | 8/2011 | Tarte et al. |
| 2011/0210867 A1 | 9/2011 | Benedikt |
| 2011/0212717 A1 | 9/2011 | Rhoads et al. |
| 2011/0213656 A1 | 9/2011 | Turner |
| 2011/0221656 A1 | 9/2011 | Haddick et al. |
| 2011/0224865 A1 | 9/2011 | Gordon et al. |
| 2011/0224898 A1 | 9/2011 | Scofield et al. |
| 2011/0225527 A1 | 9/2011 | Law et al. |
| 2011/0227757 A1 | 9/2011 | Chen et al. |
| 2011/0231091 A1 | 9/2011 | Gourlay et al. |
| 2011/0234369 A1 | 9/2011 | Cai et al. |
| 2011/0245999 A1 | 10/2011 | Kordonowy |
| 2011/0246210 A1 | 10/2011 | Matsur |
| 2011/0247013 A1 | 10/2011 | Feller et al. |
| 2011/0251734 A1 | 10/2011 | Schepp et al. |

(56) References Cited

U.S. PATENT DOCUMENTS

| | | |
|---|---|---|
| 2011/0257973 A1 | 10/2011 | Chutorash et al. |
| 2011/0267204 A1 | 11/2011 | Chuang et al. |
| 2011/0267205 A1 | 11/2011 | McClellan et al. |
| 2011/0286676 A1 | 11/2011 | El Dokor |
| 2011/0288765 A1 | 11/2011 | Conway |
| 2011/0291886 A1 | 12/2011 | Krieter |
| 2011/0291926 A1 | 12/2011 | Gokturk et al. |
| 2011/0298808 A1 | 12/2011 | Rovik |
| 2011/0301844 A1 | 12/2011 | Aono |
| 2011/0307354 A1 | 12/2011 | Erman et al. |
| 2011/0307570 A1 | 12/2011 | Speks |
| 2011/0309926 A1 | 12/2011 | Eikelenberg et al. |
| 2011/0309953 A1 | 12/2011 | Petite et al. |
| 2011/0313653 A1 | 12/2011 | Lindner |
| 2011/0320089 A1 | 12/2011 | Lewis |
| 2012/0006610 A1 | 1/2012 | Wallace et al. |
| 2012/0010807 A1 | 1/2012 | Zhou |
| 2012/0016581 A1 | 1/2012 | Mochizuki et al. |
| 2012/0029852 A1 | 2/2012 | Goff et al. |
| 2012/0030002 A1 | 2/2012 | Bous et al. |
| 2012/0030512 A1 | 2/2012 | Wadhwa et al. |
| 2012/0038489 A1 | 2/2012 | Goldshmidt |
| 2012/0046822 A1 | 2/2012 | Anderson |
| 2012/0047530 A1 | 2/2012 | Shkedi |
| 2012/0053793 A1 | 3/2012 | Sala et al. |
| 2012/0053888 A1 | 3/2012 | Stahlin et al. |
| 2012/0059789 A1 | 3/2012 | Sakai et al. |
| 2012/0065815 A1 | 3/2012 | Hess |
| 2012/0065834 A1 | 3/2012 | Senart |
| 2012/0068956 A1 | 3/2012 | Jira et al. |
| 2012/0071097 A1 | 3/2012 | Matsushita et al. |
| 2012/0072244 A1 | 3/2012 | Collins et al. |
| 2012/0074770 A1 | 3/2012 | Lee |
| 2012/0083947 A1 | 4/2012 | Anderson et al. |
| 2012/0083960 A1 | 4/2012 | Zhu et al. |
| 2012/0083971 A1 | 4/2012 | Preston |
| 2012/0084773 A1 | 4/2012 | Lee et al. |
| 2012/0089299 A1 | 4/2012 | Breed |
| 2012/0092251 A1 | 4/2012 | Hashimoto et al. |
| 2012/0101876 A1 | 4/2012 | Truvey et al. |
| 2012/0101914 A1 | 4/2012 | Kumar et al. |
| 2012/0105613 A1 | 5/2012 | Weng et al. |
| 2012/0106114 A1 | 5/2012 | Caron et al. |
| 2012/0109446 A1 | 5/2012 | Yousefi et al. |
| 2012/0109451 A1 | 5/2012 | Tan |
| 2012/0110356 A1 | 5/2012 | Yousefi et al. |
| 2012/0113822 A1 | 5/2012 | Letner |
| 2012/0115446 A1 | 5/2012 | Guatama et al. |
| 2012/0116609 A1 | 5/2012 | Jung et al. |
| 2012/0116678 A1 | 5/2012 | Witmer |
| 2012/0116696 A1 | 5/2012 | Wank |
| 2012/0146766 A1 | 6/2012 | Geisler et al. |
| 2012/0146809 A1 | 6/2012 | Oh et al. |
| 2012/0149341 A1 | 6/2012 | Tadayon et al. |
| 2012/0150651 A1 | 6/2012 | Hoffberg et al. |
| 2012/0155636 A1 | 6/2012 | Muthaiah |
| 2012/0158436 A1 | 6/2012 | Bauer et al. |
| 2012/0173135 A1 | 7/2012 | Gutman |
| 2012/0173900 A1 | 7/2012 | Diab et al. |
| 2012/0173905 A1 | 7/2012 | Diab et al. |
| 2012/0179325 A1 | 7/2012 | Faenger |
| 2012/0179547 A1 | 7/2012 | Besore et al. |
| 2012/0188876 A1 | 7/2012 | Chow et al. |
| 2012/0197523 A1 | 8/2012 | Kirsch |
| 2012/0197669 A1 | 8/2012 | Kote et al. |
| 2012/0204166 A1 | 8/2012 | Ichihara |
| 2012/0210160 A1 | 8/2012 | Fuhrman |
| 2012/0215375 A1 | 8/2012 | Chang |
| 2012/0217928 A1 | 8/2012 | Kulidjian |
| 2012/0218125 A1 | 8/2012 | Demirdjian et al. |
| 2012/0226413 A1 | 9/2012 | Chen et al. |
| 2012/0238286 A1 | 9/2012 | Mallavarapu et al. |
| 2012/0239242 A1 | 9/2012 | Uehara |
| 2012/0242510 A1 | 9/2012 | Choi et al. |
| 2012/0254763 A1 | 10/2012 | Protopapas et al. |
| 2012/0254804 A1 | 10/2012 | Shema et al. |
| 2012/0259951 A1 | 10/2012 | Schalk et al. |
| 2012/0265359 A1 | 10/2012 | Das |
| 2012/0269432 A1 | 10/2012 | Wang et al. |
| 2012/0274459 A1 | 11/2012 | Jaisimha et al. |
| 2012/0274481 A1 | 11/2012 | Ginsberg et al. |
| 2012/0284292 A1 | 11/2012 | Rechsteiner et al. |
| 2012/0289217 A1 | 11/2012 | Reimer et al. |
| 2012/0289253 A1 | 11/2012 | Haag et al. |
| 2012/0296567 A1 | 11/2012 | Breed |
| 2012/0313771 A1 | 12/2012 | Wottlifff, III |
| 2012/0316720 A1 | 12/2012 | Hyde et al. |
| 2012/0317561 A1 | 12/2012 | Aslam et al. |
| 2012/0323413 A1 | 12/2012 | Kedar-Dongarkar et al. |
| 2012/0327231 A1 | 12/2012 | Cochran et al. |
| 2013/0005263 A1 | 1/2013 | Sakata |
| 2013/0005414 A1 | 1/2013 | Bindra et al. |
| 2013/0013157 A1 | 1/2013 | Kim et al. |
| 2013/0015814 A1 | 1/2013 | Kelty et al. |
| 2013/0019252 A1 | 1/2013 | Haase et al. |
| 2013/0024060 A1 | 1/2013 | Sukkarie et al. |
| 2013/0030645 A1 | 1/2013 | Divine et al. |
| 2013/0030811 A1 | 1/2013 | Olleon et al. |
| 2013/0031540 A1 | 1/2013 | Throop et al. |
| 2013/0031541 A1 | 1/2013 | Wilks et al. |
| 2013/0035063 A1 | 2/2013 | Fisk et al. |
| 2013/0046624 A1 | 2/2013 | Caiman |
| 2013/0050069 A1 | 2/2013 | Ota |
| 2013/0055096 A1 | 2/2013 | Kim et al. |
| 2013/0059607 A1 | 3/2013 | Herz et al. |
| 2013/0063336 A1 | 3/2013 | Sugimoto et al. |
| 2013/0066512 A1 | 3/2013 | Willard et al. |
| 2013/0067599 A1 | 3/2013 | Raje et al. |
| 2013/0075530 A1 | 3/2013 | Shander et al. |
| 2013/0079964 A1 | 3/2013 | Sukkarie et al. |
| 2013/0083805 A1 | 4/2013 | Lu et al. |
| 2013/0085787 A1 | 4/2013 | Gore et al. |
| 2013/0086164 A1 | 4/2013 | Wheeler et al. |
| 2013/0099915 A1 | 4/2013 | Prasad et al. |
| 2013/0103196 A1 | 4/2013 | Monceaux et al. |
| 2013/0105264 A1 | 5/2013 | Ruth et al. |
| 2013/0116882 A1 | 5/2013 | Link et al. |
| 2013/0116915 A1 | 5/2013 | Ferreira et al. |
| 2013/0134730 A1 | 5/2013 | Ricci |
| 2013/0135118 A1 | 5/2013 | Ricci |
| 2013/0138591 A1 | 5/2013 | Ricci |
| 2013/0138714 A1 | 5/2013 | Ricci |
| 2013/0139140 A1 | 5/2013 | Rao et al. |
| 2013/0141247 A1 | 6/2013 | Ricci |
| 2013/0141252 A1 | 6/2013 | Ricci |
| 2013/0143495 A1 | 6/2013 | Ricci |
| 2013/0143546 A1 | 6/2013 | Ricci |
| 2013/0143601 A1 | 6/2013 | Ricci |
| 2013/0144459 A1 | 6/2013 | Ricci |
| 2013/0144460 A1 | 6/2013 | Ricci |
| 2013/0144461 A1 | 6/2013 | Ricci |
| 2013/0144462 A1 | 6/2013 | Ricci |
| 2013/0144463 A1 | 6/2013 | Ricci et al. |
| 2013/0144469 A1 | 6/2013 | Ricci |
| 2013/0144470 A1 | 6/2013 | Ricci |
| 2013/0144474 A1 | 6/2013 | Ricci |
| 2013/0144486 A1 | 6/2013 | Ricci |
| 2013/0144520 A1 | 6/2013 | Ricci |
| 2013/0144657 A1 | 6/2013 | Ricci |
| 2013/0145065 A1 | 6/2013 | Ricci |
| 2013/0145279 A1 | 6/2013 | Ricci |
| 2013/0145297 A1 | 6/2013 | Ricci et al. |
| 2013/0145360 A1 | 6/2013 | Ricci |
| 2013/0145401 A1 | 6/2013 | Ricci |
| 2013/0145482 A1 | 6/2013 | Ricci et al. |
| 2013/0147638 A1 | 6/2013 | Ricci |
| 2013/0151031 A1 | 6/2013 | Ricci |
| 2013/0151065 A1 | 6/2013 | Ricci |
| 2013/0151088 A1 | 6/2013 | Ricci |
| 2013/0151288 A1 | 6/2013 | Bowne et al. |
| 2013/0152003 A1 | 6/2013 | Ricci et al. |
| 2013/0154298 A1 | 6/2013 | Ricci |
| 2013/0157640 A1 | 6/2013 | Aycock |
| 2013/0157647 A1 | 6/2013 | Kolodziej |

(56) References Cited

U.S. PATENT DOCUMENTS

| | | |
|---|---|---|
| 2013/0158778 A1 | 6/2013 | Tengler et al. |
| 2013/0158821 A1 | 6/2013 | Ricci |
| 2013/0166096 A1 | 6/2013 | Jotanovic |
| 2013/0166097 A1 | 6/2013 | Ricci |
| 2013/0166098 A1 | 6/2013 | Lavie et al. |
| 2013/0166109 A1 | 6/2013 | Ginsberg |
| 2013/0166152 A1 | 6/2013 | Butterworth |
| 2013/0166208 A1 | 6/2013 | Forstall et al. |
| 2013/0167159 A1 | 6/2013 | Ricci et al. |
| 2013/0173531 A1 | 7/2013 | Rinearson et al. |
| 2013/0179057 A1 | 7/2013 | Fisher et al. |
| 2013/0179689 A1 | 7/2013 | Matsumoto et al. |
| 2013/0190978 A1 | 7/2013 | Kato et al. |
| 2013/0194108 A1 | 8/2013 | Lapiotis et al. |
| 2013/0197796 A1 | 8/2013 | Obradovich et al. |
| 2013/0197797 A1 | 8/2013 | Boddy et al. |
| 2013/0198031 A1 | 8/2013 | Mitchell et al. |
| 2013/0198737 A1 | 8/2013 | Ricci |
| 2013/0198802 A1 | 8/2013 | Ricci |
| 2013/0200991 A1 | 8/2013 | Ricci et al. |
| 2013/0203400 A1 | 8/2013 | Ricci |
| 2013/0204455 A1 | 8/2013 | Chia et al. |
| 2013/0204457 A1 | 8/2013 | King |
| 2013/0204466 A1 | 8/2013 | Ricci |
| 2013/0204484 A1 | 8/2013 | Ricci |
| 2013/0204493 A1 | 8/2013 | Ricci et al. |
| 2013/0204943 A1 | 8/2013 | Ricci |
| 2013/0205026 A1 | 8/2013 | Ricci |
| 2013/0205412 A1 | 8/2013 | Ricci |
| 2013/0207794 A1 | 8/2013 | Patel et al. |
| 2013/0212065 A1 | 8/2013 | Rahnama |
| 2013/0212659 A1 | 8/2013 | Maher et al. |
| 2013/0215116 A1 | 8/2013 | Siddique et al. |
| 2013/0218412 A1 | 8/2013 | Ricci |
| 2013/0218445 A1 | 8/2013 | Basir |
| 2013/0219039 A1 | 8/2013 | Ricci |
| 2013/0226365 A1 | 8/2013 | Brozovich |
| 2013/0226371 A1 | 8/2013 | Rovik et al. |
| 2013/0226392 A1 | 8/2013 | Schneider et al. |
| 2013/0226449 A1 | 8/2013 | Rovik et al. |
| 2013/0226622 A1 | 8/2013 | Adamson et al. |
| 2013/0227648 A1 | 8/2013 | Ricci |
| 2013/0231784 A1 | 9/2013 | Rovik et al. |
| 2013/0231800 A1 | 9/2013 | Ricci |
| 2013/0232142 A1 | 9/2013 | Nielsen et al. |
| 2013/0238165 A1 | 9/2013 | Garrett et al. |
| 2013/0241720 A1 | 9/2013 | Ricci et al. |
| 2013/0245882 A1 | 9/2013 | Ricci |
| 2013/0250933 A1 | 9/2013 | Yousefi et al. |
| 2013/0261871 A1 | 10/2013 | Hobbs et al. |
| 2013/0261966 A1 | 10/2013 | Wang et al. |
| 2013/0265178 A1 | 10/2013 | Tengler et al. |
| 2013/0274997 A1 | 10/2013 | Chien |
| 2013/0279111 A1 | 10/2013 | Lee |
| 2013/0279491 A1 | 10/2013 | Rubin et al. |
| 2013/0282238 A1 | 10/2013 | Ricci et al. |
| 2013/0282357 A1 | 10/2013 | Rubin et al. |
| 2013/0282946 A1 | 10/2013 | Ricci |
| 2013/0288606 A1 | 10/2013 | Kirsch |
| 2013/0293364 A1 | 11/2013 | Ricci et al. |
| 2013/0293452 A1 | 11/2013 | Ricci et al. |
| 2013/0293480 A1 | 11/2013 | Kritt et al. |
| 2013/0295901 A1 | 11/2013 | Abramson et al. |
| 2013/0295908 A1 | 11/2013 | Zeinstra et al. |
| 2013/0295913 A1 | 11/2013 | Matthews et al. |
| 2013/0297195 A1 | 11/2013 | Das et al. |
| 2013/0300554 A1 | 11/2013 | Braden |
| 2013/0301584 A1 | 11/2013 | Addepalli et al. |
| 2013/0304371 A1 | 11/2013 | Kitatani et al. |
| 2013/0308265 A1 | 11/2013 | Arnouse |
| 2013/0309977 A1 | 11/2013 | Heines et al. |
| 2013/0311038 A1 | 11/2013 | Kim et al. |
| 2013/0325453 A1 | 12/2013 | Levien et al. |
| 2013/0325568 A1 | 12/2013 | Mangalvedkar et al. |
| 2013/0329372 A1 | 12/2013 | Wilkins |
| 2013/0332023 A1 | 12/2013 | Bertosa et al. |
| 2013/0338914 A1 | 12/2013 | Weiss |
| 2013/0339027 A1 | 12/2013 | Dokor et al. |
| 2013/0345929 A1 | 12/2013 | Bowden et al. |
| 2014/0021915 A1 | 1/2014 | Staley |
| 2014/0028542 A1 | 1/2014 | Lovitt et al. |
| 2014/0032014 A1 | 1/2014 | DeBiasio et al. |
| 2014/0054957 A1 | 2/2014 | Bellis |
| 2014/0058672 A1 | 2/2014 | Wansley et al. |
| 2014/0066014 A1 | 3/2014 | Nicholson et al. |
| 2014/0067201 A1 | 3/2014 | Visintainer et al. |
| 2014/0067564 A1 | 3/2014 | Yuan |
| 2014/0070917 A1 | 3/2014 | Protopapas |
| 2014/0081544 A1 | 3/2014 | Fry |
| 2014/0088798 A1 | 3/2014 | Himmelstein |
| 2014/0096068 A1 | 4/2014 | Dewan et al. |
| 2014/0097955 A1 | 4/2014 | Lovitt et al. |
| 2014/0109075 A1 | 4/2014 | Hoffman et al. |
| 2014/0109080 A1 | 4/2014 | Ricci |
| 2014/0120829 A1 | 5/2014 | Bhamidipati et al. |
| 2014/0121862 A1 | 5/2014 | Zarrella et al. |
| 2014/0125485 A1 | 5/2014 | Juhasz |
| 2014/0125802 A1 | 5/2014 | Beckert et al. |
| 2014/0143839 A1 | 5/2014 | Ricci |
| 2014/0156133 A1 | 6/2014 | Cullinane et al. |
| 2014/0164611 A1 | 6/2014 | Molettiere et al. |
| 2014/0168062 A1 | 6/2014 | Katz et al. |
| 2014/0168436 A1 | 6/2014 | Pedicino |
| 2014/0169621 A1 | 6/2014 | Burr |
| 2014/0171752 A1 | 6/2014 | Park et al. |
| 2014/0172290 A1 | 6/2014 | Prokhorov et al. |
| 2014/0172727 A1 | 6/2014 | Abhyanker et al. |
| 2014/0188533 A1 | 7/2014 | Davidson |
| 2014/0195272 A1 | 7/2014 | Sadiq et al. |
| 2014/0198216 A1 | 7/2014 | Zhai et al. |
| 2014/0200737 A1 | 7/2014 | Lortz et al. |
| 2014/0207328 A1 | 7/2014 | Wolf et al. |
| 2014/0220966 A1 | 8/2014 | Muetzel et al. |
| 2014/0222298 A1 | 8/2014 | Gurin |
| 2014/0223384 A1 | 8/2014 | Graumann |
| 2014/0240089 A1 | 8/2014 | Chang |
| 2014/0244078 A1 | 8/2014 | Downey et al. |
| 2014/0244096 A1 | 8/2014 | An et al. |
| 2014/0244111 A1 | 8/2014 | Gross et al. |
| 2014/0244156 A1 | 8/2014 | Magnusson et al. |
| 2014/0245277 A1 | 8/2014 | Petro et al. |
| 2014/0245278 A1 | 8/2014 | Zellen |
| 2014/0245284 A1 | 8/2014 | Alrabady et al. |
| 2014/0252091 A1 | 9/2014 | Morse et al. |
| 2014/0257627 A1 | 9/2014 | Hagan, Jr. |
| 2014/0267035 A1 | 9/2014 | Schalk et al. |
| 2014/0277936 A1 | 9/2014 | El Dokor et al. |
| 2014/0278070 A1 | 9/2014 | McGavran et al. |
| 2014/0278071 A1 | 9/2014 | San Filippo et al. |
| 2014/0278086 A1 | 9/2014 | San Filippo et al. |
| 2014/0281971 A1 | 9/2014 | Isbell, III et al. |
| 2014/0282161 A1 | 9/2014 | Cash |
| 2014/0282278 A1 | 9/2014 | Anderson et al. |
| 2014/0282470 A1 | 9/2014 | Buga et al. |
| 2014/0282931 A1 | 9/2014 | Protopapas |
| 2014/0292545 A1 | 10/2014 | Nemoto |
| 2014/0292665 A1 | 10/2014 | Lathrop et al. |
| 2014/0303899 A1 | 10/2014 | Fung |
| 2014/0306799 A1 | 10/2014 | Ricci |
| 2014/0306814 A1 | 10/2014 | Ricci |
| 2014/0306817 A1 | 10/2014 | Ricci |
| 2014/0306826 A1 | 10/2014 | Ricci |
| 2014/0306833 A1 | 10/2014 | Ricci |
| 2014/0306834 A1 | 10/2014 | Ricci |
| 2014/0306835 A1 | 10/2014 | Ricci |
| 2014/0307655 A1 | 10/2014 | Ricci |
| 2014/0307724 A1 | 10/2014 | Ricci |
| 2014/0308902 A1 | 10/2014 | Ricci |
| 2014/0309789 A1 | 10/2014 | Ricci |
| 2014/0309790 A1 | 10/2014 | Ricci |
| 2014/0309804 A1 | 10/2014 | Ricci |
| 2014/0309805 A1 | 10/2014 | Ricci |
| 2014/0309806 A1 | 10/2014 | Ricci |
| 2014/0309813 A1 | 10/2014 | Ricci |

(56) References Cited

U.S. PATENT DOCUMENTS

| | | |
|---|---|---|
| 2014/0309814 A1 | 10/2014 | Ricci et al. |
| 2014/0309815 A1 | 10/2014 | Ricci et al. |
| 2014/0309838 A1 | 10/2014 | Ricci |
| 2014/0309839 A1 | 10/2014 | Ricci et al. |
| 2014/0309847 A1 | 10/2014 | Ricci |
| 2014/0309849 A1 | 10/2014 | Ricci |
| 2014/0309852 A1 | 10/2014 | Ricci |
| 2014/0309853 A1 | 10/2014 | Ricci |
| 2014/0309862 A1 | 10/2014 | Ricci |
| 2014/0309863 A1 | 10/2014 | Ricci |
| 2014/0309864 A1 | 10/2014 | Ricci |
| 2014/0309865 A1 | 10/2014 | Ricci |
| 2014/0309866 A1 | 10/2014 | Ricci |
| 2014/0309867 A1 | 10/2014 | Ricci |
| 2014/0309868 A1 | 10/2014 | Ricci |
| 2014/0309869 A1 | 10/2014 | Ricci |
| 2014/0309870 A1 | 10/2014 | Ricci et al. |
| 2014/0309871 A1 | 10/2014 | Ricci |
| 2014/0309872 A1 | 10/2014 | Ricci |
| 2014/0309873 A1 | 10/2014 | Ricci |
| 2014/0309874 A1 | 10/2014 | Ricci |
| 2014/0309875 A1 | 10/2014 | Ricci |
| 2014/0309876 A1 | 10/2014 | Ricci |
| 2014/0309877 A1 | 10/2014 | Ricci |
| 2014/0309878 A1 | 10/2014 | Ricci |
| 2014/0309879 A1 | 10/2014 | Ricci |
| 2014/0309880 A1 | 10/2014 | Ricci |
| 2014/0309885 A1 | 10/2014 | Ricci |
| 2014/0309886 A1 | 10/2014 | Ricci |
| 2014/0309891 A1 | 10/2014 | Ricci |
| 2014/0309892 A1 | 10/2014 | Ricci |
| 2014/0309893 A1 | 10/2014 | Ricci |
| 2014/0309913 A1 | 10/2014 | Ricci et al. |
| 2014/0309919 A1 | 10/2014 | Ricci |
| 2014/0309920 A1 | 10/2014 | Ricci |
| 2014/0309921 A1 | 10/2014 | Ricci et al. |
| 2014/0309922 A1 | 10/2014 | Ricci |
| 2014/0309923 A1 | 10/2014 | Ricci |
| 2014/0309927 A1 | 10/2014 | Ricci |
| 2014/0309929 A1 | 10/2014 | Ricci |
| 2014/0309930 A1 | 10/2014 | Ricci |
| 2014/0309934 A1 | 10/2014 | Ricci |
| 2014/0309935 A1 | 10/2014 | Ricci |
| 2014/0309982 A1 | 10/2014 | Ricci |
| 2014/0310031 A1 | 10/2014 | Ricci |
| 2014/0310075 A1 | 10/2014 | Ricci |
| 2014/0310103 A1 | 10/2014 | Ricci |
| 2014/0310186 A1 | 10/2014 | Ricci |
| 2014/0310277 A1 | 10/2014 | Ricci |
| 2014/0310379 A1 | 10/2014 | Ricci et al. |
| 2014/0310594 A1 | 10/2014 | Ricci et al. |
| 2014/0310610 A1 | 10/2014 | Ricci |
| 2014/0310702 A1 | 10/2014 | Ricci et al. |
| 2014/0310739 A1 | 10/2014 | Ricci et al. |
| 2014/0310788 A1 | 10/2014 | Ricci |
| 2014/0322676 A1 | 10/2014 | Raman |
| 2014/0347207 A1 | 11/2014 | Zeng et al. |
| 2014/0347265 A1 | 11/2014 | Allen et al. |
| 2015/0007155 A1 | 1/2015 | Hoffman et al. |
| 2015/0012186 A1 | 1/2015 | Horseman |
| 2015/0032366 A1 | 1/2015 | Man et al. |
| 2015/0032670 A1 | 1/2015 | Brazell |
| 2015/0057839 A1 | 2/2015 | Chang et al. |
| 2015/0061895 A1 | 3/2015 | Ricci |
| 2015/0066284 A1 | 3/2015 | Yopp |
| 2015/0081133 A1 | 3/2015 | Schulz |
| 2015/0081167 A1 | 3/2015 | Pisz et al. |
| 2015/0088423 A1 | 3/2015 | Tuukkanen |
| 2015/0088515 A1 | 3/2015 | Beaumont et al. |
| 2015/0116200 A1 | 4/2015 | Kurosawa et al. |
| 2015/0158499 A1 | 6/2015 | Koravadi |
| 2015/0178034 A1 | 6/2015 | Penilia et al. |
| 2015/0233720 A1 | 8/2015 | Harada |
| 2015/0235480 A1 | 8/2015 | Cudak et al. |
| 2015/0241233 A1 | 8/2015 | Loftus et al. |
| 2015/0294329 A1 | 10/2015 | Saito et al. |
| 2015/0298565 A1 | 10/2015 | Iwamura et al. |
| 2015/0343918 A1 | 12/2015 | Watanabe et al. |
| 2015/0345971 A1 | 12/2015 | Meuleau et al. |
| 2016/0003637 A1 | 1/2016 | Andersen |
| 2016/0008985 A1 | 1/2016 | Kim et al. |
| 2016/0009291 A1 | 1/2016 | Pallett et al. |
| 2016/0009295 A1 | 1/2016 | Chun et al. |
| 2016/0009391 A1 | 1/2016 | Friesel |
| 2016/0026182 A1 | 1/2016 | Boroditsky et al. |
| 2016/0031441 A1 | 2/2016 | Foley |
| 2016/0046288 A1 | 2/2016 | Pawlicki et al. |
| 2016/0059856 A1 | 3/2016 | Van Dan Elzen et al. |
| 2016/0061612 A1 | 3/2016 | You et al. |
| 2016/0070527 A1 | 3/2016 | Ricci |
| 2016/0086391 A1 | 3/2016 | Ricci |
| 2016/0129908 A1 | 5/2016 | Harda |
| 2016/0161272 A1 | 6/2016 | Shigezumi et al. |
| 2016/0202074 A1 | 7/2016 | Woodard et al. |
| 2016/0221573 A1* | 8/2016 | Prokhorov ...... B60W 30/18154 |
| 2016/0269456 A1 | 9/2016 | Ricci |
| 2016/0269469 A1 | 9/2016 | Ricci |
| 2016/0273927 A1 | 9/2016 | Kitajima et al. |
| 2016/0276854 A1 | 9/2016 | Lian |
| 2016/0334236 A1 | 11/2016 | Mason et al. |
| 2016/0355192 A1 | 12/2016 | James et al. |
| 2016/0368396 A1 | 12/2016 | Konet et al. |
| 2016/0368491 A1* | 12/2016 | Hauler ............ B60W 60/00186 |
| 2016/0375788 A1 | 12/2016 | Liu |
| 2017/0008523 A1 | 1/2017 | Christensen et al. |
| 2017/0015288 A1 | 1/2017 | Coelingh et al. |
| 2017/0021837 A1 | 1/2017 | Ebina |
| 2017/0030728 A1 | 2/2017 | Baglino et al. |
| 2017/0036673 A1 | 2/2017 | Lee |
| 2017/0053538 A1 | 2/2017 | Samarasekera et al. |
| 2017/0057507 A1 | 3/2017 | Gordon et al. |
| 2017/0057542 A1 | 3/2017 | Kim et al. |
| 2017/0076455 A1 | 3/2017 | Newman et al. |
| 2017/0087999 A1 | 3/2017 | Miller et al. |
| 2017/0088000 A1 | 3/2017 | Payne et al. |
| 2017/0088117 A1 | 3/2017 | Ogawa |
| 2017/0143246 A1 | 5/2017 | Flickinger |
| 2017/0212515 A1 | 7/2017 | Bertollini et al. |
| 2017/0242442 A1 | 8/2017 | Minster |
| 2017/0267256 A1 | 9/2017 | Minster et al. |
| 2017/0291615 A1 | 10/2017 | Kusano et al. |
| 2017/0294000 A1 | 10/2017 | Shen et al. |
| 2017/0307392 A1 | 10/2017 | Kitajima et al. |
| 2017/0328716 A1 | 11/2017 | Ma |
| 2017/0349045 A1 | 12/2017 | McNew |
| 2017/0349185 A1 | 12/2017 | McNew |
| 2017/0355377 A1 | 12/2017 | Vijaya Kumar et al. |
| 2018/0052463 A1 | 2/2018 | Mays |
| 2018/0066957 A1 | 3/2018 | Stroila et al. |
| 2018/0082213 A1 | 3/2018 | McCord |
| 2018/0109482 A1 | 4/2018 | DeLuca et al. |
| 2018/0113450 A1 | 4/2018 | Sherony |
| 2018/0118219 A1 | 5/2018 | Hiei et al. |
| 2018/0120123 A1 | 5/2018 | Seok et al. |
| 2018/0127001 A1 | 5/2018 | Ricci |
| 2018/0143029 A1 | 5/2018 | Nikulin et al. |
| 2018/0143639 A1 | 5/2018 | Singhal et al. |
| 2018/0151064 A1 | 5/2018 | Xu et al. |
| 2018/0170382 A1 | 6/2018 | Soliman et al. |
| 2018/0202825 A1 | 7/2018 | You et al. |
| 2018/0208209 A1 | 7/2018 | Al-Dahle et al. |
| 2018/0276351 A1 | 9/2018 | Patton et al. |
| 2018/0293466 A1 | 10/2018 | Viswanathan |
| 2018/0373268 A1 | 12/2018 | Antunes Marques Esteves |
| 2019/0004526 A1 | 1/2019 | Soliman |
| 2019/0012909 A1 | 1/2019 | Mintz |
| 2019/0017828 A1 | 1/2019 | Harish et al. |
| 2019/0031037 A1 | 1/2019 | Fendt |
| 2019/0041228 A1 | 2/2019 | Singhal |
| 2019/0080142 A1 | 3/2019 | Abeywardena et al. |
| 2019/0107406 A1 | 4/2019 | Cox et al. |
| 2019/0113916 A1* | 4/2019 | Guo ...................... B60W 50/02 |
| 2019/0141480 A1 | 5/2019 | Tung et al. |
| 2019/0146500 A1 | 5/2019 | Yalla et al. |

(56) References Cited

U.S. PATENT DOCUMENTS

| | | |
|---|---|---|
| 2019/0186939 A1 | 6/2019 | Cox et al. |
| 2019/0226851 A1 | 7/2019 | Nicosevici et al. |
| 2019/0286793 A1 | 9/2019 | Patton et al. |
| 2020/0234582 A1 | 7/2020 | Mintz |

FOREIGN PATENT DOCUMENTS

| | | |
|---|---|---|
| CN | 101303878 | 11/2008 |
| CN | 102467827 | 5/2012 |
| EP | 1223567 | 7/2002 |
| EP | 1484729 | 12/2004 |
| EP | 2192015 | 6/2010 |
| JP | 2004-284450 | 10/2004 |
| KR | 2006-0128484 | 12/2006 |
| WO | WO 2007/126204 | 11/2007 |
| WO | WO 2012/102879 | 8/2012 |
| WO | WO 2013/074866 | 5/2013 |
| WO | WO 2013/074867 | 5/2013 |
| WO | WO 2013/074868 | 5/2013 |
| WO | WO 2013/074897 | 5/2013 |
| WO | WO 2013/074899 | 5/2013 |
| WO | WO 2013/074901 | 5/2013 |
| WO | WO 2013/074919 | 5/2013 |
| WO | WO 2013/074981 | 5/2013 |
| WO | WO 2013/074983 | 5/2013 |
| WO | WO 2013/075005 | 5/2013 |
| WO | WO 2013/181310 | 12/2013 |
| WO | WO 2014/014862 | 1/2014 |
| WO | WO 2014/139821 | 9/2014 |
| WO | WO 2014/143563 | 9/2014 |
| WO | WO 2014/158667 | 10/2014 |
| WO | WO 2014/158672 | 10/2014 |
| WO | WO 2014/158766 | 10/2014 |
| WO | WO 2014/172312 | 10/2014 |
| WO | WO 2014/172313 | 10/2014 |
| WO | WO 2014/172316 | 10/2014 |
| WO | WO 2014/172320 | 10/2014 |
| WO | WO 2014/172322 | 10/2014 |
| WO | WO 2014/172323 | 10/2014 |
| WO | WO 2014/172327 | 10/2014 |
| WO | WO 2016/035268 | 3/2016 |
| WO | WO 2016/062730 | 4/2016 |
| WO | WO 2016/145073 | 9/2016 |
| WO | WO 2016/145100 | 9/2016 |
| WO | WO 2017/167790 | 10/2017 |

OTHER PUBLICATIONS

U.S. Appl. No. 61/567,962, filed Dec. 7, 2011, Baarman et al.
"Carpool, HOV, Transit lanes," WazeWiki, 2016, retrieved from https://wiki.waze.com/wiki/Carpool,_HOV,_Transit_lanes, retrieved on Feb. 27, 2018, 3 pages.
"Managing Demand Through Travel Information Services," U.S. Department of Transportation brochure, FHWA, retrieved from http://www.ops.fhwa.dot.gov/publications/manag_demand_tis/travelinfo.htm, retrieved on Feb. 28, 2018, 30 pages.
"Nexus 10 Guidebook for Android," Google Inc., © 2012, Edition 1.2, 166 pages.
"ORB (Oriented FAST and Rotated BRIEF)", Open CV 3.0.0-dev documentation, retrieved from https://docs.opencv.org/3.0-beta/doc/py_tutorials/py_feature2d/py_orb/py_orb.html, 2014, 3 pages.
"Self-Driving: Self-Driving Autonomous Cars," available at http://www.automotivetechnologies.com/autonomous-self-driving-cars, accessed Dec. 2016, 9 pages.
"Softmax function," Wikipedia, retrieved from https://en.wikipedia.org/wiki/Softmax_function, retrieved on Feb. 28, 2018, 4 pages.
Amor-Segan et al., "Towards the Self Healing Vehicle," Automotive Electronics, Jun. 2007, 2007 3rd Institution of Engineering and Technology Conference, 7 pages.
Badino et al., "Real-Time Topometric Localization," IEEE International Conference, Robotics and Automation, 2012, 8 pages.
Bennett, "Meet Samsung's Version of Apple AirPlay," CNET.com, Oct. 10, 2012, 11 pages.
Brubaker et al., "Lost! Leveraging the Crowd for Probabilistic Visual Self-Localization," Proceedings of the IEEE Conference on Computer Vision and Pattern Recognition, 2013, 8 pages.
Cairnie et al., "Using Finger-Pointing to Operate Secondary Controls in Automobiles," Proceedings of the IEEE Intelligent Vehicles Symposium 2000, Oct. 3-5, 2000, 6 pages.
Cathy et al., "A prescription fortransit arrival/departure prediction using automatic vehicle location data," Transportation Research Part C, 2003, vol. 11, pp. 241-264.
Clark, "How Self-Driving Cars Work: The Nuts and Bolts Behind Google's Autonomous Car Program," Feb. 21, 2015, available at http://www.makeuseof.com/tag/how-self-driving-cars-work-the-nuts-and-bolts-behind-googles-autonomous-car-program/, 9 pages.
Davies, "This NIO EP9 performance EV wants to be the Tesla of Supercars," SlashGear, 2016, retrieved from https//www.slashgear.com/nextev-nio-ep9-car-tesla-of-performance-evs-21464829, 9 pages.
Deaton et al., "How Driverless Cars Will Work," Jul. 1, 2008, HowStuffWorks.com. <http://auto.howstuffworks.com/under-the-hood/trends-innovations/driverless-car.htm> Sep. 18, 2017, 10 pages.
Dellaert et al., "Monte Carlo Localization for Mobile Robots," IEEE, Robotics and Automation, 1999 Proceedings, vol. 2, pp. 1322-1328.
Dumbaugh, "Safe Streets, Livable Streets: A Positive Approach to urban Roadside Design," Ph.D. dissertation for School of Civil & Environ. Engr., Georgia Inst. Of Technology, Dec. 2005, 235 pages.
Engel et al., "LSD-SLAM: Large-Scale Direct Monocular SLAM," Springer, Cham., European Conference, 2014, Computer Vision, pp. 834-849, 16 pages.
Fei et al., "A QoS-aware Dynamic Bandwidth Allocation Algorithm for Relay Stations in IEEE 802.16j-based Vehicular Networks," Proceedings of the 2010 IEEE Global Telecommunications Conference, Dec. 10, 2010, 6 pages.
Floros et al., "OpenStreetSLAM: Global Vehicle Localization Using OpenStreetMaps," RWTH Aachen University, Computer Vision Group, 2013, 20 pages.
Galvez-Lopez et al., "Bags of Binary Words for Fast Place Recognition in Image Sequences," IEEE Transactions on Robotics, 2012, vol. 28(5), pp. 1188-1197, abstract only, 1 page.
Ge et al., "Optimal Relay Selection in IEEE 802.16 Multihop Relay Vehicular Networks," IEEE Transactions on Vehicular Technology, 2010, vol. 59(5), pp. 2198-2206.
Grana, et al., "A Fast Approach for Integrating ORB Descriptors in the Bag of Words Model," Proceedings of SPIE—The International Society for Optical Engineering, Feb. 2013, vol. 8667, pp. 86670-866709, DOI: 10.1117/12.2008460, 9 pages.
Grauman et al., "Excerpt chapter from Synthesis lecture draft: Visual Recognition," 2012, retrieved from http://www.cs.utexas.edu/~grauman/courses/fall2009/papers/bag_of_visual_words.pdf, 8 pages.
Guizzo, "How Google's Self-Driving Car Works," Oct. 18, 2011, available at https://spectrum.ieee.org/automaton/robotics/artificial-intelligence/how-google-self-driving-car-works, 5 pages.
Haklay et al., "OpenStreetMap: User-Generated Street Maps," IEEE Pervasive Computing, 2008, pp. 12-18.
Hays et al., "IM2GPS: estimating geographic information from a single image," IEEE Conference, Computer Vision and Pattern Recognition, 2008, pp. 1-8.
Heer et al., "ALPHA: An Adaptive and Lightweight Protocol for Hop-by-hop Authentication," Proceedings of CoNEXT 2008, Dec. 2008, pp. 1-12.
Jahnich et al., "Towards a Middleware Approach for a Self-Configurable Automotive Embedded System," International Federation for Information Processing, 2008, pp. 55-65.
Kautonen, "NextEV unveils the NIO EP9 electric supercar in London," Autoblog, 2016, retrieved from http://www.autoblog.com/2016/11/21/nextev-unveiles-the-nio-ep9-electric-supercar-in-london/, 3 pages.
Kneip et al., "Robust Real-Time Visual Odometry with a Single Camera and an IMU," Proceedings of the British Machine Vision Conference, 2011, 11 pages.

(56) References Cited

OTHER PUBLICATIONS

Konolige et al., "Large-Scale Visual Odometry for Rough Terrain," Robotics Research, 2010, pp. 201-212, 12 pages.
Levinson et al., "Map-Based Precision Vehicle Localization in Urban Environments," Robotics: Science and Systems, 2007, vol. 4, 8 pages.
Ma et al., "Find your Way by Observing the Sun and Other Semantic Cues," Computer Vision and Pattern Recognition, 2016, 12 pages.
Muja et al., "Fast Approximate Nearest Neighbors with Automatic Algorithm Configuration," VISAPP International Conference on Computer Vision Theory and Applications, 2009, vol. 1, pp. 331-340, 10 pages.
Mur-Artal et al., "ORB-SLAM: a Versatile and Accurate Monocular SLAM System," IEEE Translations, Robotics, 2015, vol. 31(5), pp. 1147-1163.
Nister et al., "Visual odometry," IEEE Computer Vision and Pattern Recognition, 2004, vol. 1, 35 pages.
Persson "Adaptive Middleware for Self-Configurable Embedded Real-Time Systems," KTH Industrial Engineering and Management, 2009, 92 pages.
Raychaudhuri et al., "Emerging Wireless Technologies and the Future Mobile Internet," p. 48, Cambridge Press, 2011, 3 pages.
Rublee et al., ORB: an efficient alternative to SIFT or SURF, In Computer Vision (ICCV), 2011 IEEE international conference on (pp. 2564-2571) retrieved from http://citeseerx.ist.psu.edu/viewdoc/download?doi=10.1.1.370.4395&rep=rep1&type=pdfs, 8 pages.
Ruchti et al., "Localization on openstreetmap data using a 3D Laser Scanner," IEEE International Conference, Robotics and Automation, 2015, 6 pages.
Scaramuzza et al., "Visual Odometry[tutorial]," IEEE Robotics & Automation Magazine, 2011, vol. 18(4), pp. 80-92.
Stachniss, "Robot Mapping: Short Introduction to Particle Filters and Monte Carlo Localization," Albert-Ludwigs-Universitat Freiburg, 2012, retrieved from http://ais.informatik.uni-freiburg.de/teaching/ws12/mapping/pdf/slam09-particle-filter-4.pdf, 9 pages.
Stephens, Leah, "How Driverless Cars Work," Interesting Engineering, Apr. 28, 2016, available at https://interestingengineering.com/driverless-cars-work/, 7 pages.
Stoller, "Leader Election in Distributed Systems with Crash Failures," Indiana University, 1997, pp. 1-15.
Suwatthikul, "Fault detection and diagnosis for in-vehicle networks," Intech, 2010, pp. 283-286 [retrieved from: www.intechopen.com/books/fault-detection-and-diagnosis-for-in-vehicle-networks].
Thurn/Burgard/Fox, "Probabilistic Robotics," The MIT Press, 2010, retrieved from http://robotics.usc.edu/~gaurav/CS547/lecture6-2010-particle-filters.pdf, 51 pages.
Urmson et al., "Autonomous Driving in Urban Environments: Boss and the Urban Challenge," Journal of Field Robotics, 2008, vol. 25(8), pp. 425-466.
Walter et al., "The smart car seat: personalized monitoring of vital signs in automotive applications." Personal and Ubiquitous Computing, Oct. 2011, vol. 15, No. 7, pp. 707-715.
White, "NextEV's NIO IP9 is an incredible four-wheel-drive electric hypercar," Wired, 2016, retrieved from http://www.wired.co.uk/article/nextev-hypercar-nio-ep9, 6 pages.
Wolf et al., "Design, Implementation, and Evaluation of a Vehicular Hardware Security Module," ICISC'11 Proceedings of the 14th Int'l Conf. Information Security & Cryptology, Springer-Verlag Berlin, Heidelberg, 2011, pp. 302-318.
Wu et al., "Where am I: Place instance and category recognition using spatial PACT," IEEE Conference, Computer Vision and Pattern Recognition, 2008, 8 pages.
Zhang et al., "LOAM: Lidar Odometry and Mapping in Real-time," Robotics Science and Systems, 2014, vol. 2, 9 pages.
Zhang et al., "Real-time Depth Enhanced Monocular Odometry," IEEE/RSJ International Conference, Intelligent Robots and Systems, 2014, pp. 4973-4980.
Zhang et al., "Visual-lidar Odometry and Mapping: Low-drift, Robust, and Fast," IEEE International Conference, Robotics and Automation, 2015, pp. 2174-2181.
International Search Report and Written Opinion for U.S. International (PCT) Patent Application No. PCT/US18/53027, dated Nov. 30, 2018, 12 pages.
Official Action for U.S. Appl. No. 15/395,924, dated Jan. 25, 2018, 10 pages.
Final Action for U.S. Appl. No. 15/395,924, dated Jul. 30, 2018, 14 pages.
Official Action for U.S. Appl. No. 15/395,924, dated Nov. 19, 2018, 13 pages.
Notice of Allowance for U.S. Appl. No. 15/395,924, dated Apr. 2, 2019, 11 pages.
Official Action for U.S. Appl. No. 15/395,952, dated Aug. 3, 2018, 11 pages.
Final Action for U.S. Appl. No. 15/395,952, dated Jul. 11, 2019, 14 pages.
Official Action for U.S. Appl. No. 15/395,952, dated Jan. 13, 2020, 18 pages.
Official Action for U.S. Appl. No. 15/407,066, dated Nov. 8, 2018, 9 pages.
Official Action for U.S. Appl. No. 15/407,066, dated Mar. 12, 2019, 11 pages.
Supplemental Notice of Allowance for U.S. Appl. No. 15/407,066, dated Sep. 10, 2019, 2 pages.
Official Action for U.S. Appl. No. 15/408,143, dated Jun. 15, 2018, 9 pages.
Notice of Allowance for U.S. Appl. No. 15/408,143, dated Nov. 20, 2018, 8 pages.
Notice of Allowance for U.S. Appl. No. 15/634,197, dated Oct. 25, 2018, 8 pages.
Official Action for U.S. Appl. No. 15/665,644, dated Nov. 19, 2018, 32 pages.
Final Action for U.S. Appl. No. 15/665,644, dated Apr. 4, 2019, 19 pages.
Official Action for U.S. Appl. No. 15/665,644, dated Jul. 25, 2019, 16 pages.
Final Action for U.S. Appl. No. 15/665,644, dated Dec. 31, 2019, 18 pages.
Official Action for U.S. Appl. No. 15/848,851, dated Dec. 12, 2019, 17 pages.
Official Action for U.S. Appl. No. 15/727,838, dated Aug. 15, 2019, 17 pages.
Final Action for U.S. Appl. No. 15/727,838, dated Jan. 13, 2020, 19 pages.
Official Action for U.S. Appl. No. 15/786,373, dated Jul. 11, 2019, 14 pages.
Notice of Allowance for U.S. Appl. No. 15/786,373, dated Dec. 27, 2019, 5 pages.
Official Action for U.S. Appl. No. 15/798,016, dated Jul. 15, 2019, 7 pages.
Strunk et al., "The Elements of Style," 3d ed., Macmillan Publishing Co., 1979, 3 pages.
International Preliminary Reporton Patentability for U.S. International (PCT) Patent Application No. PCT/US18/53027, dated Apr. 30, 2020, 11 pages.
Notice of Allowance for U.S. Appl. No. 15/407,066, dated Jul. 3, 2019, 5 pages.
Notice of Allowance for U.S. Appl. No. 15/665,644, dated May 15, 2020, 5 pages.
Official Action for U.S. Appl. No. 15/727,838, dated May 8, 2020, 18 pages.
Notice of Allowance for U.S. Appl. No. 15/798,016, dated Nov. 13, 2019, 5 pages.
U.S. Appl. No. 17/202,823, filed Mar. 16, 2021, Singhal et al.
Examiner's Answer for U.S. Appl. No. 15/727,838, dated May 4, 2021, 17 pages.
Gustafsson et al., "Particle Filters for Positioning, Navigation and Tracking", IEEE Transactions on Signal Processing, Feb. 2, 2002, vol. 50(2), pp. 425-437.
Kwolek, "Finding Location Using Particle Filter and Histogram Matching", International Conference on Artificial Intelligence and Software Computing, 7th International Conference Jun. 2004, pp. 786-791.

(56) References Cited

OTHER PUBLICATIONS

Noh et al., "Particle Filter for Correction of GPS location data of mobile robot", Journal of the Korea Institute of Electronic Communication Sciences, Jan. 2012, pp. 381-389, English abstract only.
Notice of Allowance for U.S. Appl. No. 15/395,952, dated Nov. 13, 2020, 16 pages.
Notice of Allowance for U.S. Appl. No. 16/246,810, dated Oct. 20, 2020, 18 pages.
Final Action for U.S. Appl. No. 15/727,838, dated Sep. 29, 2020 23 pages.
Official Action for U.S. Appl. No. 15/395,952, dated Jul. 31, 2020, 19 pages.
Official Action for U.S. Appl. No. 15/848,851, dated Jul. 23, 2020, 21 pages.
Decision on Appeal for U.S. Appl. No. 15/727,838, dated May 5, 2022 15 pages.
Notice of Allowance for U.S. Appl. No. 17/202,823, dated Mar. 15, 2023, 16 pages.

\* cited by examiner

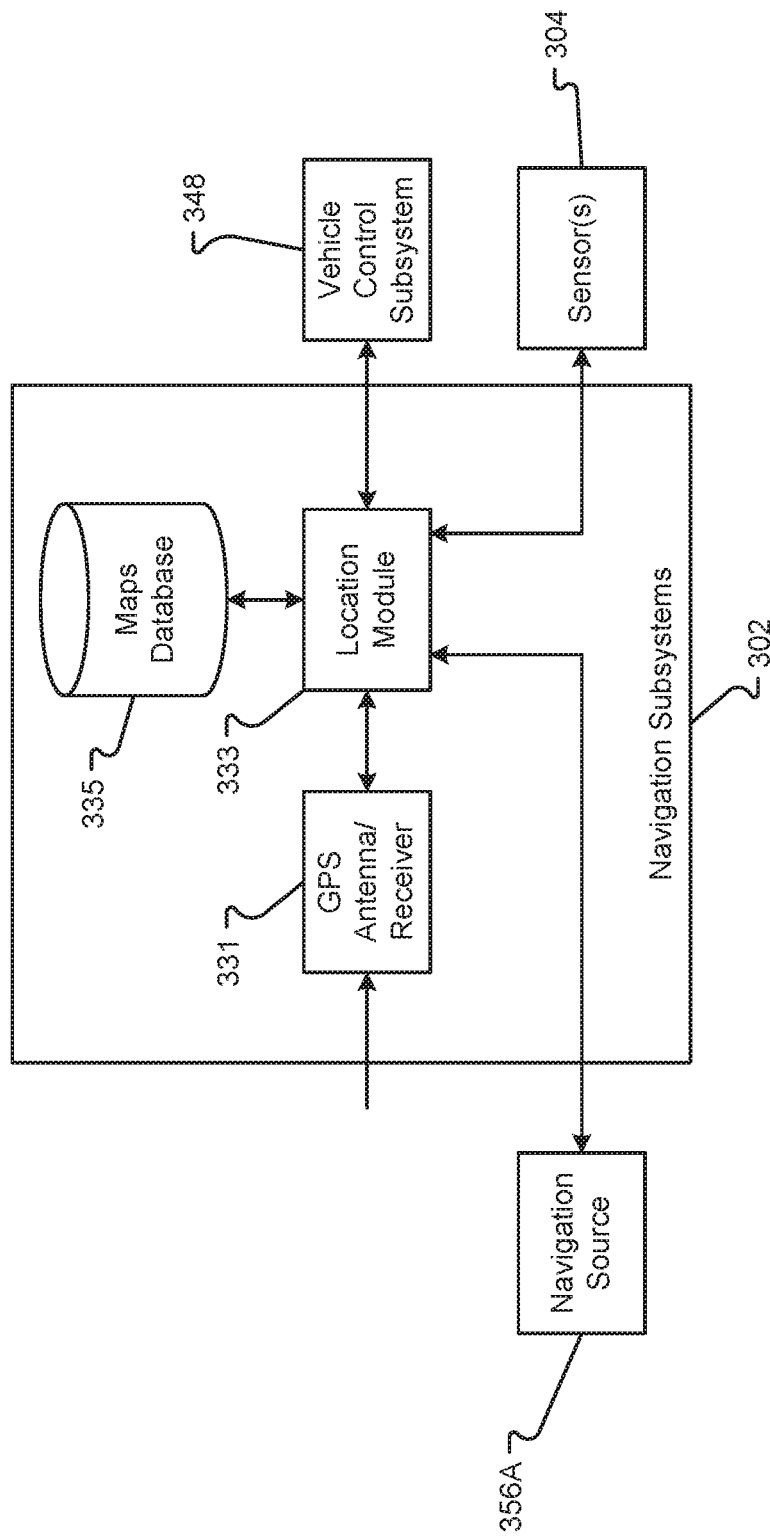

VEHICLE PATH-PLANNER MONITOR AND CONTROLLER

CROSS REFERENCE TO RELATED APPLICATION

The present application is a continuation of and claims priority to U.S. patent application Ser. No. 15/786,373, filed on Oct. 17, 2017, of the same title, the entire disclosure of which is hereby incorporated herein by reference, in its entirety, for all that it teaches and for all purposes.

FIELD

The present disclosure is generally directed to vehicle systems, in particular, toward autonomous vehicles and/or vehicles operating in an autonomous mode.

BACKGROUND

In recent years, transportation methods have changed substantially. This change is due in part to a concern over the limited availability of natural resources, a proliferation in personal technology, and a societal shift to adopt more environmentally friendly transportation solutions. These considerations have encouraged the development of a number of new flexible-fuel vehicles, hybrid-electric vehicles, and electric vehicles.

While these vehicles appear to be new they are generally implemented as a number of traditional subsystems that are merely tied to an alternative power source. In fact, the design and construction of the vehicles is limited to standard frame sizes, shapes, materials, and transportation concepts. Among other things, these limitations fail to take advantage of the benefits of new technology, power sources, and support infrastructure.

BRIEF DESCRIPTION OF THE DRAWINGS

FIG. 3C is a block diagram of an embodiment of a navigation system of the vehicle in accordance with embodiments of the present disclosure;

DETAILED DESCRIPTION

Embodiments of the present disclosure will be described in connection with a vehicle, and in some embodiments, an electric vehicle, rechargeable electric vehicle, and/or hybrid-electric vehicle and associated systems.

Figure 1:
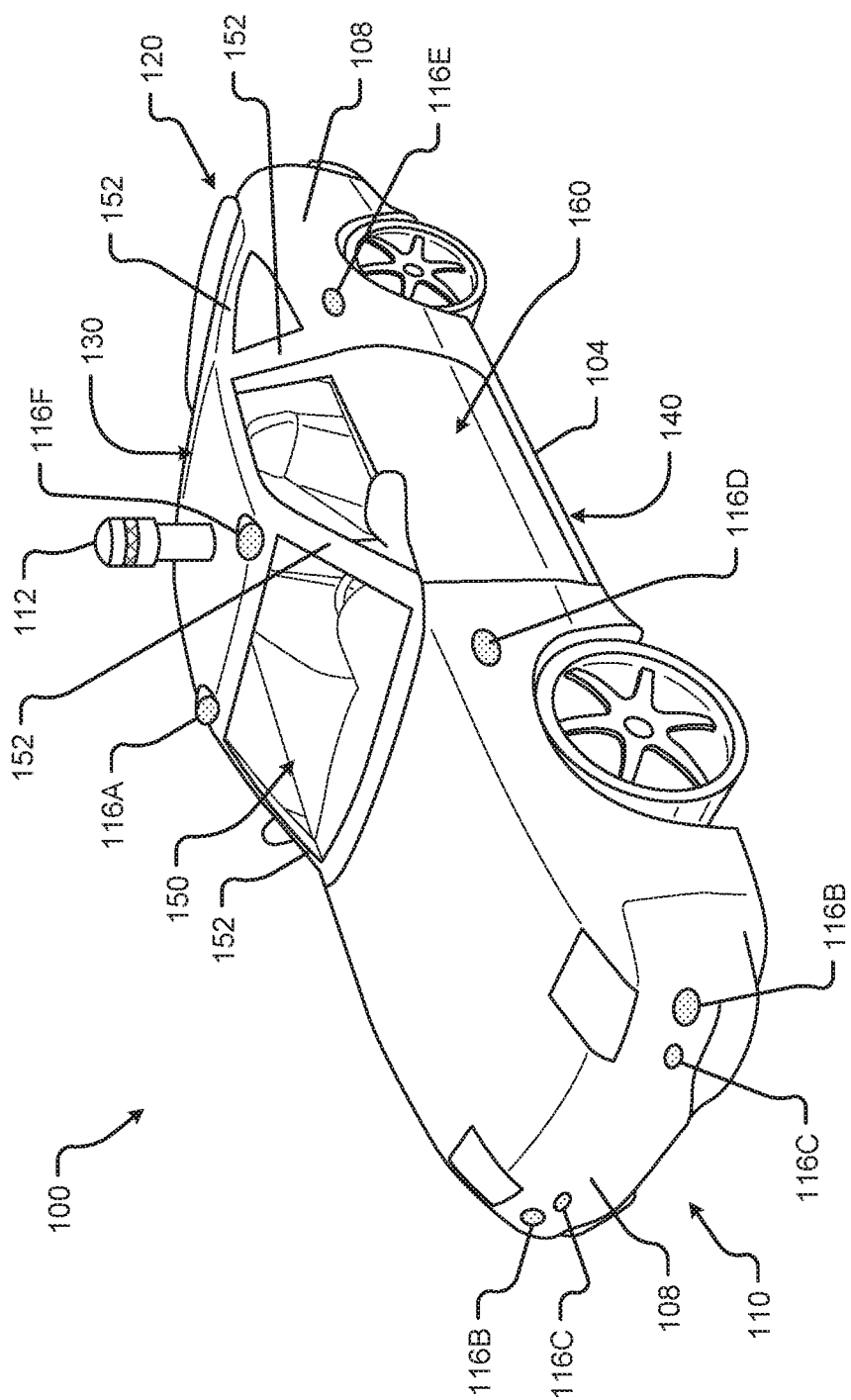
FIG. 1 shows a vehicle in accordance with embodiments of the present disclosure.

FIG. 1 shows a perspective view of a vehicle 100 in accordance with embodiments of the present disclosure. The electric vehicle 100 comprises a vehicle front 110, vehicle aft or rear 120, vehicle roof 130, at least one vehicle side 160, a vehicle undercarriage 140, and a vehicle interior 150. In any event, the vehicle 100 may include a frame 104 and one or more body panels 108 mounted or affixed thereto. The vehicle 100 may include one or more interior components (e.g., components inside an interior space 150, or user space, of a vehicle 100, etc.), exterior components (e.g., components outside of the interior space 150, or user space, of a vehicle 100, etc.), drive systems, controls systems, structural components, etc.

Although shown in the form of a car, it should be appreciated that the vehicle 100 described herein may include any conveyance or model of a conveyance, where the conveyance was designed for the purpose of moving one or more tangible objects, such as people, animals, cargo, and the like. The term "vehicle" does not require that a conveyance moves or is capable of movement. Typical vehicles may include but are in no way limited to cars, trucks, motorcycles, busses, automobiles, trains, railed conveyances, boats, ships, marine conveyances, submarine conveyances, airplanes, space craft, flying machines, human-powered conveyances, and the like.

In some embodiments, the vehicle 100 may include a number of sensors, devices, and/or systems that are capable of assisting in driving operations, e.g., autonomous or semi-autonomous control. Examples of the various sensors and systems may include, but are in no way limited to, one or more of cameras (e.g., independent, stereo, combined image, etc.), infrared (IR) sensors, radio frequency (RF) sensors, ultrasonic sensors (e.g., transducers, transceivers, etc.), RADAR sensors (e.g., object-detection sensors and/or systems), LIDAR (Light Imaging, Detection, And Ranging) systems, odometry sensors and/or devices (e.g., encoders, etc.), orientation sensors (e.g., accelerometers, gyroscopes, magnetometer, etc.), navigation sensors and systems (e.g., GPS, etc.), and other ranging, imaging, and/or object-detecting sensors. The sensors may be disposed in an interior space 150 of the vehicle 100 and/or on an outside of the vehicle 100. In some embodiments, the sensors and systems may be disposed in one or more portions of a vehicle 100 (e.g., the frame 104, a body panel, a compartment, etc.).

The vehicle sensors and systems may be selected and/or configured to suit a level of operation associated with the vehicle 100. Among other things, the number of sensors used in a system may be altered to increase or decrease information available to a vehicle control system (e.g., affecting control capabilities of the vehicle 100). Additionally or alternatively, the sensors and systems may be part of one or more advanced driver assistance systems (ADAS) associated with a vehicle 100. In any event, the sensors and systems may be used to provide driving assistance at any level of operation (e.g., from fully-manual to fully-autonomous operations, etc.) as described herein.

The various levels of vehicle control and/or operation can be described as corresponding to a level of autonomy associated with a vehicle 100 for vehicle driving operations. For instance, at Level 0, or fully-manual driving operations, a driver (e.g., a human driver) may be responsible for all the driving control operations (e.g., steering, accelerating, braking, etc.) associated with the vehicle. Level 0 may be referred to as a "No Automation" level. At Level 1, the vehicle may be responsible for a limited number of the driving operations associated with the vehicle, while the driver is still responsible for most driving control operations. An example of a Level 1 vehicle may include a vehicle in which the throttle control and/or braking operations may be controlled by the vehicle (e.g., cruise control operations, etc.). Level 1 may be referred to as a "Driver Assistance" level. At Level 2, the vehicle may collect information (e.g., via one or more driving assistance systems, sensors, etc.) about an environment of the vehicle (e.g., surrounding area, roadway, traffic, ambient conditions, etc.) and use the collected information to control driving operations (e.g., steering, accelerating, braking, etc.) associated with the vehicle. In a Level 2 autonomous vehicle, the driver may be required to perform other aspects of driving operations not controlled by the vehicle. Level 2 may be referred to as a "Partial Automation" level. It should be appreciated that Levels 0-2 all involve the driver monitoring the driving operations of the vehicle.

At Level 3, the driver may be separated from controlling all the driving operations of the vehicle except when the vehicle makes a request for the operator to act or intervene in controlling one or more driving operations. In other words, the driver may be separated from controlling the vehicle unless the driver is required to take over for the vehicle. Level 3 may be referred to as a "Conditional Automation" level. At Level 4, the driver may be separated from controlling all the driving operations of the vehicle and the vehicle may control driving operations even when a user fails to respond to a request to intervene. Level 4 may be referred to as a "High Automation" level. At Level 5, the vehicle can control all the driving operations associated with the vehicle in all driving modes. The vehicle in Level 5 may continually monitor traffic, vehicular, roadway, and/or environmental conditions while driving the vehicle. In Level 5, there is no human driver interaction required in any driving mode. Accordingly, Level 5 may be referred to as a "Full Automation" level. It should be appreciated that in Levels 3-5 the vehicle, and/or one or more automated driving systems associated with the vehicle, monitors the driving operations of the vehicle and the driving environment.

As shown in FIG. 1, the vehicle 100 may, for example, include at least one of a ranging and imaging system 112 (e.g., LIDAR, etc.), an imaging sensor 116A, 116F (e.g., camera, IR, etc.), a radio object-detection and ranging system sensors 116B (e.g., RADAR, RF, etc.), ultrasonic sensors 116C, and/or other object-detection sensors 116D, 116E. In some embodiments, the LIDAR system 112 and/or sensors may be mounted on a roof 130 of the vehicle 100. In one embodiment, the RADAR sensors 116B may be disposed at least at a front 110, aft 120, or side 160 of the vehicle 100. Among other things, the RADAR sensors may be used to monitor and/or detect a position of other vehicles, pedestrians, and/or other objects near, or proximal to, the vehicle 100. While shown associated with one or more areas of a vehicle 100, it should be appreciated that any of the sensors and systems 116A-K, 112 illustrated in FIGS. 1 and 2 may be disposed in, on, and/or about the vehicle 100 in any position, area, and/or zone of the vehicle 100.

Figure 2:
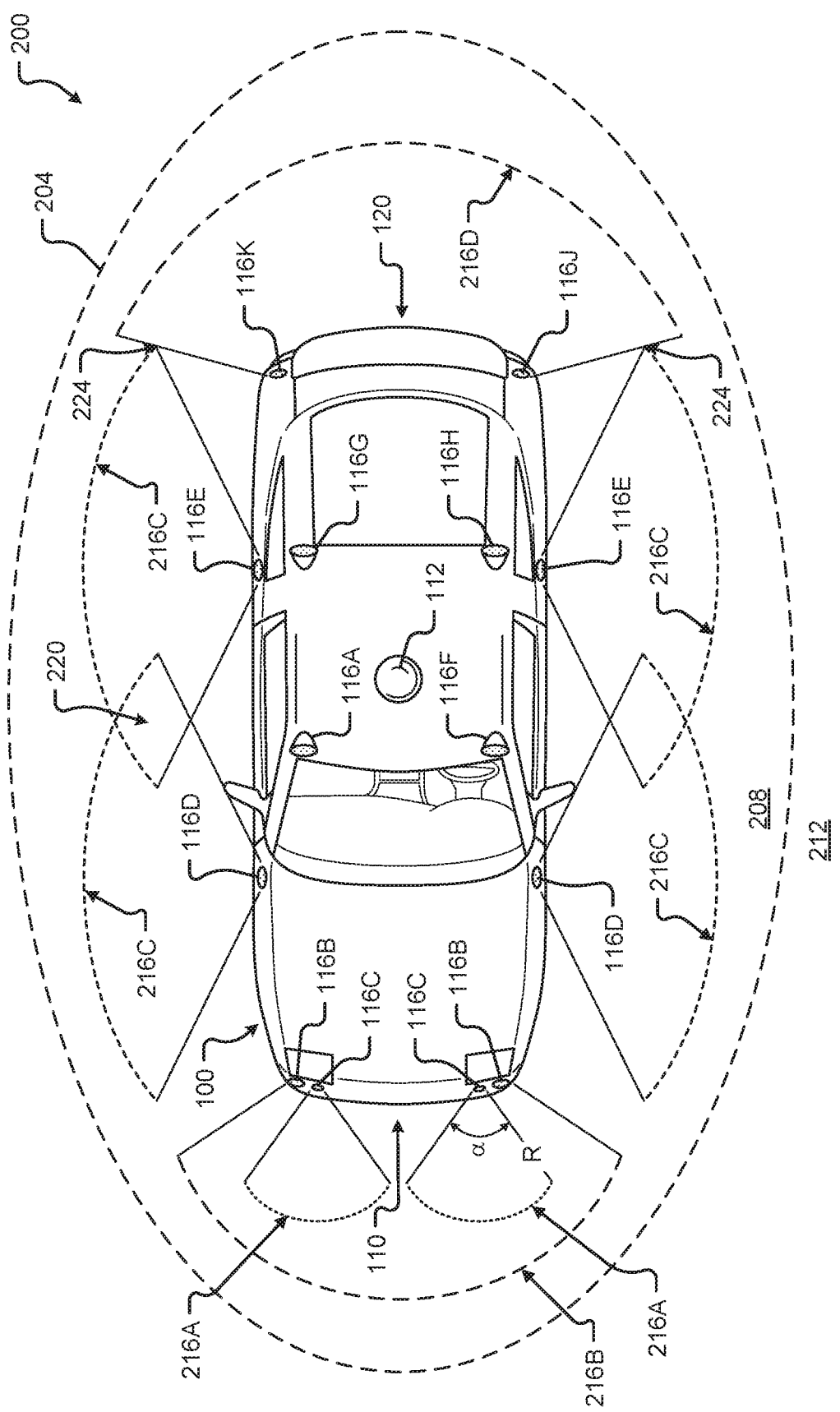
FIG. 2 shows a plan view of the vehicle in accordance with at least some embodiments of the present disclosure.

Referring now to FIG. 2, a plan view of a vehicle 100 will be described in accordance with embodiments of the present disclosure. In particular, FIG. 2 shows a vehicle sensing environment 200 at least partially defined by the sensors and systems 116A-K, 112 disposed in, on, and/or about the vehicle 100. Each sensor 116A-K may include an operational detection range R and operational detection angle. The operational detection range R may define the effective detection limit, or distance, of the sensor 116A-K. In some cases, this effective detection limit may be defined as a distance from a portion of the sensor 116A-K (e.g., a lens, sensing surface, etc.) to a point in space offset from the sensor 116A-K. The effective detection limit may define a distance, beyond which, the sensing capabilities of the sensor 116A-K deteriorate, fail to work, or are unreliable. In some embodiments, the effective detection limit may define a distance, within which, the sensing capabilities of the sensor 116A-K are able to provide accurate and/or reliable detection information. The operational detection angle may define at least one angle of a span, or between horizontal and/or vertical limits, of a sensor 116A-K. As can be appreciated, the operational detection limit and the operational detection angle of a sensor 116A-K together may define the effective detection zone 216A-D (e.g., the effective detection area, and/or volume, etc.) of a sensor 116A-K.

In some embodiments, the vehicle 100 may include a ranging and imaging system 112 such as LIDAR, or the like. The ranging and imaging system 112 may be configured to detect visual information in an environment surrounding the vehicle 100. The visual information detected in the environment surrounding the ranging and imaging system 112 may be processed (e.g., via one or more sensor and/or system processors, etc.) to generate a complete 360-degree view of an environment 200 around the vehicle. The ranging and imaging system 112 may be configured to generate changing 360-degree views of the environment 200 in real-time, for instance, as the vehicle 100 drives. In some cases, the ranging and imaging system 112 may have an effective detection limit 204 that is some distance from the center of the vehicle 100 outward over 360 degrees. The effective detection limit 204 of the ranging and imaging system 112 defines a view zone 208 (e.g., an area and/or volume, etc.) surrounding the vehicle 100. Any object falling outside of the view zone 208 is in the undetected zone 212 and would not be detected by the ranging and imaging system 112 of the vehicle 100.

Sensor data and information may be collected by one or more sensors or systems 116A-K, 112 of the vehicle 100 monitoring the vehicle sensing environment 200. This information may be processed (e.g., via a processor, computer-vision system, etc.) to determine targets (e.g., objects, signs, people, markings, roadways, conditions, etc.) inside one or more detection zones 208, 216A-D associated with the vehicle sensing environment 200. In some cases, information from multiple sensors 116A-K may be processed to form composite sensor detection information. For example, a first sensor 116A and a second sensor 116F may correspond to a first camera 116A and a second camera 116F aimed in a forward traveling direction of the vehicle 100. In this example, images collected by the cameras 116A, 116F may be combined to form stereo image information. This composite information may increase the capabilities of a single sensor in the one or more sensors 116A-K by, for example, adding the ability to determine depth associated with targets in the one or more detection zones 208, 216A-D. Similar image data may be collected by rear view cameras (e.g., sensors 116G, 116H) aimed in a rearward traveling direction vehicle 100.

In some embodiments, multiple sensors 116A-K may be effectively joined to increase a sensing zone and provide increased sensing coverage. For instance, multiple RADAR sensors 116B disposed on the front 110 of the vehicle may be joined to provide a zone 216B of coverage that spans across an entirety of the front 110 of the vehicle. In some cases, the multiple RADAR sensors 116B may cover a detection zone 216B that includes one or more other sensor detection zones 216A. These overlapping detection zones may provide redundant sensing, enhanced sensing, and/or provide greater detail in sensing within a particular portion (e.g., zone 216A) of a larger zone (e.g., zone 216B). Additionally or alternatively, the sensors 116A-K of the vehicle 100 may be arranged to create a complete coverage, via one or more sensing zones 208, 216A-D around the vehicle 100. In some areas, the sensing zones 216C of two or more sensors 116D, 116E may intersect at an overlap zone 220. In some areas, the angle and/or detection limit of two or more sensing zones 216C, 216D (e.g., of two or more sensors 116E, 116J, 116K) may meet at a virtual intersection point 224.

The vehicle 100 may include a number of sensors 116E, 116G, 116H, 116J, 116K disposed proximal to the rear 120 of the vehicle 100. These sensors can include, but are in no way limited to, an imaging sensor, camera, IR, a radio object-detection and ranging sensors, RADAR, RF, ultrasonic sensors, and/or other object-detection sensors. Among other things, these sensors 116E, 116G, 116H, 116J, 116K may detect targets near or approaching the rear of the vehicle 100. For example, another vehicle approaching the rear 120 of the vehicle 100 may be detected by one or more of the ranging and imaging system (e.g., LIDAR) 112, rear-view cameras 116G, 116H, and/or rear facing RADAR sensors 116J, 116K. As described above, the images from the rear-view cameras 116G, 116H may be processed to generate a stereo view (e.g., providing depth associated with an object or environment, etc.) for targets visible to both cameras 116G, 116H. As another example, the vehicle 100 may be driving and one or more of the ranging and imaging system 112, front-facing cameras 116A, 116F, front-facing RADAR sensors 116B, and/or ultrasonic sensors 116C may detect targets in front of the vehicle 100. This approach may provide critical sensor information to a vehicle control system in at least one of the autonomous driving levels described above. For instance, when the vehicle 100 is driving autonomously (e.g., Level 3, Level 4, or Level 5) and detects other vehicles stopped in a travel path, the sensor detection information may be sent to the vehicle control system of the vehicle 100 to control a driving operation (e.g., braking, decelerating, etc.) associated with the vehicle 100 (in this example, slowing the vehicle 100 as to avoid colliding with the stopped other vehicles). As yet another example, the vehicle 100 may be operating and one or more of the ranging and imaging system 112, and/or the side-facing sensors 116D, 116E (e.g., RADAR, ultrasonic, camera, combinations thereof, and/or other type of sensor), may detect targets at a side of the vehicle 100. It should be appreciated that the sensors 116A-K may detect a target that is both at a side 160 and a front 110 of the vehicle 100 (e.g., disposed at a diagonal angle to a centerline of the vehicle 100 running from the front 110 of the vehicle 100 to the rear 120 of the vehicle). Additionally or alternatively, the sensors 116A-K may detect a target that is both, or simultaneously, at a side 160 and a rear 120 of the vehicle 100 (e.g., disposed at a diagonal angle to the centerline of the vehicle 100).

Figure 3A:
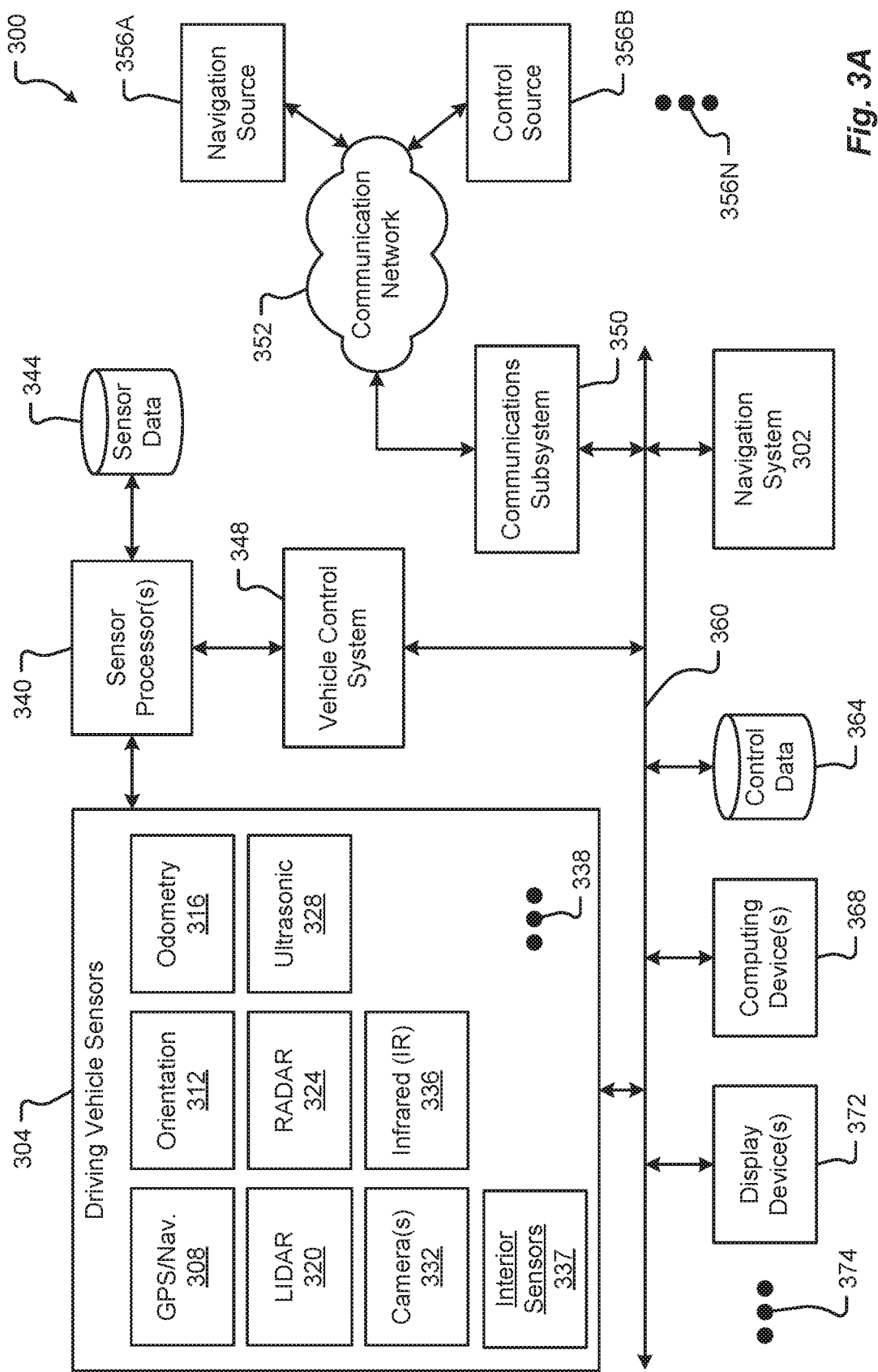
FIG. 3A is a block diagram of an embodiment of a communication environment of the vehicle in accordance with embodiments of the present disclosure.
Figure 3B:
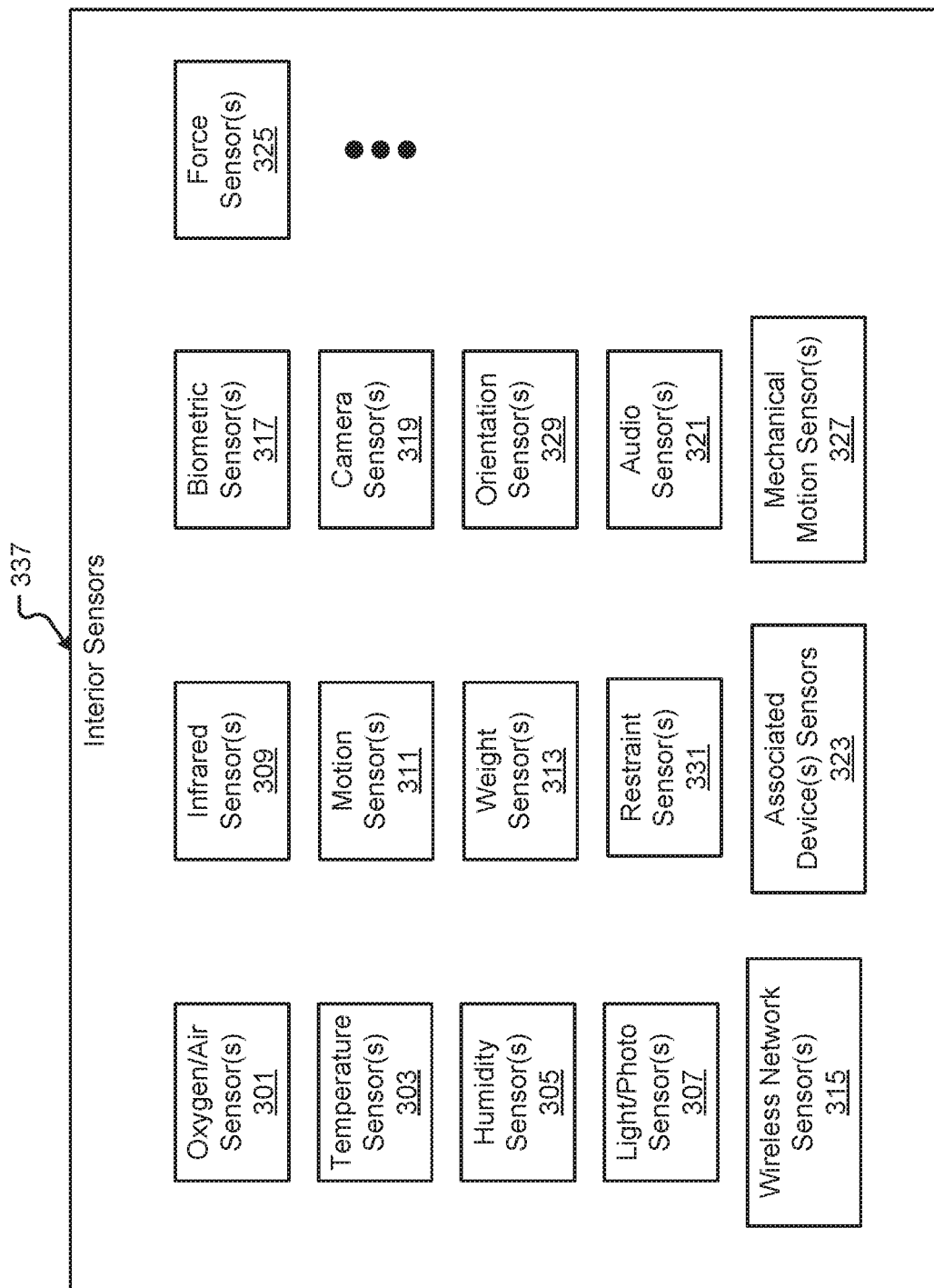
FIG. 3B is a block diagram of an embodiment of interior sensors within the vehicle in accordance with embodiments of the present disclosure.

FIGS. 3A-3C are block diagrams of an embodiment of a communication environment 300 of the vehicle 100 in accordance with embodiments of the present disclosure. The communication system 300 may include one or more vehicle driving vehicle sensors and systems 304, sensor processors 340, sensor data memory 344, vehicle control system 348, communications subsystem 350, control data 364, computing devices 368, display devices 372, and other components 374 that may be associated with a vehicle 100. These associated components may be electrically and/or communicatively coupled to one another via at least one bus 360. In some embodiments, the one or more associated components may send and/or receive signals across a communication network 352 to at least one of a navigation source 356A, a control source 356B, or some other entity 356N.

In accordance with at least some embodiments of the present disclosure, the communication network 352 may comprise any type of known communication medium or collection of communication media and may use any type of protocols, such as SIP, TCP/IP, SNA, IPX, AppleTalk, and the like, to transport messages between endpoints. The communication network 352 may include wired and/or wireless communication technologies. The Internet is an example of the communication network 352 that constitutes an Internet Protocol (IP) network consisting of many computers, computing networks, and other communication devices located all over the world, which are connected through many telephone systems and other means. Other examples of the communication network 352 include, without limitation, a standard Plain Old Telephone System (POTS), an Integrated Services Digital Network (ISDN), the Public Switched Telephone Network (PSTN), a Local Area Network (LAN), such as an Ethernet network, a Token-Ring network and/or the like, a Wide Area Network (WAN), a virtual network, including without limitation a virtual private network ("VPN"); the Internet, an intranet, an extranet, a cellular network, an infra-red network; a wireless network (e.g., a network operating under any of the IEEE 802.9 suite of protocols, the Bluetooth® protocol known in the art, and/or any other wireless protocol), and any other type of packet-switched or circuit-switched network known in the art and/or any combination of these and/or other networks. In addition, it can be appreciated that the communication network 352 need not be limited to any one network type, and instead may be comprised of a number of different networks and/or network types. The communication network 352 may comprise a number of different communication media such as coaxial cable, copper cable/wire, fiber-optic cable, antennas for transmitting/receiving wireless messages, and combinations thereof.

The driving vehicle sensors and systems 304 may include at least one navigation 308 (e.g., global positioning system (GPS), etc.), orientation 312, odometry 316, LIDAR 320, RADAR 324, ultrasonic 328, camera 332, infrared (IR) 336, and/or other sensor or system 338. These driving vehicle sensors and systems 304 may be similar, if not identical, to the sensors and systems 116A-K, 112 described in conjunction with FIGS. 1 and 2.

The navigation sensor 308 may include one or more sensors having receivers and antennas that are configured to utilize a satellite-based navigation system including a network of navigation satellites capable of providing geolocation and time information to at least one component of the vehicle 100. Examples of the navigation sensor 308 as described herein may include, but are not limited to, at least one of Garmin® GLO™ family of GPS and GLONASS combination sensors, Garmin® GPS 15x™ family of sensors, Garmin® GPS 16x™ family of sensors with high-sensitivity receiver and antenna, Garmin® GPS 18x OEM family of high-sensitivity GPS sensors, Dewetron DEWE-VGPS series of GPS sensors, GlobalSat 1-Hz series of GPS sensors, other industry-equivalent navigation sensors and/or systems, and may perform navigational and/or geolocation functions using any known or future-developed standard and/or architecture.

The orientation sensor 312 may include one or more sensors configured to determine an orientation of the vehicle 100 relative to at least one reference point. In some embodiments, the orientation sensor 312 may include at least one pressure transducer, stress/strain gauge, accelerometer, gyroscope, and/or geomagnetic sensor. Examples of the navigation sensor 308 as described herein may include, but are not limited to, at least one of Bosch Sensortec BMX 160 series low-power absolute orientation sensors, Bosch Sensortec BMX055 9-axis sensors, Bosch Sensortec BMI055 6-axis inertial sensors, Bosch Sensortec BMI160 6-axis inertial sensors, Bosch Sensortec BMF055 9-axis inertial sensors (accelerometer, gyroscope, and magnetometer) with integrated Cortex M0+ microcontroller, Bosch Sensortec BMP280 absolute barometric pressure sensors, Infineon TLV493D-A1B6 3D magnetic sensors, Infineon TLI493D-W1B6 3D magnetic sensors, Infineon TL family of 3D magnetic sensors, Murata Electronics SCC2000 series combined gyro sensor and accelerometer, Murata Electronics SCC1300 series combined gyro sensor and accelerometer, other industry-equivalent orientation sensors and/or systems, which may perform orientation detection and/or determination functions using any known or future-developed standard and/or architecture.

The odometry sensor and/or system 316 may include one or more components that is configured to determine a change in position of the vehicle 100 over time. In some embodiments, the odometry system 316 may utilize data from one or more other sensors and/or systems 304 in determining a position (e.g., distance, location, etc.) of the vehicle 100 relative to a previously measured position for the vehicle 100. Additionally or alternatively, the odometry sensors 316 may include one or more encoders, Hall speed sensors, and/or other measurement sensors/devices configured to measure a wheel speed, rotation, and/or number of revolutions made over time. Examples of the odometry sensor/system 316 as described herein may include, but are not limited to, at least one of Infineon TLE4924/26/27/28C high-performance speed sensors, Infineon TL4941plusC(B) single chip differential Hall wheel-speed sensors, Infineon TL5041plusC Giant Magnetoresistance (GMR) effect sensors, Infineon TL family of magnetic sensors, EPC Model 25SP Accu-CoderPro™ incremental shaft encoders, EPC Model 30M compact incremental encoders with advanced magnetic sensing and signal processing technology, EPC Model 925 absolute shaft encoders, EPC Model 958 absolute shaft encoders, EPC Model MA36S/MA63S/SA36S absolute shaft encoders, Dynapar™ F18 commutating optical encoder, Dynapar™ HS35R family of phased array encoder sensors, other industry-equivalent odometry sensors and/or systems, and may perform change in position detection and/or determination functions using any known or future-developed standard and/or architecture.

The LIDAR sensor/system 320 may include one or more components configured to measure distances to targets using laser illumination. In some embodiments, the LIDAR sensor/system 320 may provide 3D imaging data of an environment around the vehicle 100. The imaging data may be processed to generate a full 360-degree view of the environment around the vehicle 100. The LIDAR sensor/system 320 may include a laser light generator configured to generate a plurality of target illumination laser beams (e.g., laser light channels). In some embodiments, this plurality of laser beams may be aimed at, or directed to, a rotating reflective surface (e.g., a mirror) and guided outwardly from the LIDAR sensor/system 320 into a measurement environment. The rotating reflective surface may be configured to continually rotate 360 degrees about an axis, such that the plurality of laser beams is directed in a full 360-degree range around the vehicle 100. A photodiode receiver of the LIDAR sensor/system 320 may detect when light from the plurality of laser beams emitted into the measurement environment returns (e.g., reflected echo) to the LIDAR sensor/system 320. The LIDAR sensor/system 320 may calculate, based on a time associated with the emission of light to the detected return of light, a distance from the vehicle 100 to the illuminated target. In some embodiments, the LIDAR sensor/system 320 may generate over 2.0 million points per second and have an effective operational range of at least 100 meters. Examples of the LIDAR sensor/system 320 as described herein may include, but are not limited to, at least one of Velodyne® LiDAR™ HDL-64E 64-channel LIDAR sensors, Velodyne® LiDAR™ HDL-32E 32-channel LIDAR sensors, Velodyne® LiDAR™ PUCK™ VLP-16 16-channel LIDAR sensors, Leica Geosystems Pegasus: Two mobile sensor platform, Garmin® LIDAR-Lite v3 measurement sensor, Quanergy M8 LiDAR sensors, Quanergy S3 solid state LiDAR sensor, LeddarTech® LeddarVU compact solid state fixed-beam LIDAR sensors, other industry-equivalent LIDAR sensors and/or systems, and may perform illuminated target and/or obstacle detection in an environment around the vehicle 100 using any known or future-developed standard and/or architecture.

The RADAR sensors 324 may include one or more radio components that are configured to detect objects/targets in an environment of the vehicle 100. In some embodiments, the RADAR sensors 324 may determine a distance, position, and/or movement vector (e.g., angle, speed, etc.) associated with a target over time. The RADAR sensors 324 may include a transmitter configured to generate and emit electromagnetic waves (e.g., radio, microwaves, etc.) and a receiver configured to detect returned electromagnetic waves. In some embodiments, the RADAR sensors 324 may include at least one processor configured to interpret the returned electromagnetic waves and determine locational properties of targets. Examples of the RADAR sensors 324 as described herein may include, but are not limited to, at least one of Infineon RASIC™ RTN7735PL transmitter and RRN7745PL/46PL receiver sensors, Autoliv ASP Vehicle RADAR sensors, Delphi L2C0051TR 77 GHz ESR Electronically Scanning Radar sensors, Fujitsu Ten Ltd. Automotive Compact 77 GHz 3D Electronic Scan Millimeter Wave Radar sensors, other industry-equivalent RADAR sensors and/or systems, and may perform radio target and/or obstacle detection in an environment around the vehicle 100 using any known or future-developed standard and/or architecture.

The ultrasonic sensors 328 may include one or more components that are configured to detect objects/targets in an environment of the vehicle 100. In some embodiments, the ultrasonic sensors 328 may determine a distance, position, and/or movement vector (e.g., angle, speed, etc.) associated with a target over time. The ultrasonic sensors 328 may include an ultrasonic transmitter and receiver, or transceiver, configured to generate and emit ultrasound waves and interpret returned echoes of those waves. In some embodiments, the ultrasonic sensors 328 may include at least one processor configured to interpret the returned ultrasonic waves and determine locational properties of targets. Examples of the ultrasonic sensors 328 as described herein may include, but are not limited to, at least one of Texas Instruments TIDA-00151 automotive ultrasonic sensor interface IC sensors, MaxBotix® MB8450 ultrasonic proximity sensor, MaxBotix® ParkSonar™-EZ ultrasonic proximity sensors, Murata Electronics MA40H1S-R open-structure ultrasonic sensors, Murata Electronics MA40S4R/S open-structure ultrasonic sensors, Murata Electronics MA58MF14-7N waterproof ultrasonic sensors, other industry-equivalent ultrasonic sensors and/or systems, and may perform ultrasonic target and/or obstacle detection in an environment around the vehicle 100 using any known or future-developed standard and/or architecture.

The camera sensors 332 may include one or more components configured to detect image information associated with an environment of the vehicle 100. In some embodiments, the camera sensors 332 may include a lens, filter, image sensor, and/or a digital image processer. It is an aspect of the present disclosure that multiple camera sensors 332 may be used together to generate stereo images providing depth measurements. Examples of the camera sensors 332 as described herein may include, but are not limited to, at least one of ON Semiconductor® MT9V024 Global Shutter VGA GS CMOS image sensors, Teledyne DALSA Falcon2 camera sensors, CMOSIS CMV50000 high-speed CMOS image sensors, other industry-equivalent camera sensors and/or systems, and may perform visual target and/or obstacle detection in an environment around the vehicle 100 using any known or future-developed standard and/or architecture.

The infrared (IR) sensors 336 may include one or more components configured to detect image information associated with an environment of the vehicle 100. The IR sensors 336 may be configured to detect targets in low-light, dark, or poorly-lit environments. The IR sensors 336 may include an IR light emitting element (e.g., IR light emitting diode (LED), etc.) and an IR photodiode. In some embodiments, the IR photodiode may be configured to detect returned IR light at or about the same wavelength to that emitted by the IR light emitting element. In some embodiments, the IR sensors 336 may include at least one processor configured to interpret the returned IR light and determine locational properties of targets. The IR sensors 336 may be configured to detect and/or measure a temperature associated with a target (e.g., an object, pedestrian, other vehicle, etc.). Examples of IR sensors 336 as described herein may include, but are not limited to, at least one of Opto Diode lead-salt IR array sensors, Opto Diode OD-850 Near-IR LED sensors, Opto Diode SA/SHA727 steady state IR emitters and IR detectors, FLIR® $L_5$ microbolometer sensors, FLIR® TacFLIR 380-HD InSb MWIR FPA and HD MWIR thermal sensors, FLIR® VOx 640×480 pixel detector sensors, Delphi IR sensors, other industry-equivalent IR sensors and/or systems, and may perform IR visual target and/or obstacle detection in an environment around the vehicle 100 using any known or future-developed standard and/or architecture.

The vehicle 100 can also include one or more interior sensors 337. Interior sensors 337 can measure characteristics of the inside environment of the vehicle 100. The interior sensors 337 may be as described in conjunction with FIG. 3B.

A navigation system 302 can include any hardware and/or software used to navigate the vehicle either manually or autonomously. The navigation system 302 may be as described in conjunction with FIG. 3C.

In some embodiments, the driving vehicle sensors and systems 304 may include other sensors 338 and/or combinations of the sensors 306-337 described above. Additionally or alternatively, one or more of the sensors 306-337 described above may include one or more processors configured to process and/or interpret signals detected by the one or more sensors 306-337. In some embodiments, the processing of at least some sensor information provided by the vehicle sensors and systems 304 may be processed by at least one sensor processor 340. Raw and/or processed sensor data may be stored in a sensor data memory 344 storage medium. In some embodiments, the sensor data memory 344 may store instructions used by the sensor processor 340 for processing sensor information provided by the sensors and systems 304. In any event, the sensor data memory 344 may be a disk drive, optical storage device, solid-state storage device such as a random access memory ("RAM") and/or a read-only memory ("ROM"), which can be programmable, flash-updateable, and/or the like.

The vehicle control system 348 may receive processed sensor information from the sensor processor 340 and determine to control an aspect of the vehicle 100. Controlling an aspect of the vehicle 100 may include presenting information via one or more display devices 372 associated with the vehicle, sending commands to one or more computing devices 368 associated with the vehicle, and/or controlling a driving operation of the vehicle. In some embodiments, the vehicle control system 348 may correspond to one or more computing systems that control driving operations of the vehicle 100 in accordance with the Levels of driving autonomy described above. In one embodiment, the vehicle control system 348 may operate a speed of the vehicle 100 by controlling an output signal to the accelerator and/or braking system of the vehicle. In this example, the vehicle control system 348 may receive sensor data describing an environment surrounding the vehicle 100 and, based on the sensor data received, determine to adjust the acceleration, power output, and/or braking of the vehicle 100. The vehicle control system 348 may additionally control steering and/or other driving functions of the vehicle 100.

The vehicle control system 348 may communicate, in real-time, with the driving sensors and systems 304 forming a feedback loop. In particular, upon receiving sensor information describing a condition of targets in the environment surrounding the vehicle 100, the vehicle control system 348 may autonomously make changes to a driving operation of the vehicle 100. The vehicle control system 348 may then receive subsequent sensor information describing any change to the condition of the targets detected in the environment as a result of the changes made to the driving operation. This continual cycle of observation (e.g., via the sensors, etc.) and action (e.g., selected control or non-control of vehicle operations, etc.) allows the vehicle 100 to operate autonomously in the environment.

In some embodiments, the one or more components of the vehicle 100 (e.g., the driving vehicle sensors 304, vehicle control system 348, display devices 372, etc.) may communicate across the communication network 352 to one or more entities 356A-N via a communications subsystem 350 of the vehicle 100. Embodiments of the communications subsystem 350 are described in greater detail in conjunction with FIG. 5. For instance, the navigation sensors 308 may receive global positioning, location, and/or navigational information from a navigation source 356A. In some embodiments, the navigation source 356A may be a global navigation satellite system (GNSS) similar, if not identical, to NAVSTAR GPS, GLONASS, EU Galileo, and/or the BeiDou Navigation Satellite System (BDS) to name a few.

In some embodiments, the vehicle control system 348 may receive control information from one or more control sources 356B. The control source 356 may provide vehicle control information including autonomous driving control commands, vehicle operation override control commands, and the like. The control source 356 may correspond to an autonomous vehicle control system, a traffic control system, an administrative control entity, and/or some other controlling server. It is an aspect of the present disclosure that the vehicle control system 348 and/or other components of the vehicle 100 may exchange communications with the control source 356 across the communication network 352 and via the communications subsystem 350.

Information associated with controlling driving operations of the vehicle 100 may be stored in a control data memory 364 storage medium. The control data memory 364 may store instructions used by the vehicle control system 348 for controlling driving operations of the vehicle 100, historical control information, autonomous driving control rules, and the like. In some embodiments, the control data memory 364 may be a disk drive, optical storage device, solid-state storage device such as a random access memory ("RAM") and/or a read-only memory ("ROM"), which can be programmable, flash-updateable, and/or the like.

In L4 or L5 automation, the vehicle control subsystem 348 controls the driving behavior of the vehicle in response to the current vehicle location, sensed exterior animate and inanimate object information, sensed occupant information of the vehicle, vehicle-related information of the vehicle, exterior environmental information, and navigation information (e.g., from a cloud source such as Google Maps™). In a typical implementation, the autonomous driving agent, based on feedback from certain sensors, specifically the LIDAR and radar sensors positioned around the circumference of the vehicle, constructs a three-dimensional map in spatial proximity to the vehicle that enables the vehicle control subsystem 348 to identify and spatially locate animate and inanimate objects. Other sensors, such as inertial measurement units, gyroscopes, wheel encoders, sonar sensors, motion sensors to perform odometry calculations with respect to nearby moving objects, and exterior facing cameras (e.g., to perform computer vision processing) can provide further contextual information for generation of a more accurate three-dimensional map. The navigation information is combined with the three-dimensional map to provide short, intermediate and long range course tracking and route selection. The vehicle control subsystem 348 processes real-world information as well as GPS data, and driving speed to determine accurately the precise position of each vehicle, down to a few centimeters all while making corrections for nearby animate and inanimate objects.

The vehicle control subsystem 348 processes in real time the aggregate mapping information and models behavior of occupants of the current vehicle and other nearby animate objects and issues appropriate commands regarding vehicle operation. While some commands are hard-coded into the vehicle, such as stopping at red lights and stop signs, other responses are learned and recorded by profile updates based on previous driving experiences. Examples of learned behavior include a slow-moving or stopped vehicle or emergency vehicle in a right lane suggests a higher probability that the car following it will attempt to pass, a pot hole, rock, or other foreign object in the roadway equates to a higher probability that a driver will swerve to avoid it, and traffic congestion in one lane means that other drivers moving in the same direction will have a higher probability of passing in an adjacent lane or by driving on the shoulder.

In addition to the mechanical components described herein, the vehicle 100 may include a number of user interface devices. The user interface devices receive and translate human input into a mechanical movement or electrical signal or stimulus. The human input may be one or more of motion (e.g., body movement, body part movement, in two-dimensional or three-dimensional space, etc.), voice, touch, and/or physical interaction with the components of the vehicle 100. In some embodiments, the human input may be configured to control one or more functions of the vehicle 100 and/or systems of the vehicle 100 described herein. User interfaces may include, but are in no way limited to, at least one graphical user interface of a display device, steering wheel or mechanism, transmission lever or button (e.g., including park, neutral, reverse, and/or drive positions, etc.), throttle control pedal or mechanism, brake control pedal or mechanism, power control switch, communications equipment, etc.

FIG. 3B shows a block diagram of an embodiment of interior sensors 337 for a vehicle 100. The interior sensors 337 may be arranged into one or more groups, based at least partially on the function of the interior sensors 337. For example, the interior space of a vehicle 100 may include environmental sensors, user interface sensor(s), and/or safety sensors. Additionally or alternatively, there may be sensors associated with various devices inside the vehicle (e.g., smart phones, tablets, mobile computers, wearables, etc.)

Environmental sensors may comprise sensors configured to collect data relating to the internal environment of a vehicle 100. Examples of environmental sensors may include one or more of, but are not limited to: oxygen/air sensors 301, temperature sensors 303, humidity sensors 305, light/photo sensors 307, and more. The oxygen/air sensors 301 may be configured to detect a quality or characteristic of the air in the interior space 108 of the vehicle 100 (e.g., ratios and/or types of gasses comprising the air inside the vehicle 100, dangerous gas levels, safe gas levels, etc.). Temperature sensors 303 may be configured to detect temperature readings of one or more objects, users 216, and/or areas of a vehicle 100. Humidity sensors 305 may detect an amount of water vapor present in the air inside the vehicle 100. The light/photo sensors 307 can detect an amount of light present in the vehicle 100. Further, the light/photo sensors 307 may be configured to detect various levels of light intensity associated with light in the vehicle 100.

User interface sensors may comprise sensors configured to collect data relating to one or more users (e.g., a driver and/or passenger(s)) in a vehicle 100. As can be appreciated, the user interface sensors may include sensors that are configured to collect data from users 216 in one or more areas of the vehicle 100. Examples of user interface sensors may include one or more of, but are not limited to: infrared sensors 309, motion sensors 311, weight sensors 313, wireless network sensors 315, biometric sensors 317, camera (or image) sensors 319, audio sensors 321, and more.

Infrared sensors 309 may be used to measure IR light irradiating from at least one surface, user, or other object in the vehicle 100. Among other things, the Infrared sensors 309 may be used to measure temperatures, form images (especially in low light conditions), identify users 216, and even detect motion in the vehicle 100.

The motion sensors 311 may detect motion and/or movement of objects inside the vehicle 100. Optionally, the motion sensors 311 may be used alone or in combination to detect movement. For example, a user may be operating a vehicle 100 (e.g., while driving, etc.) when a passenger in the rear of the vehicle 100 unbuckles a safety belt and proceeds to move about the vehicle 10. In this example, the movement of the passenger could be detected by the motion sensors 311. In response to detecting the movement and/or the direction associated with the movement, the passenger may be prevented from interfacing with and/or accessing at least some of the vehicle control features. As can be appreciated, the user may be alerted of the movement/motion such that the user can act to prevent the passenger from interfering with the vehicle controls. Optionally, the number of motion sensors in a vehicle may be increased to increase an accuracy associated with motion detected in the vehicle 100.

Weight sensors 313 may be employed to collect data relating to objects and/or users in various areas of the vehicle 100. In some cases, the weight sensors 313 may be included in the seats and/or floor of a vehicle 100. Optionally, the vehicle 100 may include a wireless network sensor 315. This sensor 315 may be configured to detect one or more wireless network(s) inside the vehicle 100. Examples of wireless networks may include, but are not limited to, wireless communications utilizing Bluetooth®, $W_1$-Fi™, ZigBee, IEEE 802.11, and other wireless technology standards. For example, a mobile hotspot may be detected inside the vehicle 100 via the wireless network sensor 315. In this case, the vehicle 100 may determine to utilize and/or share the mobile hotspot detected via/with one or more other devices associated with the vehicle 100.

Biometric sensors 317 may be employed to identify and/or record characteristics associated with a user. It is anticipated that biometric sensors 317 can include at least one of image sensors, IR sensors, fingerprint readers, weight sensors, load cells, force transducers, heart rate monitors, blood pressure monitors, and the like as provided herein.

The camera sensors 319 may record still images, video, and/or combinations thereof. Camera sensors 319 may be used alone or in combination to identify objects, users, and/or other features, inside the vehicle 100. Two or more camera sensors 319 may be used in combination to form, among other things, stereo and/or three-dimensional (3D) images. The stereo images can be recorded and/or used to determine depth associated with objects and/or users in a vehicle 100. Further, the camera sensors 319 used in combination may determine the complex geometry associated with identifying characteristics of a user. For example, the camera sensors 319 may be used to determine dimensions between various features of a user's face (e.g., the depth/distance from a user's nose to a user's cheeks, a linear distance between the center of a user's eyes, and more). These dimensions may be used to verify, record, and even modify characteristics that serve to identify a user. The camera sensors 319 may also be used to determine movement associated with objects and/or users within the vehicle 100. It should be appreciated that the number of image sensors used in a vehicle 100 may be increased to provide greater dimensional accuracy and/or views of a detected image in the vehicle 100.

The audio sensors 321 may be configured to receive audio input from a user of the vehicle 100. The audio input from a user may correspond to voice commands, conversations detected in the vehicle 100, phone calls made in the vehicle 100, and/or other audible expressions made in the vehicle 100. Audio sensors 321 may include, but are not limited to, microphones and other types of acoustic-to-electric transducers or sensors. Optionally, the interior audio sensors 321 may be configured to receive and convert sound waves into an equivalent analog or digital signal. The interior audio sensors 321 may serve to determine one or more locations associated with various sounds in the vehicle 100. The location of the sounds may be determined based on a comparison of volume levels, intensity, and the like, between sounds detected by two or more interior audio sensors 321. For instance, a first audio sensors 321 may be located in a first area of the vehicle 100 and a second audio sensors 321 may be located in a second area of the vehicle 100. If a sound is detected at a first volume level by the first audio sensors 321 A and a second, higher, volume level by the second audio sensors 321 in the second area of the vehicle 100, the sound may be determined to be closer to the second area of the vehicle 100. As can be appreciated, the number of sound receivers used in a vehicle 100 may be increased (e.g., more than two, etc.) to increase measurement accuracy surrounding sound detection and location, or source, of the sound (e.g., via triangulation, etc.).

The safety sensors may comprise sensors configured to collect data relating to the safety of a user and/or one or more components of a vehicle 100. Examples of safety sensors may include one or more of, but are not limited to: force sensors 325, mechanical motion sensors 327, orientation sensors 329, restraint sensors 331, and more.

The force sensors 325 may include one or more sensors inside the vehicle 100 configured to detect a force observed in the vehicle 100. One example of a force sensor 325 may include a force transducer that converts measured forces (e.g., force, weight, pressure, etc.) into output signals. Mechanical motion sensors 327 may correspond to encoders, accelerometers, damped masses, and the like. Optionally, the mechanical motion sensors 327 may be adapted to measure the force of gravity (i.e., G-force) as observed inside the vehicle 100. Measuring the G-force observed inside a vehicle 100 can provide valuable information related to a vehicle's acceleration, deceleration, collisions, and/or forces that may have been suffered by one or more users in the vehicle 100. Orientation sensors 329 can include accelerometers, gyroscopes, magnetic sensors, and the like that are configured to detect an orientation associated with the vehicle 100.

The restraint sensors 331 may correspond to sensors associated with one or more restraint devices and/or systems in a vehicle 100. Seatbelts and airbags are examples of restraint devices and/or systems. As can be appreciated, the restraint devices and/or systems may be associated with one or more sensors that are configured to detect a state of the device/system. The state may include extension, engagement, retraction, disengagement, deployment, and/or other electrical or mechanical conditions associated with the device/system.

The associated device sensors 323 can include any sensors that are associated with a device in the vehicle 100. As previously stated, typical devices may include smart phones, tablets, laptops, mobile computers, and the like. It is anticipated that the various sensors associated with these devices can be employed by the vehicle control system 348. For example, a typical smart phone can include, an image sensor, an IR sensor, audio sensor, gyroscope, accelerometer, wireless network sensor, fingerprint reader, and more. It is an aspect of the present disclosure that one or more of these associated device sensors 323 may be used by one or more subsystems of the vehicle 100.

FIG. 3C illustrates a GPS/Navigation subsystem(s) 302. The navigation subsystem(s) 302 can be any present or future-built navigation system that may use location data, for example, from the Global Positioning System (GPS), to provide navigation information or control the vehicle 100. The navigation subsystem(s) 302 can include several components, such as, one or more of, but not limited to: a GPS Antenna/receiver 331, a location module 333, a maps database 335, etc. Generally, the several components or modules 331-335 may be hardware, software, firmware, computer readable media, or combinations thereof.

A GPS Antenna/receiver 331 can be any antenna, GPS puck, and/or receiver capable of receiving signals from a GPS satellite or other navigation system. The signals may be demodulated, converted, interpreted, etc. by the GPS Antenna/receiver 331 and provided to the location module 333. Thus, the GPS Antenna/receiver 331 may convert the time signals from the GPS system and provide a location (e.g., coordinates on a map) to the location module 333. Alternatively, the location module 333 can interpret the time signals into coordinates or other location information.

The location module 333 can be the controller of the satellite navigation system designed for use in the vehicle 100. The location module 333 can acquire position data, as from the GPS Antenna/receiver 331, to locate the user or vehicle 100 on a road in the unit's map database 335. Using the road database 335, the location module 333 can give directions to other locations along roads also in the database 335. When a GPS signal is not available, the location module 333 may apply dead reckoning to estimate distance data from sensors 304 including one or more of, but not limited to, a speed sensor attached to the drive train of the vehicle 100, a gyroscope, an accelerometer, etc. Additionally or alternatively, the location module 333 may use known locations of $W_1$-Fi hotspots, cell tower data, etc. to determine the position of the vehicle 100, such as by using time difference of arrival (TDOA) and/or frequency difference of arrival (FDOA) techniques.

The maps database 335 can include any hardware and/or software to store information about maps, geographical information system (GIS) information, location information, etc. The maps database 335 can include any data definition or other structure to store the information. Generally, the maps database 335 can include a road database that may include one or more vector maps of areas of interest. Street names, street numbers, house numbers, and other information can be encoded as geographic coordinates so that the user can find some desired destination by street address. Points of interest (waypoints) can also be stored with their geographic coordinates. For example, a point of interest may include speed cameras, fuel stations, public parking, and "parked here" (or "you parked here") information. The maps database 335 may also include road or street characteristics, for example, speed limits, location of stop lights/stop signs, lane divisions, school locations, etc. The map database contents can be produced or updated by a server connected through a wireless system in communication with the Internet, even as the vehicle 100 is driven along existing streets, yielding an up-to-date map.

Figure 4:
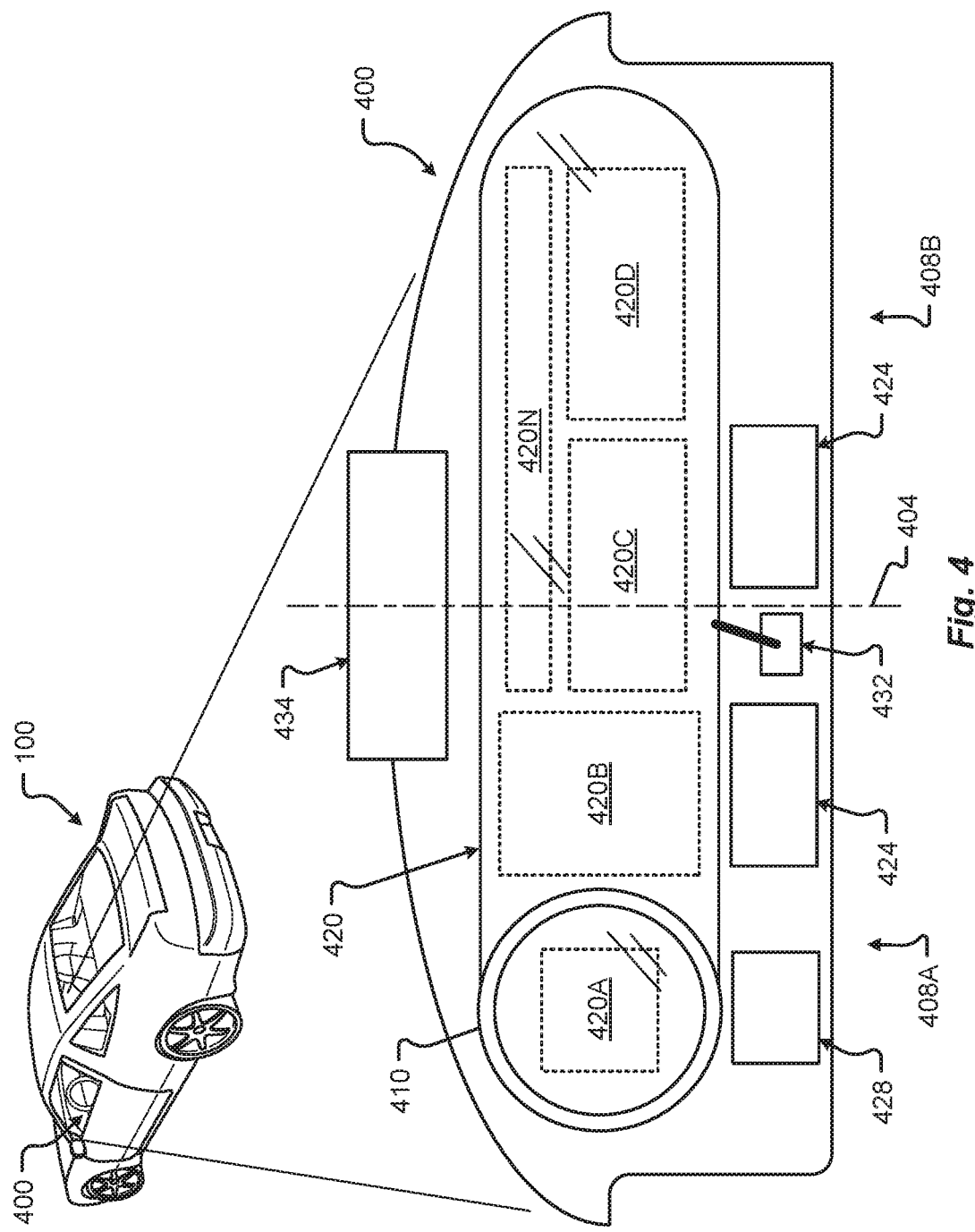
FIG. 4 shows an embodiment of the instrument panel of the vehicle according to one embodiment of the present disclosure.

FIG. 4 shows one embodiment of the instrument panel 400 of the vehicle 100. The instrument panel 400 of vehicle 100 comprises a steering wheel 410, a vehicle operational display 420 (e.g., configured to present and/or display driving data such as speed, measured air resistance, vehicle information, entertainment information, etc.), one or more auxiliary displays 424 (e.g., configured to present and/or display information segregated from the operational display 420, entertainment applications, movies, music, etc.), a heads-up display 434 (e.g., configured to display any information previously described including, but in no way limited to, guidance information such as route to destination, or obstacle warning information to warn of a potential collision, or some or all primary vehicle operational data such as speed, resistance, etc.), a power management display 428 (e.g., configured to display data corresponding to electric power levels of vehicle 100, reserve power, charging status, etc.), and an input device 432 (e.g., a controller, touchscreen, or other interface device configured to interface with one or more displays in the instrument panel or components of the vehicle 100. The input device 432 may be configured as a joystick, mouse, touchpad, tablet, 3D gesture capture device, etc.). In some embodiments, the input device 432 may be used to manually maneuver a portion of the vehicle 100 into a charging position (e.g., moving a charging plate to a desired separation distance, etc.).

While one or more of displays of instrument panel 400 may be touch-screen displays, it should be appreciated that the vehicle operational display may be a display incapable of receiving touch input. For instance, the operational display 420 that spans across an interior space centerline 404 and across both a first zone 408A and a second zone 408B may be isolated from receiving input from touch, especially from a passenger. In some cases, a display that provides vehicle operation or critical systems information and interface may be restricted from receiving touch input and/or be configured as a non-touch display. This type of configuration can prevent dangerous mistakes in providing touch input where such input may cause an accident or unwanted control.

In some embodiments, one or more displays of the instrument panel 400 may be mobile devices and/or applications residing on a mobile device such as a smart phone. Additionally or alternatively, any of the information described herein may be presented to one or more portions 420A-N of the operational display 420 or other display 424, 428, 434. In one embodiment, one or more displays of the instrument panel 400 may be physically separated or detached from the instrument panel 400. In some cases, a detachable display may remain tethered to the instrument panel.

The portions 420A-N of the operational display 420 may be dynamically reconfigured and/or resized to suit any display of information as described. Additionally or alternatively, the number of portions 420A-N used to visually present information via the operational display 420 may be dynamically increased or decreased as required, and are not limited to the configurations shown.

Figure 5:
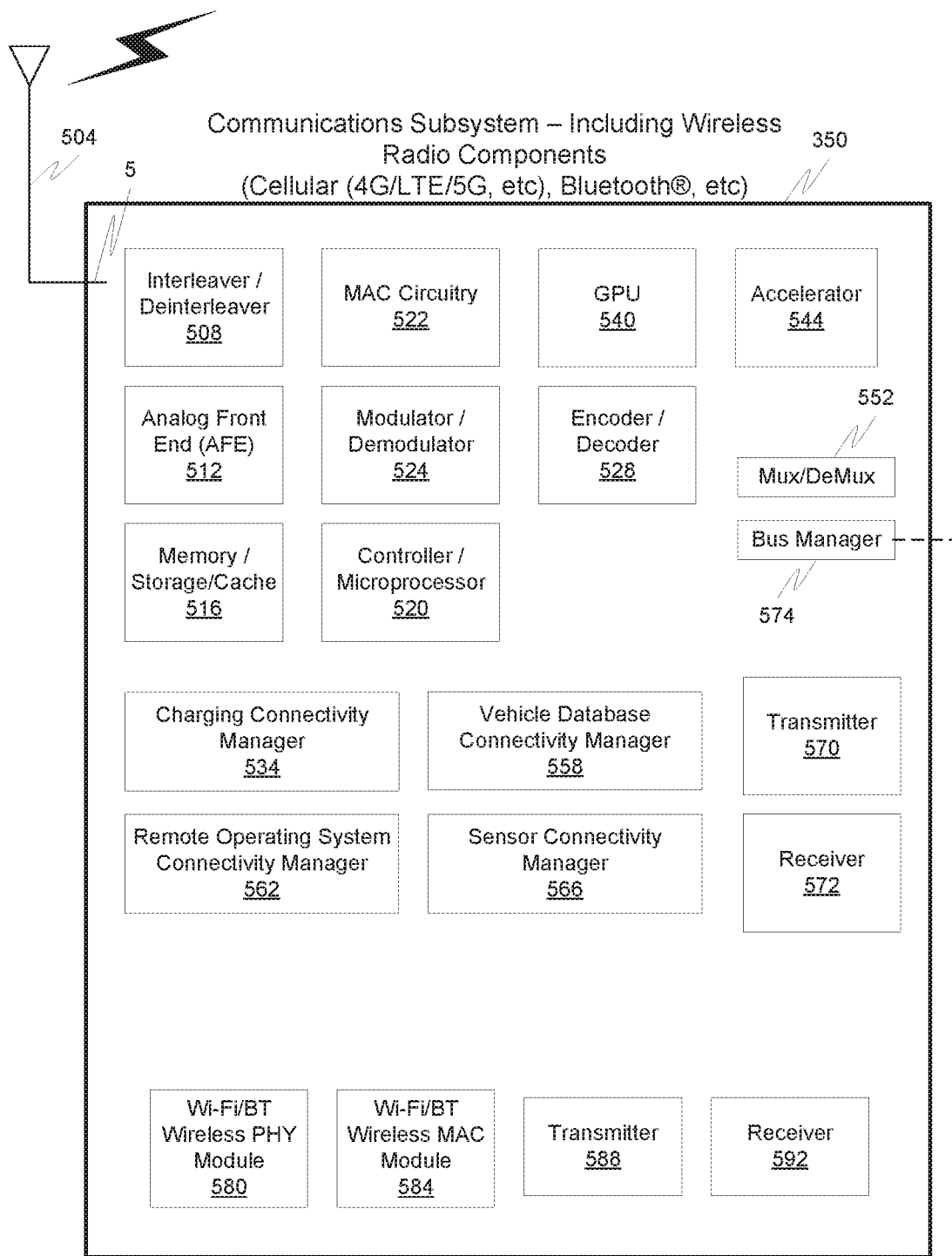
FIG. 5 is a block diagram of an embodiment of a communications subsystem of the vehicle.

FIG. 5 illustrates a hardware diagram of communications componentry that can be optionally associated with the vehicle 100 in accordance with embodiments of the present disclosure.

The communications componentry can include one or more wired or wireless devices such as a transceiver(s) and/or modem that allows communications not only between the various systems disclosed herein but also with other devices, such as devices on a network, and/or on a distributed network such as the Internet and/or in the cloud and/or with other vehicle(s).

The communications subsystem 350 can also include inter- and intra-vehicle communications capabilities such as hotspot and/or access point connectivity for any one or more of the vehicle occupants and/or vehicle-to-vehicle communications.

Additionally, and while not specifically illustrated, the communications subsystem 350 can include one or more communications links (that can be wired or wireless) and/or communications busses (managed by the bus manager 574), including one or more of CANbus, OBD-$I_1$, ARCINC 429, Byteflight, CAN (Controller Area Network), D2B (Domestic Digital Bus), FlexRay, DC-BUS, IDB-1394, IEBus, I2C, ISO 9141-1/-2, J1708, J1587, J1850, J1939, ISO 11783, Keyword Protocol 2000, LIN (Local Interconnect Network), MOST (Media Oriented Systems Transport), Multifunction Vehicle Bus, SMARTwireX, SPI, VAN (Vehicle Area Network), and the like or in general any communications protocol and/or standard(s).

The various protocols and communications can be communicated one or more of wirelessly and/or over transmission media such as single wire, twisted pair, fiber optic, IEEE 1394, MIL-STD-1553, MIL-STD-1773, power-line communication, or the like. (All of the above standards and protocols are incorporated herein by reference in their entirety).

As discussed, the communications subsystem 350 enables communications between any of the inter-vehicle systems and subsystems as well as communications with non-collocated resources, such as those reachable over a network such as the Internet.

The communications subsystem 350, in addition to well-known componentry (which has been omitted for clarity), includes interconnected elements including one or more of: one or more antennas 504, an interleaver/deinterleaver 508, an analog front end (AFE) 512, memory/storage/cache 516, controller/microprocessor 520, MAC circuitry 522, modulator/demodulator 524, encoder/decoder 528, a plurality of connectivity managers 534, 558, 562, 566, GPU 540, accelerator 544, a multiplexer/demultiplexer 552, transmitter 570, receiver 572 and additional wireless radio components such as a $W_1$-Fi PHY/Bluetooth® module 580, a $W_1$-Fi/BT MAC module 584, additional transmitter(s) 588 and additional receiver(s) 592. The various elements in the device 350 are connected by one or more links/busses 5 (not shown, again for sake of clarity).

The device 350 can have one more antennas 504, for use in wireless communications such as multi-input multi-output (MIMO) communications, multi-user multi-input multi-output (MU-MIMO) communications Bluetooth®, LTE, 4G, 5G, Near-Field Communication (NFC), etc., and in general for any type of wireless communications. The antenna(s) 504 can include, but are not limited to one or more of directional antennas, omnidirectional antennas, monopoles, patch antennas, loop antennas, microstrip antennas, dipoles, and any other antenna(s) suitable for communication transmission/reception. In an exemplary embodiment, transmission/reception using MIMO may require particular antenna spacing. In another exemplary embodiment, MIMO transmission/reception can enable spatial diversity allowing for different channel characteristics at each of the antennas. In yet another embodiment, MIMO transmission/reception can be used to distribute resources to multiple users for example within the vehicle 100 and/or in another vehicle.

Antenna(s) 504 generally interact with the Analog Front End (AFE) 512, which is needed to enable the correct processing of the received modulated signal and signal conditioning for a transmitted signal. The AFE 512 can be functionally located between the antenna and a digital baseband system in order to convert the analog signal into a digital signal for processing and vice-versa.

The subsystem 350 can also include a controller/microprocessor 520 and a memory/storage/cache 516. The subsystem 350 can interact with the memory/storage/cache 516 which may store information and operations necessary for configuring and transmitting or receiving the information described herein. The memory/storage/cache 516 may also be used in connection with the execution of application programming or instructions by the controller/microprocessor 520, and for temporary or long-term storage of program instructions and/or data. As examples, the memory/storage/cache 520 may comprise a computer-readable device, RAM, ROM, DRAM, SDRAM, and/or other storage device(s) and media.

The controller/microprocessor 520 may comprise a general purpose programmable processor or controller for executing application programming or instructions related to the subsystem 350. Furthermore, the controller/microprocessor 520 can perform operations for configuring and transmitting/receiving information as described herein. The controller/microprocessor 520 may include multiple processor cores, and/or implement multiple virtual processors. Optionally, the controller/microprocessor 520 may include multiple physical processors. By way of example, the controller/microprocessor 520 may comprise a specially configured Application Specific Integrated Circuit (ASIC) or other integrated circuit, a digital signal processor(s), a controller, a hardwired electronic or logic circuit, a programmable logic device or gate array, a special purpose computer, or the like.

The subsystem 350 can further include a transmitter(s) 570, 588 and receiver(s) 572, 592 which can transmit and receive signals, respectively, to and from other devices, subsystems and/or other destinations using the one or more antennas 504 and/or links/busses. Included in the subsystem 350 circuitry is the medium access control or MAC Circuitry 522. MAC circuitry 522 provides for controlling access to the wireless medium. In an exemplary embodiment, the MAC circuitry 522 may be arranged to contend for the wireless medium and configure frames or packets for communicating over the wired/wireless medium.

The subsystem 350 can also optionally contain a security module (not shown). This security module can contain information regarding but not limited to, security parameters required to connect the device to one or more other devices or other available network(s), and can include WEP or WPA/WPA-2 (optionally+AES and/or TKIP) security access keys, network keys, etc. The WEP security access key is a security password used by $W_1$-Fi networks. Knowledge of this code can enable a wireless device to exchange information with an access point and/or another device. The information exchange can occur through encoded messages with the WEP access code often being chosen by the network administrator. WPA is an added security standard that is also used in conjunction with network connectivity with stronger encryption than WEP.

In some embodiments, the communications subsystem 350 also includes a GPU 540, an accelerator 544, a $W_1$-Fi/BT/BLE (Bluetooth® Low-Energy) PHY module 580 and a $W_1$-Fi/BT/BLE MAC module 584 and optional wireless transmitter 588 and optional wireless receiver 592. In some embodiments, the GPU 540 may be a graphics processing unit, or visual processing unit, comprising at least one circuit and/or chip that manipulates and changes memory to accelerate the creation of images in a frame buffer for output to at least one display device. The GPU 540 may include one or more of a display device connection port, printed circuit board (PCB), a GPU chip, a metal-oxide-semiconductor field-effect transistor (MOSFET), memory (e.g., single data rate random-access memory (SDRAM), double data rate random-access memory (DDR) RAM, etc., and/or combinations thereof), a secondary processing chip (e.g., handling video out capabilities, processing, and/or other functions in addition to the GPU chip, etc.), a capacitor, heatsink, temperature control or cooling fan, motherboard connection, shielding, and the like.

The various connectivity managers 534, 558, 562, 566 manage and/or coordinate communications between the subsystem 350 and one or more of the systems disclosed herein and one or more other devices/systems. The connectivity managers 534, 558, 562, 566 include a charging connectivity manager 534, a vehicle database connectivity manager 558, a remote operating system connectivity manager 562, and a sensor connectivity manager 566.

The charging connectivity manager 534 can coordinate not only the physical connectivity between the vehicle 100 and a charging device/vehicle, but can also communicate with one or more of a power management controller, one or more third parties and optionally a billing system(s). As an example, the vehicle 100 can establish communications with the charging device/vehicle to one or more of coordinate interconnectivity between the two (e.g., by spatially aligning the charging receptacle on the vehicle with the charger on the charging vehicle) and optionally share navigation information. Once charging is complete, the amount of charge provided can be tracked and optionally forwarded to, for example, a third party for billing. In addition to being able to manage connectivity for the exchange of power, the charging connectivity manager 534 can also communicate information, such as billing information to the charging vehicle and/or a third party. This billing information could be, for example, the owner of the vehicle, the driver/occupant(s) of the vehicle, company information, or in general any information usable to charge the appropriate entity for the power received.

The vehicle database connectivity manager 558 allows the subsystem to receive and/or share information stored in the vehicle database. This information can be shared with other vehicle components/subsystems and/or other entities, such as third parties and/or charging systems. The information can also be shared with one or more vehicle occupant devices, such as an app (application) on a mobile device the driver uses to track information about the vehicle 100 and/or a dealer or service/maintenance provider. In general, any information stored in the vehicle database can optionally be shared with any one or more other devices optionally subject to any privacy or confidentially restrictions.

The remote operating system connectivity manager 562 facilitates communications between the vehicle 100 and any one or more autonomous vehicle systems. These communications can include one or more of navigation information, vehicle information, other vehicle information, weather information, occupant information, or in general any information related to the remote operation of the vehicle 100.

The sensor connectivity manager 566 facilitates communications between any one or more of the vehicle sensors (e.g., the driving vehicle sensors and systems 304, etc.) and any one or more of the other vehicle systems. The sensor connectivity manager 566 can also facilitate communications between any one or more of the sensors and/or vehicle systems and any other destination, such as a service company, app, or in general to any destination where sensor data is needed.

In accordance with one exemplary embodiment, any of the communications discussed herein can be communicated via the conductor(s) used for charging. One exemplary protocol usable for these communications is Power-line communication (PLC). PLC is a communication protocol that uses electrical wiring to simultaneously carry both data, and Alternating Current (AC) electric power transmission or electric power distribution. It is also known as power-line carrier, power-line digital subscriber line (PDSL), mains communication, power-line telecommunications, or power-line networking (PLN). For DC environments in vehicles PLC can be used in conjunction with CAN-bus, LIN-bus over power line (DC-LIN) and DC-BUS.

The communications subsystem can also optionally manage one or more identifiers, such as an IP (Internet Protocol) address(es), associated with the vehicle and one or other system or subsystems or components and/or devices therein. These identifiers can be used in conjunction with any one or more of the connectivity managers as discussed herein.

Figure 6:
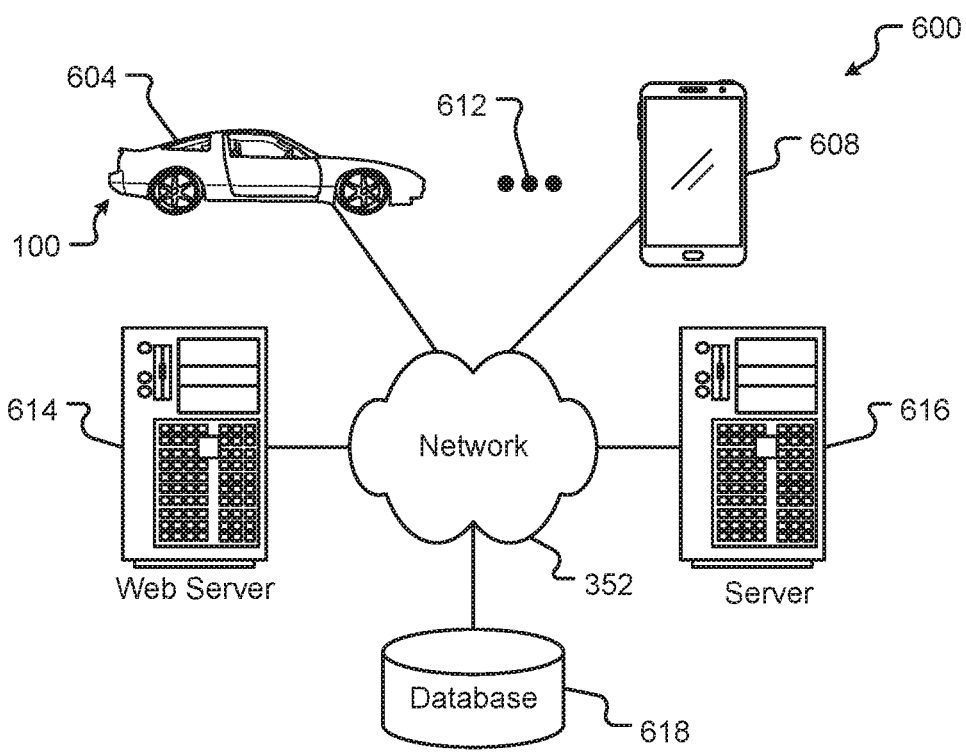
FIG. 6 is a block diagram of a computing environment associated with the embodiments presented herein.

FIG. 6 illustrates a block diagram of a computing environment 600 that may function as the servers, user computers, or other systems provided and described herein. The computing environment 600 includes one or more user computers, or computing devices, such as a vehicle computing device 604, a communication device 608, and/or more 612. The computing devices 604, 608, 612 may include general purpose personal computers (including, merely by way of example, personal computers, and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computing devices 604, 608, 612 may also have any of a variety of applications, including for example, database client and/or server applications, and web browser applications. Alternatively, the computing devices 604, 608, 612 may be any other electronic device, such as a thin-client computer, Internet-enabled mobile telephone, and/or personal digital assistant, capable of communicating via a network 352 and/or displaying and navigating web pages or other types of electronic documents or information. Although the exemplary computing environment 600 is shown with two computing devices, any number of user computers or computing devices may be supported.

The computing environment 600 may also include one or more servers 614, 616. In this example, server 614 is shown as a web server and server 616 is shown as an application server. The web server 614, which may be used to process requests for web pages or other electronic documents from computing devices 604, 608, 612. The web server 614 can be running an operating system including any of those discussed above, as well as any commercially-available server operating systems. The web server 614 can also run a variety of server applications, including SIP (Session Initiation Protocol) servers, HTTP(s) servers, FTP servers, CGI servers, database servers, Java® servers, and the like. In some instances, the web server 614 may publish operations available operations as one or more web services.

The computing environment 600 may also include one or more file and or/application servers 616, which can, in addition to an operating system, include one or more applications accessible by a client running on one or more of the computing devices 604, 608, 612. The server(s) 616 and/or 614 may be one or more general purpose computers capable of executing programs or scripts in response to the computing devices 604, 608, 612. As one example, the server 616, 614 may execute one or more web applications. The web application may be implemented as one or more scripts or programs written in any programming language, such as Java®, C, C #®, or C++, and/or any scripting language, such as Perl, Python, or TCL, as well as combinations of any programming/scripting languages. The application server(s) 616 may also include database servers, including without limitation those commercially available from Oracle®, Microsoft®, Sybase®, IBM® and the like, which can process requests from database clients running on a computing device 604, 608, 612.

The web pages created by the server 614 and/or 616 may be forwarded to a computing device 604, 608, 612 via a web (file) server 614, 616. Similarly, the web server 614 may be able to receive web page requests, web services invocations, and/or input data from a computing device 604, 608, 612 (e.g., a user computer, etc.) and can forward the web page requests and/or input data to the web (application) server 616. In further embodiments, the server 616 may function as a file server. Although for ease of description, FIG. 6 illustrates a separate web server 614 and file/application server 616, those skilled in the art will recognize that the functions described with respect to servers 614, 616 may be performed by a single server and/or a plurality of specialized servers, depending on implementation-specific needs and parameters. The computer systems 604, 608, 612, web (file) server 614 and/or web (application) server 616 may function as the system, devices, or components described in FIGS. 1-6.

The computing environment 600 may also include a database 618. The database 618 may reside in a variety of locations. By way of example, database 618 may reside on a storage medium local to (and/or resident in) one or more of the computers 604, 608, 612, 614, 616. Alternatively, it may be remote from any or all of the computers 604, 608, 612, 614, 616, and in communication (e.g., via the network 352) with one or more of these. The database 618 may reside in a storage-area network ("SAN") familiar to those skilled in the art. Similarly, any necessary files for performing the functions attributed to the computers 604, 608, 612, 614, 616 may be stored locally on the respective computer and/or remotely, as appropriate. The database 618 may be a relational database, such as Oracle 20i®, that is adapted to store, update, and retrieve data in response to SQL-formatted commands.

Figure 7:
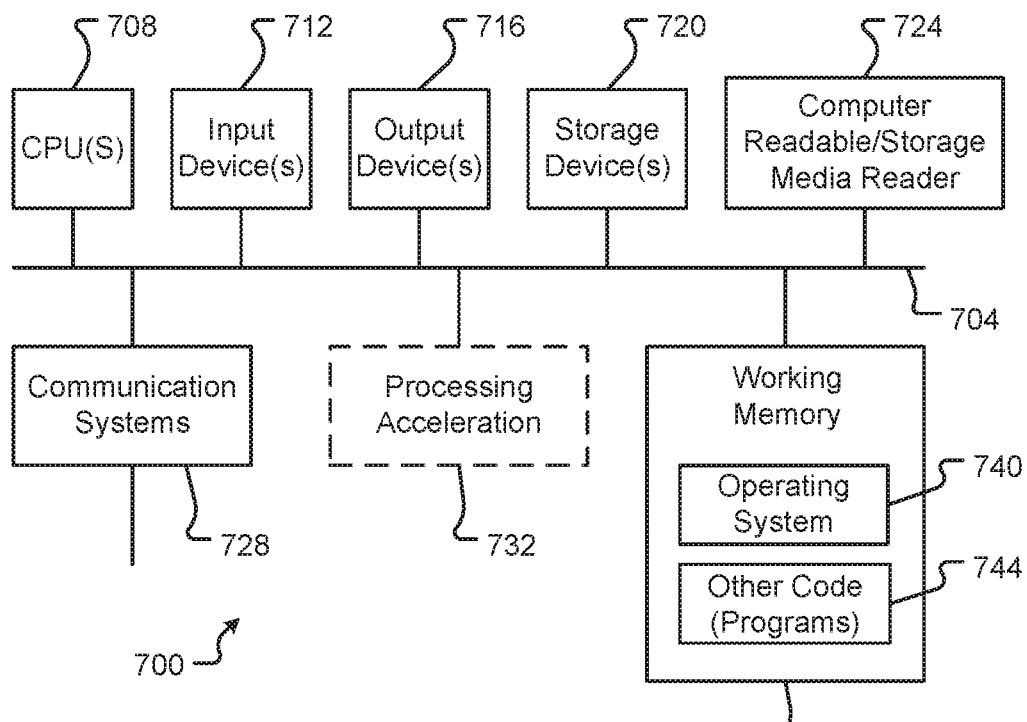
FIG. 7 is a block diagram of a computing device associated with one or more components described herein.

FIG. 7 illustrates one embodiment of a computer system 700 upon which the servers, user computers, computing devices, or other systems or components described above may be deployed or executed. The computer system 700 is shown comprising hardware elements that may be electrically coupled via a bus 704. The hardware elements may include one or more central processing units (CPUs) 708; one or more input devices 712 (e.g., a mouse, a keyboard, etc.); and one or more output devices 716 (e.g., a display device, a printer, etc.). The computer system 700 may also include one or more storage devices 720. By way of example, storage device(s) 720 may be disk drives, optical storage devices, solid-state storage devices such as a random access memory ("RAM") and/or a read-only memory ("ROM"), which can be programmable, flash-updateable and/or the like.

The computer system 700 may additionally include a computer-readable storage media reader 724; a communications system 728 (e.g., a modem, a network card (wireless or wired), an infra-red communication device, etc.); and working memory 736, which may include RAM and ROM devices as described above. The computer system 700 may also include a processing acceleration unit 732, which can include a DSP, a special-purpose processor, and/or the like.

The computer-readable storage media reader 724 can further be connected to a computer-readable storage medium, together (and, optionally, in combination with storage device(s) 720) comprehensively representing remote, local, fixed, and/or removable storage devices plus storage media for temporarily and/or more permanently containing computer-readable information. The communications system 728 may permit data to be exchanged with a network and/or any other computer described above with respect to the computer environments described herein. Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information.

The computer system 700 may also comprise software elements, shown as being currently located within a working memory 736, including an operating system 740 and/or other code 744. It should be appreciated that alternate embodiments of a computer system 700 may have numerous variations from that described above. For example, customized hardware might also be used and/or particular elements might be implemented in hardware, software (including portable software, such as applets), or both. Further, connection to other computing devices such as network input/output devices may be employed.

Examples of the processors 340, 708 as described herein may include, but are not limited to, at least one of Qualcomm® Snapdragon® 800 and 801, Qualcomm® Snapdragon® 620 and 615 with 4G LTE Integration and 64-bit computing, Apple® A7 processor with 64-bit architecture, Apple® M7 motion coprocessors, Samsung® Exynos® series, the Intel® Core™ family of processors, the Intel® Xeon® family of processors, the Intel® Atom™ family of processors, the Intel Itanium® family of processors, Intel® Core® i5-4670K and i7-4770K 22 nm Haswell, Intel® Core® i5-3570K 22 nm Ivy Bridge, the AMD® FX™ family of processors, AMD® FX-4300, FX-6300, and FX-8350 32 nm Vishera, AMD® Kaveri processors, Texas Instruments® Jacinto C6000™ automotive infotainment processors, Texas Instruments® OMAP™ automotive-grade mobile processors, ARM® Cortex™-M processors, ARM® Cortex-A and ARIV1926EJ-S™ processors, other industry-equivalent processors, and may perform computational functions using any known or future-developed standard, instruction set, libraries, and/or architecture.

It should be appreciated that embodiments provided herein are not directed to vehicle path route planning. Instead, the embodiments herein are generally directed to monitoring the path planner of a vehicle. The path planner is tasked to safely operate the vehicle in a dynamic, real-world environment. However, the path planner may receive erroneous data, such as from a failed or failing component and/or conflicting instructions provided by a plurality of processes. Regardless of the underlying reason, ensuring a vehicle does not operate outside of dynamically defined safety envelope will help ensure the safety and wellbeing of the vehicle, the vehicle's occupants, and persons and property that may encounter the vehicle.

An autonomous vehicle (AV), such as vehicle 100 either being autonomous or operating in an autonomous mode, requires many systems and data sources working together to provide safe locomotion of the AV and ensure the safety of passengers and properties and those who may encounter the AV. Sensor fusion is the aggregation of data from many systems, each utilizing unique data, shared data utilized in unique ways, and/or shared data and processing to provide redundancy, monitoring, or safety checks. However, when systems disagree or, even if in agreement, would place the AV in a unsafe state, the systems may be arbitrated by a supervisor processor or system. As systems get more complex, especially when operating in the unpredictable, or at best only partially predictable, real-world environment, a supervisor process or system to provide an overriding safety control helps ensure that, should the AV approach or exceed the boundary of a dynamically defined safety envelope, the systems responsible are notified. Once notified the systems can respond proportionately to mitigate and reverse the deviation and return the AV to safe operation or, if necessary, perform an appropriate emergency operation.

In one embodiment, and as a general introduction to the embodiments herein, a path boundary is determined from sensor and/or stored data. The path boundary indicating where vehicle 100 is expected to be within a particular timeframe. Additionally, a safe zone boundary is provided, such as defining an envelope—outside of which—vehicle 100 should never go. Both the path boundary and the safe zone boundary are dynamic envelopes determined from sensor and/or stored data for vehicle 100 at a given time and operational attribute (e.g., speed, visibility, road surface condition, predictability of other relevant vehicles, pedestrians, animals, etc.).

With the path boundary defined, should vehicle 100 venture outside the path boundary, one of two scenarios are likely: if the actuator feedback is deviating from the motion control commands, a warning signal may be sent to the actuator control system, or otherwise, the warning is sent to the motion control system. A warning to the actuator control system may then be processed to indicate that a command to perform an action was not executed as expected. Otherwise, if the actuator feedback is in accordance with the motion control commands, then the motion control system is provided with a warning signal, such as to indicate vehicle 100 is responding to controls appropriately, but yet a deviation from the path envelope is likely or has occurred, absent corrective action.

Should vehicle 100 be further determined to be approaching the safe zone boundary, without any deviation between the actuator feedback and the motion control commands, the motion control system, and/or other systems, are notified of failure with the motion control. However, if there is a deviation with the actuator feedback and the motion control commands, a failure signal is provided to the actuator controls.

The initial safe zone boundary may be defined from verified perception results and incorporate analyzed objects and/or conditions to a predefined safe zone boundary and dynamically refined as needed. An enhanced safe zone boundary may then be used to monitor the vehicle's path planner to ensure that the vehicle's path is within defined safe zone boundary.

In one embodiment, a safe zone boundary is defined for monitoring vehicle's path planner by using the verified object list with the coordinates of a vehicle's domain, data from vehicle state sensors, and/or a pre-defined fault tolerance safety margin to define safe zone boundary around vehicle.

In another embodiment, a method for analyzing impact of safety-critical objects is provided to enhance safe zone boundary, which may comprise, the performance of Safety Of The Intended Functionality (ISO 26262) ("SOTIF") and/or Hazard Analysis and Risk Assessment (ISO 26262) ("HARA") to generate critical safety object library, search for critical safety objects from the verified object list (e.g., traffic light, stop sign, etc.), and/or analyze the necessity of refining initial safe zone boundary. SOTIF and HARA are incorporated herein by reference.

In another embodiment, various inputs are received from vehicle 100's planned motion path, vehicle safe zone boundary, vehicle state data, motion control commands, actuator control feedbacks, etc. A determination is made as to vehicle 100's current location relative to the vehicle's planned path envelope and/or safe zone boundary. By comparing relative location, as well as motion control commands vs actuator control feedbacks, a determination may be made to accordingly, including:

Vehicle is within planned path envelop—Continue vehicle operations normally, no corrective action is needed.

Vehicle is outside of planned path envelop, but within safe zone boundary:

A) If the actuator feedback deviates from the motion control commands, motion control monitor issues a warning to actuator control.

B) If the actuator control feedbacks follow motion control commands, motion control monitor issues a warning to motion control.

Vehicle is approaching safe zone boundary:

A) If the actuator feedback deviates from motion control command, motion control monitor requests actuator control to transition to fail operation state.

B) If the actuator control feedbacks follow motion control commands, motion control monitor requests motion control to transition to fail operation state.

In another embodiment, motion control monitoring is performed which may utilize a predefined safe zone boundary, together with vehicle state sensor data, vehicle path envelope, motion control commands, and/or actuator control feedbacks.

In another embodiment, an improved diagnostic is provided with external independent motion control monitors, which may lead to early detection of system failure and avoid potential vehicle hazards by assisting fail operational transitions and their responses.

Figure 8:
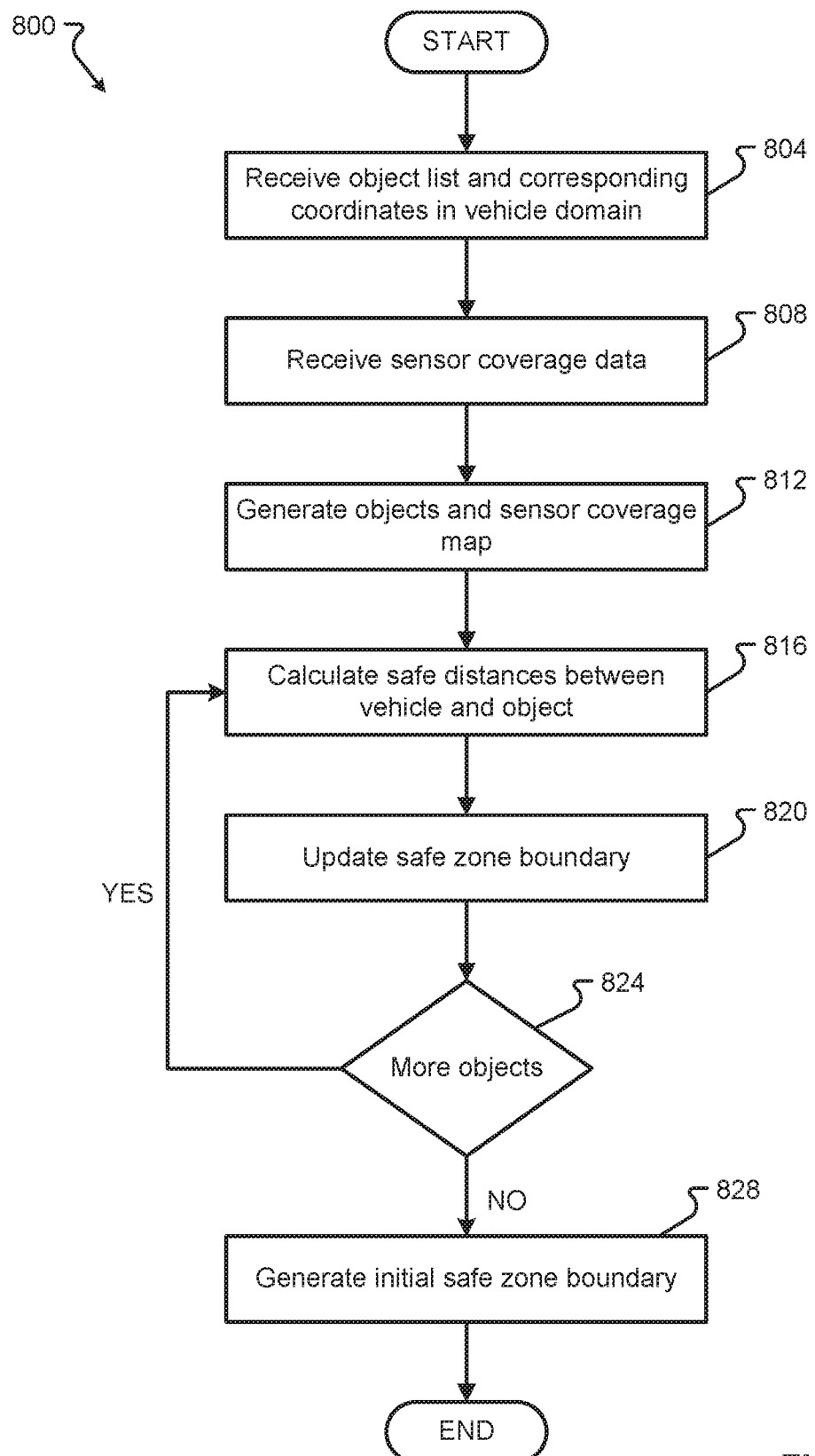
FIG. 8 shows a process for generating an initial safe zone boundary in accordance with embodiments of the present disclosure.

FIG. 8 shows process 800 for generating an initial safe zone boundary in accordance with embodiments of the present disclosure. In one embodiment, at least a portion of process 800 is executed by a processor within a vehicle, such as CPU(s) 708 of the vehicle control subsystem 348 of the vehicle 100 with results stored in working memory 736, storage device(s) 720, and/or output to an external storage, such as database 618. In another embodiment, at least a portion of process 800 is executed by a processor located outside of vehicle 100, such as server 616 and/or web server 614. The results from the external processors being utilized for additional processing/or loaded to vehicle 100 via network 652.

In another embodiment, an object list is received with a corresponding coordinates of the vehicle's domain, in step 804. The object list may be verified, such as by agreement with two or more data sources, a previously determined trustworthy data source, and/or a probability of the presence and/or type or identity of the object above a previously determined threshold. For example, an object that is highly portable (e.g., debris, parked car, construction signage, etc.) may have a lower threshold versus a fix or constructed object (e.g., stop sign, light pole, tree, building) which may have a higher threshold.

Next, in step 808 sensor connectivity manager 566 receives sensor data, such as from one or more input devices 712, when embodied as an environmental sensor (e.g., radar, Lidar, optical camera, sonar, etc.). The sensor data may additionally be verified, such as when there is agreement between two or more sensors and/or a confidence above a previously determined threshold. Additionally or alternatively, agreement between a sensor and an object list entry may serve as a validation for the object. For example, if the object list, verified or not verified, indicates an object at a certain location, an object being determined to be present by sensor data at the same location, may be a verification. In another embodiment, if sensor coverage is mapped and optionally verified, such that a coverage is determined. For example, forward sensors cover one hundred meters forward, twenty meters to the side, and five meters behind. The sensors may be a single type (e.g., all Lidar) or a mixture of types.

In step 812, an object and sensor map is generated by the vehicle control subsystem 348, whereby known (or known within the previously determined threshold) objects are identified as well as the area covered by sensor data. Then, in step 816, safe distances may be determined by the vehicle control subsystem 348 between objects and the vehicle. For example, an object, that was identified on the received object list, may be a light pole and have a safe distance of one meter. Whereas a cyclist, pedestrian, or an unknown object may require a greater margin of safety due to either or both of the unpredictable nature of humans and the seriousness of the consequence resulting from physical contact. With the safe distances determined, step 816 updates a safe zone boundary. In step 824 the vehicle control subsystem 348 determines if there are more objects to map and, if yes, process 800 continues back at step 816 and, if not, process 800 continues to step 828 and the generation of an initial safe zone boundary.

The safe distance may also depend on the position of the object relative to the direction of travel and speed of vehicle 100. For example, the vehicle control subsystem 348 may determine a safe distance for a cyclist may be one meter from vehicle 100 when the cyclist is not within the path of travel of vehicle 100 (e.g., vehicle 100 is passing the cyclist). However, a safe distance for a cyclist within the direction of travel, when the speed of vehicle 100 is, for example fifty miles-per-hour, will be much bigger. Again, the speed may determine, in whole or in part, the safe distance. Being within one meter of a cyclist, such as when the speed is negligible (e.g., nearly stopped at a traffic signal, stop-and-go traffic, etc.), may be a safe distance.

Figure 9:
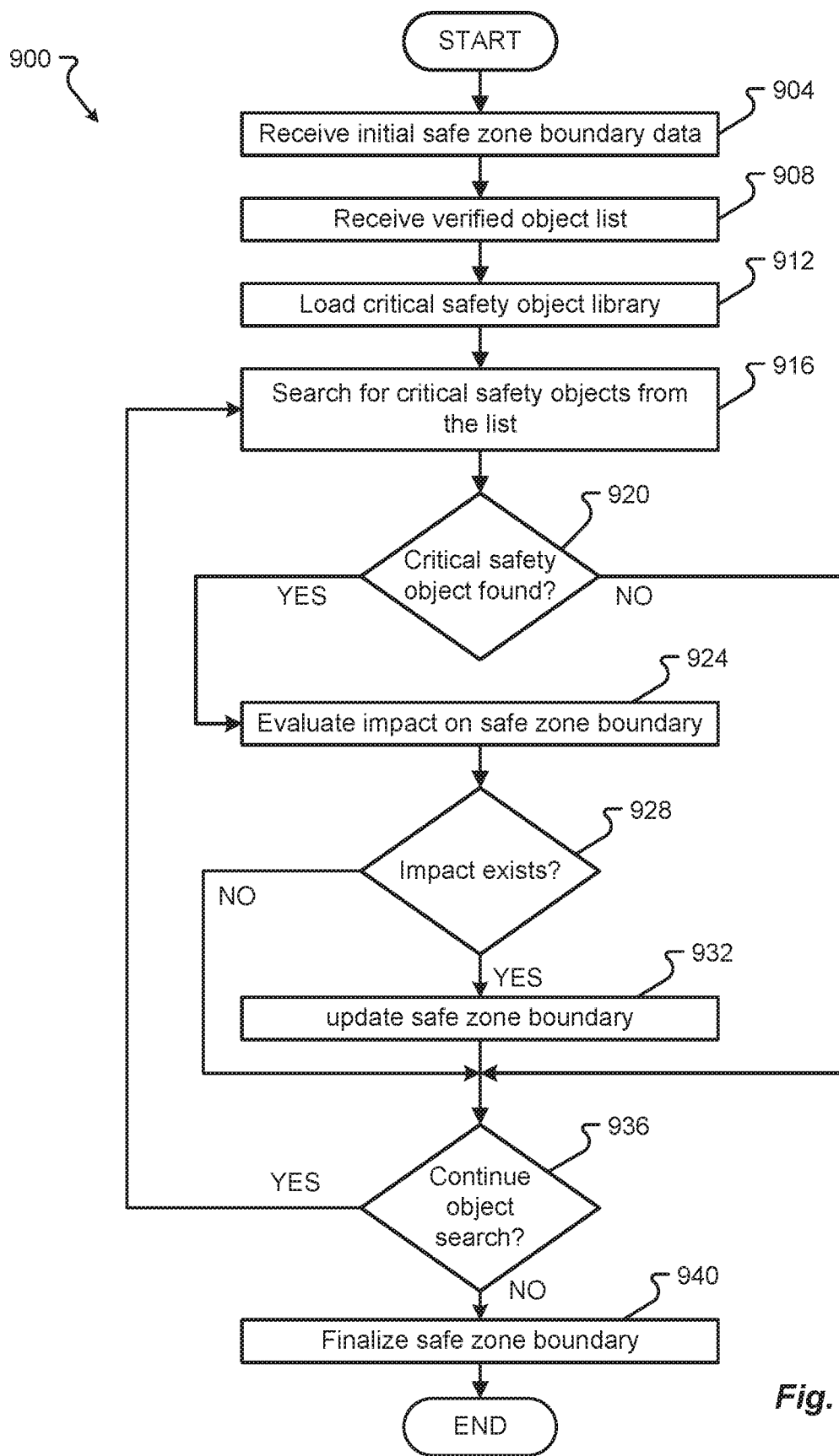
FIG. 9 shows a process for generating a final safe zone boundary in accordance with embodiments of the present disclosure.

FIG. 9 shows process 900 for generating a final safe zone boundary in accordance with embodiments of the present disclosure. The execution of process 900 is preferably performed by a processor within a vehicle, such as CPU(s) 708 of the vehicle control subsystem 348 of the vehicle 100 with results stored in working memory 736, storage device(s) 720, and/or output to an external storage, such as database 618. However, executing at least a portion of process 900 a processor located outside of vehicle 100, such as server 616 and/or web server 1014, is also contemplated and, the results therefrom, being communicated to vehicle 100 via network 352.

Process 900 may be performed upon startup of vehicle 100 and/or intermittently during operation of vehicle 100. In another embodiment, at process 900 or at least a portion of process 900 (e.g., steps 916 through 936 and, optionally, step 940) are performed continuously during the operation of vehicle 100.

In another embodiment, step 904 receives the initial safe zone boundary, such as an output from step 828 (see, FIG. 8). Next, step 908 verifies each object in the list received in step 904. Verification may be accomplished by one or more of: confirmation between two or more sources, confirmation by at least one trusted source, live (e.g., sensor) data, manual conformation, and/or other verification process. Next, a library of stored critical safety objects is loaded at step 912 and at step 916 critical safety objects are searched in the object list received in step 908.

Step 920 determines if the critical safety object was found in the object list. If step 920 is determined in the affirmative, processing continues to step 924. If step 920 is determined in the negative processing continues at step 936. In step 924, an evaluation is made on the safe zone boundary. For example, whether or not the initial, or a subsequently refined, safe zone boundary encompasses the object. If, as determined at step 928, an impact on the safe zone boundary exists, processing continues at step 932 wherein the safe zone boundary is updated, such as to revise the safe zone to exclude the object. Following step 932, or upon step 928 being determined in the negative, processing continues at step 936 whereby a determination is made as to whether more object searching should be performed. If step 936 is determined in the affirmative, processing continues at step 916 otherwise, processing continues at step 940 whereby a finalized safe zone boundary is produced.

Figure 10:
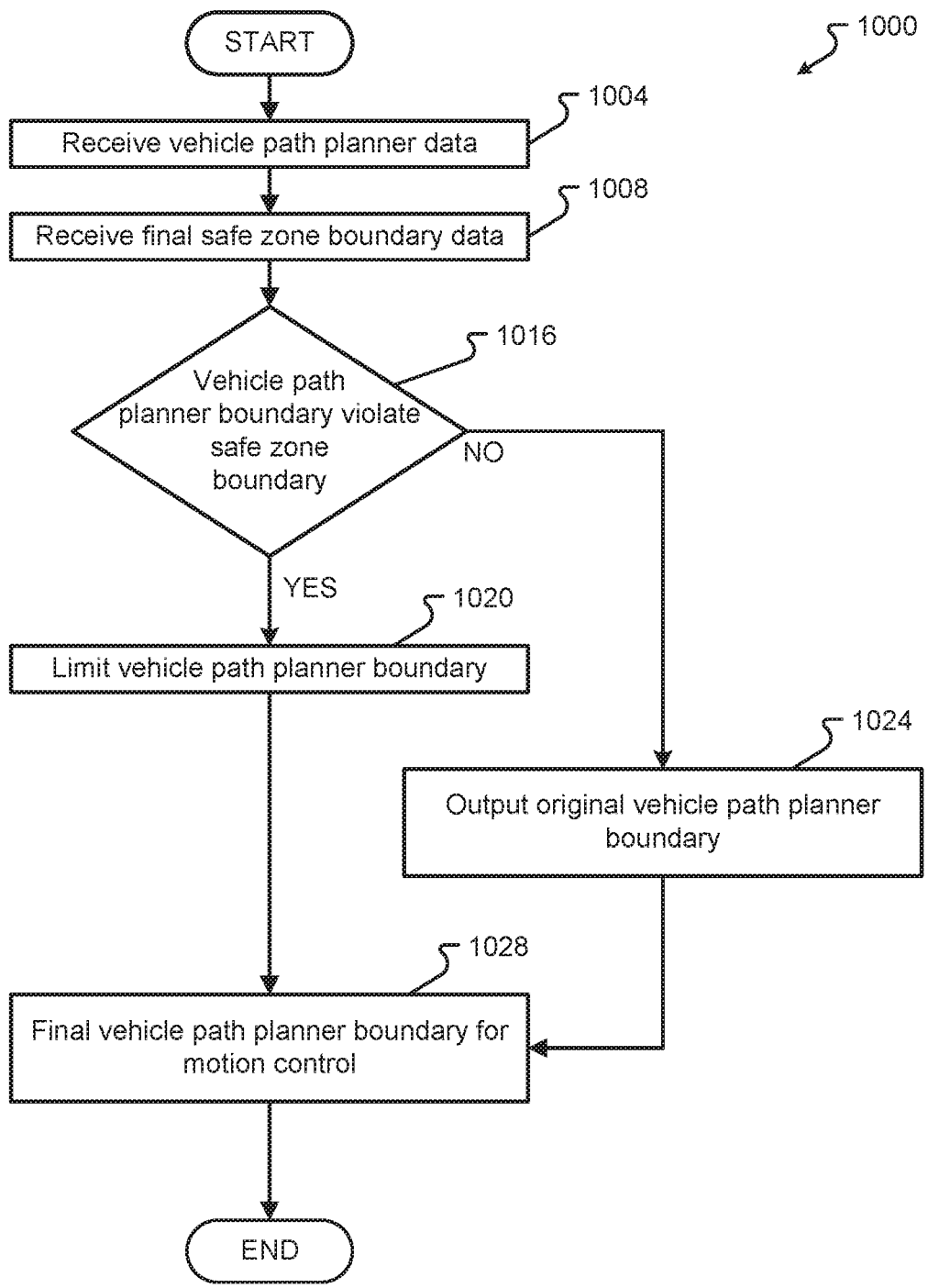
FIG. 10 shows a process for finalizing a vehicle path planner boundary in accordance with embodiments of the present disclosure.

FIG. 10 shows process 1000 for finalizing a vehicle path planner boundary in accordance with embodiments of the present disclosure. The execution of process 1000 is preferably performed by a processor within a vehicle, such as CPU(s) 708 of vehicle 100 with results stored in working memory 736, storage device(s) 720, and/or output to an external storage, such as database 618. However, executing at least a portion of process 1000 a processor located outside of vehicle 100, such as server 616 and/or web server 614, is also contemplated and, the results therefrom, being communicated to vehicle 100 via network 352.

In one embodiment, step 1004 receives vehicle path planner data. For example, routes, alternative routes, position within the roadway, speed, etc. Step 1008 receives the final safe zone boundary, such as the output of step 940 (see, FIG. 9). Next, step 1016 determines if the vehicle path planner boundary violates the safe zone boundary and, if determined in the affirmative, process 1000 continues with step 1020 and, if determined in the negative, process 1000 continues with step 1024. For example, if the path of vehicle 100 requires the safe zone boundary to be broken by an object, step 1016 would be determined in the affirmative. Accordingly, at step 1020, the path planner boundary is limited such that the safe zone boundary is not violated by an object. If step 1024 is determined in the negative, step 1024 maintains the original vehicle path planner boundary as the final vehicle path planner boundary to be provided to a motion control system, by step 1028. Similarly, step 1028 when preceded by step 1020, modifies the final vehicle path planner boundary for motion control as limited by step 1020.

In one embodiment, motion control comprises one or more locomotion and/or directional decision and control systems of vehicle 100. For example, vehicle 100 when autonomous or operating in fully or partially autonomous mode utilizes electric motor 804, steering 410, braking, and/or other components to operate vehicle 100. The motion control systems having a computational element, determining a particular vector or vector change (e.g., maintain thirty miles-per-hour, turn left at the next intersection, brake to a complete stop at the stop sign, steer three degrees to the left to maintain position within the lane, etc.). The outputs of the motion control system being implemented by the actuator control system to provide physical forces to the control components of vehicle 100 (e.g., steering linkage, braking, throttle position—either electrical, such as a rheostat, or mechanical for a carburetor or fuel injection system, etc.) and may also be embodied, in whole or in part, by vehicle control subsystem 348.

Figure 11:
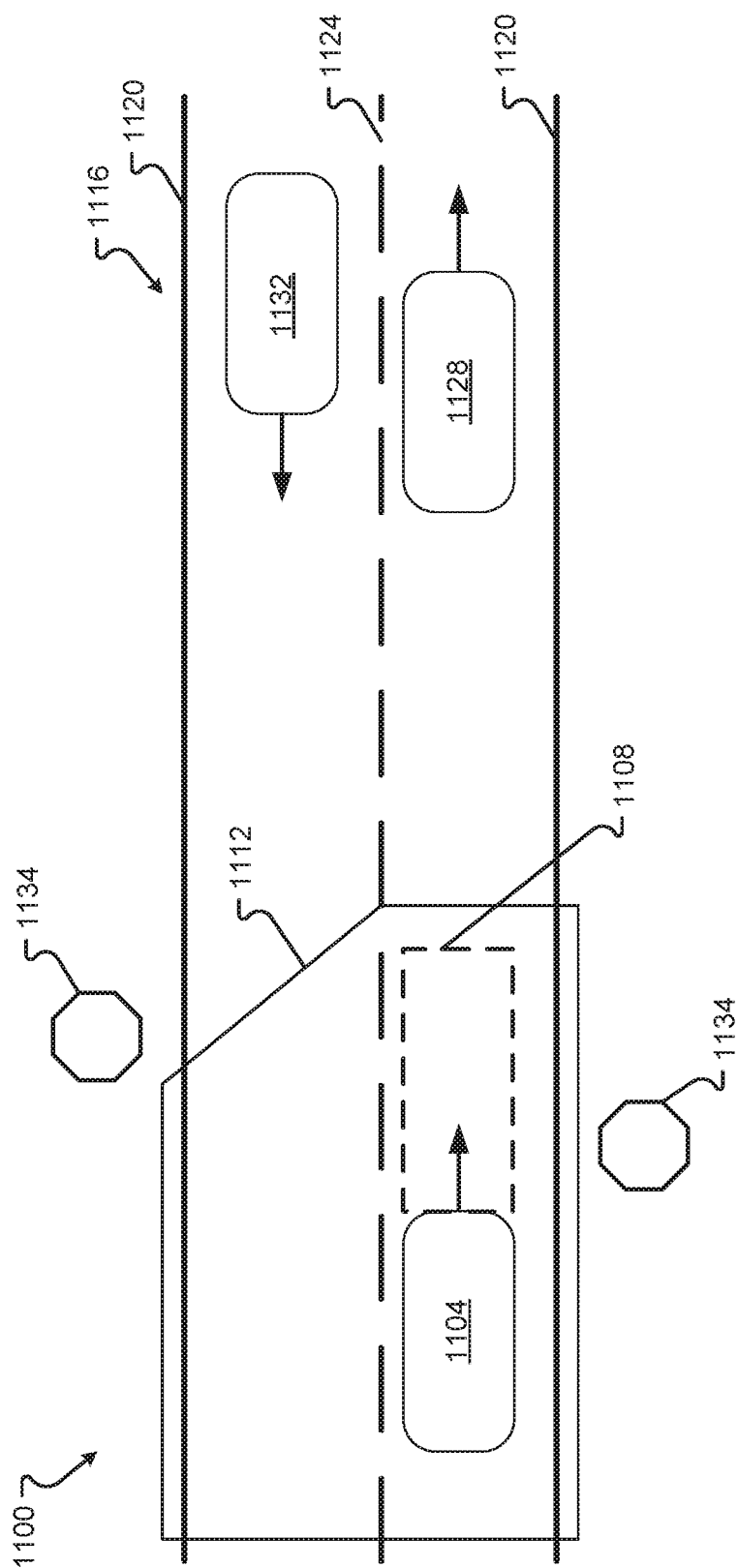
FIG. 11 shows a first plan view of vehicle operation in accordance with embodiments of the present disclosure.

FIG. 11 shows plan view 1100 of vehicle 1104 operation in accordance with embodiments of the present disclosure. In one embodiment, vehicle 1104 may be vehicle 100 when autonomous or operated in autonomous mode. Vehicle 1104 traverses roadway 1116 delineated by edges 1120 and centerline 1124, when embodied as a two-lane, two-way road. As can be appreciated by those of ordinary skill, one-way, multiple lane, single lane, intersections, merges, curves, and/or other configurations of roadway 1120 are contemplated by the embodiments herein. Additionally, while roadway may be explicitly delineated, such as by painted center line 1124 and/or painted edges 1120, other delineations may be used (e.g., boundary between asphalt or concrete to a non-roadway surface (e.g., dirt, grass, gravel, etc.) a determined distance from a delineating object (e.g., guardrail, sidewalk, parked cars, etc.). The delineating objects may be "objects" as utilized herein.

In one embodiment, vehicle 1104 traverses roadway 1120 with other vehicles, such as leading vehicle 1128 and oncoming vehicle 1132. Obstacles 1134 are, with respect to view 1100, outside of roadway 1120. However, other obstacles may be within roadway 1120, as will be discussed in more detail with respect to FIG. 12. The position of objects 1134 may be known from a stored location, such as working memory 736, storage devices 720, or other data repository which may have been populated during an initial and/or final safe zone determination (e.g., steps 804 and/or 908). As a result, safe zone 1112 is determined. Vehicle path 1108 illustrates the position of vehicle 100 at a relevant timeframe in the future. The position of vehicle path 1108 is in an intended direction of travel of vehicle 100. Vehicle path 1108 may represent a desired location for vehicle 100 and/or a position that vehicle 100 is physically capable of entering, regardless of control inputs. For example, when traveling at highway speeds, the inertia of vehicle 1104, even with hard braking and/or turning, will cause vehicle 100 be at the location currently illustrated by vehicle path 1108.

In another embodiment, safe zone 1112 is irregularly shaped, such as to account for oncoming vehicle 1132 and/or obstacle 1134.

Vehicle path 1108 and/or safe zone 1112 may be redrawn (e.g., recalculated and stored in memory) based upon updated sensor data from sensors (e.g., one or more of sensors 116, 112).

Figure 12:
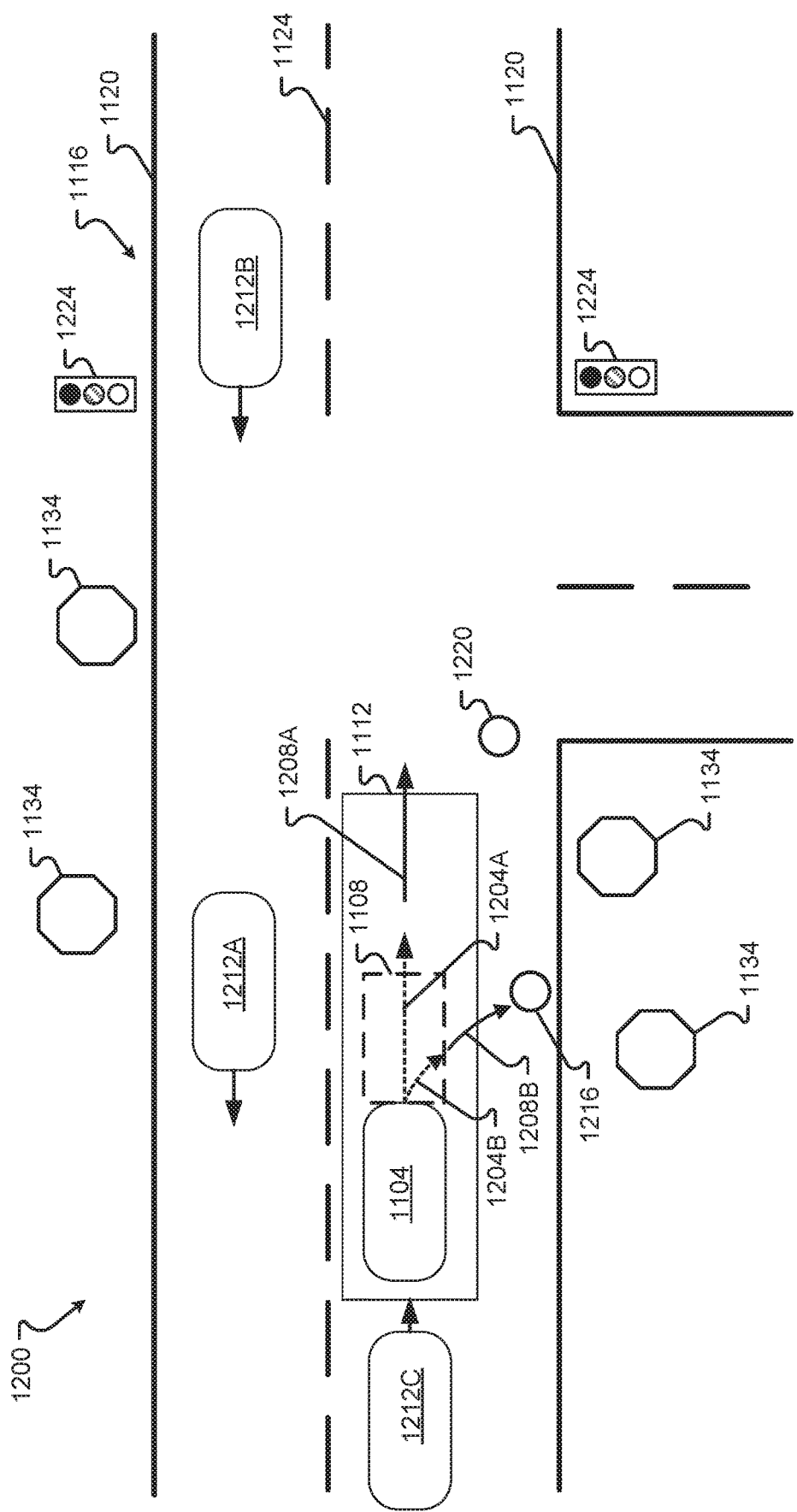
FIG. 12 shows a second plan view of vehicle operation in accordance with embodiments of the present disclosure.

FIG. 12 shows plan view 1200 of vehicle operation in accordance with embodiments of the present disclosure. In one embodiment, vehicle 1104 is traversing roadway 1116. Obstacles 1134 are identified and mapped (see, FIG. 11). Other vehicles 1212A-C, traffic signal 1224, cyclist 1216, and pedestrian 1220 are detected, such as via sensors (e.g., one or more of sensors 116, 112) and/or object list entries.

In another embodiment, safety warning trigger vectors 1204A-B are determined. While only two paths are illustrated, it should be appreciated that a path or zone may be determined for greater number of potential trajectories. Should vehicle 100 follow any of the trajectories illustrated by safety warning trigger vectors 1204A-B, a corrective action is taken (discussed in greater detail with respect to FIG. 13). Should vehicle 100 follow any of the trajectory illustrated by fail operation vectors 1208A-B, then a failure-action may be taken (also discussed in greater detail with respect to FIG. 13).

In a further embodiment, safety warning trigger vectors 1204A-B are any determined position outside of vehicle path 1108 but with safe zone boundary 1112. In another embodiment, fail operation vector 1208A-B is a vehicle path that would take vehicle 100 outside of safe zone boundary 1112.

As components of vehicle 100 determine paths of travel, and modify those paths, such as due to the position of cyclist 1216, pedestrian 1220, traffic light 1224, or other static or dynamic obstacle, such as obstacles 1134, faults may arise. The fault may be logical (e.g., a decision is made to allow vehicle 100 to approach pedestrian 1220 too closely) or mechanical/electro-mechanical (e.g., the steering was instructed to turn, but due to a breakage or ice on the roadway, the steering operation is not effective in turning vehicle 100). Such faults, while still indicating a defect, may be harmless in some circumstances (e.g., no obstacles 1134, cyclists 1216, vehicles 1212, etc. proximate to vehicle 100) or exceptionally hazardous in other circumstances. Should, for example, pedestrian 1220 dart out in front of vehicle 1104, safe zone boundary 1112 is recalculated and may cause portions of vehicle path 1108 to fall outside the safe zone boundary. Accordingly, an evasive measure may need to be taken. Turning to the right would cause vehicle 100 to exit safe zone boundary 1112, such as to traverse fail operation vector 1208B, and turning to the left would cause vehicle 100 to exit safe zone boundary 1112 indicating a hazard with vehicles 1212A and/or 1212B. Hard braking may initiate a collision from vehicle 1212C. While the specific action taken will vary based on the details of the specific details, in one embodiment, a plurality of vehicle paths 1108 are calculated and the one selected has the least transgression into safe zone boundary 1112, which may have been original (e.g., as finalized in step 940) or as recalculated, such as upon detecting the movement of pedestrian 1220.

Figure 13A:
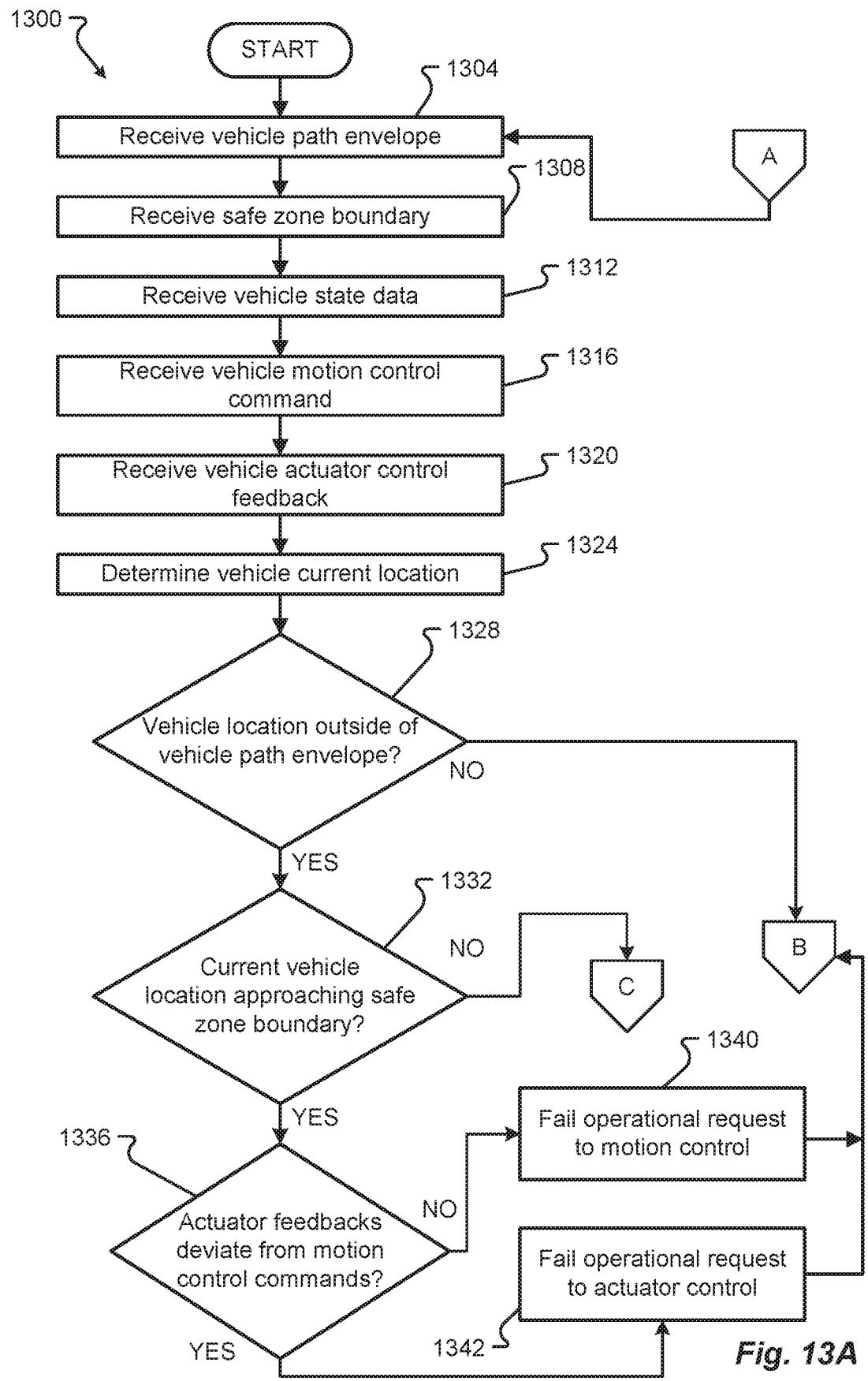
FIGS. 13A-C shows a process for operating a vehicle in accordance with embodiments of the present disclosure.
Figure 13B:
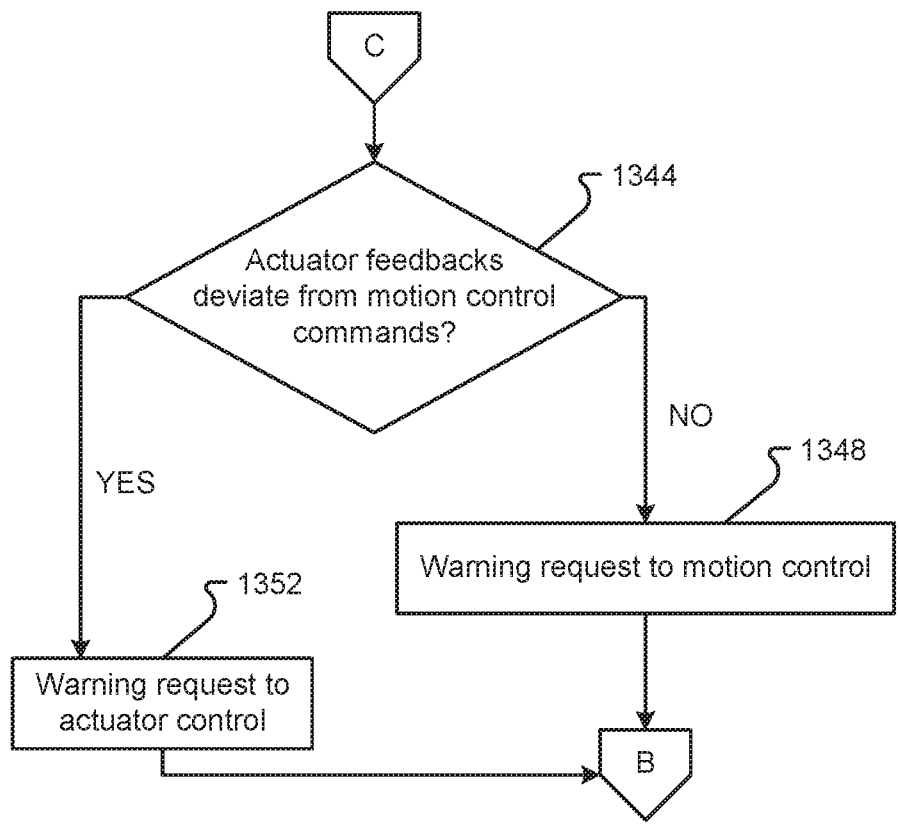
Figure 13C:
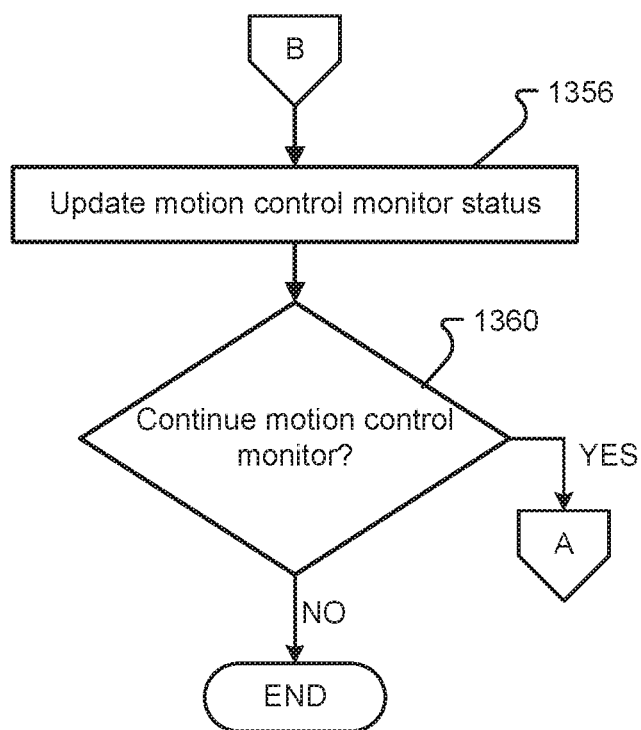

FIGS. 13A-C shows process 1300 for operating a vehicle in accordance with embodiments of the present disclosure. The execution of process 1300 is preferably performed by a processor within a vehicle, such as CPU(s) 708 of vehicle 100 with results stored in working memory 736, storage device(s) 720, and/or output to an external storage, such as database 618. However, executing at least a portion of process 1300 a processor located outside of vehicle 100, such as server 616 and/or web server 614, is also contemplated and, the results therefrom, being communicated to vehicle 100 via network 352.

In one embodiment, step 1304 receives vehicle path envelope (e.g., output from step 1028), such as by CPU(s) 708, as well as the safe zone boundary, at step 1308 (e.g., output from step 940), vehicle state data, at step 1312, vehicle motion control command, at step 1316, vehicle actuator control feedback, at step 1320, and determine a current location of vehicle 100, at step 1324. Vehicle state data may comprise one or more operational or situational states, such as from driving sensors 304, communications system 350, computing devices 368, sensor processor 340, and/or other component, subcomponent, communication interface, input device, or combination thereof. Step 1316 receives a motion control command, such as an output from vehicle control subsystem 348 causing vehicle 100 to perform a motion (e.g., change speed/direction, maintain speed/direction, change relative position on a roadway, etc.). Step 1320 receives actuator control feedback signals, such as from vehicle control system 348, when embodied to incorporate electrical, electromagnetic, pneumatic, hydraulic, and/or electro-mechanical actuators that, in turn, apply a force and/or cause a portion of vehicle 100 (e.g., tires) to apply a force to the roadway to maintain or alter a direction of travel and/or speed. Current location, determined at step 1324, may be provided via output from navigation system 302, navigation source 356A, location module 333, imaging system 112, one or more sensors 116, and/or other component or combination thereof.

Step 1328 determines whether the vehicle location is outside of the vehicle path envelope. If step 1328 is determined in the negative, processing continues to step 1356 (see, FIG. 13C). If step 1328 is determined in the affirmative, processing continues to step 1332. Step 1332 determines if the current vehicle location is approaching the safe zone boundary. If step 1332, is determined in the affirmative, processing continues to step 1336. If step 1332 is determined in the negative, processing continues to step 1334 (see, FIG. 13B). Step 1336 determines if the actuator feedback signals deviate from the motion control commands. If step 1336 is determined in the negative, processing continues to step 1340, which issues a fail operational request to the motion control and processing continues to step 1356. If step 1336 is determine in the affirmative, processing continues to step 1342 which sends the fail operational request to the actuator control and processing then continues to step 1356.

In step 1356, the motion control monitor status is updated and a determination is made as to whether the motion control monitoring should continue. If yes, processing continues back to step 1304, otherwise process 1300 may terminate.

In step 1344, a determination is made as to whether the actuator feedback(s) deviate from the motion control commands. If step 1344 is determined in the affirmative, step 1348 issues a warning to the motion control system in step 1348, if determined in the negative, a warning is issued to the actuator control in step 1352. Following either the step 1348 or 1352, processing continues to step 1356.

As introduced above, embodiments herein address and mitigate potential faults associated with vehicle 100 operating autonomously. Errors may be induced such as by a translation error, faulty sensor, or a near limitless number of other sources.

Step 1348 may issue a warning to the motion control system. Vehicle 100 may comprise a redundant and/or backup motion control system. In response to a warning, the motion control system may switch from an active motion control system to the backup. Additionally or alternatively, the motion control system may utilize alternative algorithms and/or include or exclude data (such as from one or more sensors 304) and recalculate vehicle path 1108 in such a manner to mitigate vehicle 100 approach the safe zone boundary and, thereby, allow step 1332 to be re-determined in the negative.

Step 1352 may issue a warning to the actuator control system. For example, a command to turn vehicle 100 ten degrees to the right, may result in a lack of compliance, such as due to a failed component or connection to the component. Accordingly, step 1344 is determined in the affirmative. In response to the warning, the translated action may be altered. For example, a linear motor may be attached to the steering linkage and receive an electrical signal, such as a particular encoding or voltage, that causes the linear motor to apply a particular force to the steering linkage and, if operating correctly, turn vehicle 100 by ten degrees. However, if the response was too much or too little, an alternative signal may be applied to the linear motor in accordance with an observed result, such as a 3 volt signal is intended to translate to a ten degree turn, but if the observed result is less, a 5 volt signal may be applied to the linear motor.

Step 1340 may issue a fail operation to the motion control system. In response, the motion control system may utilize a backup system. Additionally or alternatively, the motion control system may utilize alternative algorithms and/or include or exclude data (such as from one or more sensors 304) and recalculate vehicle path 1108 in such a manner to mitigate vehicle 100 approach the safe zone boundary and, thereby, allow step 1332 to be re-determined in the negative. Furthermore, failure to motion control may signal an occupant of vehicle 100 to resume control and disengage autonomous operation.

Step 1342 may issue a fail operation to the actuator control system. In response, the actuator control system may a backup connection, solenoid, or other secondary or backup component may be utilized in an attempt to execute the command.

Steps 1340, 1342, 1348, and 1352 provide messages such that the message receiving component (e.g., motion control, actuator control, etc.) may initiate a mitigating action. In additional embodiments, and in response to warnings and/or failures requests, an indicated on display 400 such as to allow an occupant of vehicle 100 to take control, message sent via communication subsystem 350, and/or alert others in the area, such as by flashing the lights, honking the horn, etc. or otherwise provide an indication that vehicle 100 may be in distress or suffering a loss of control and thereby allow other motors, autonomous vehicles, pedestrians, etc. to become aware of the state of vehicle 100.

Figure 14:
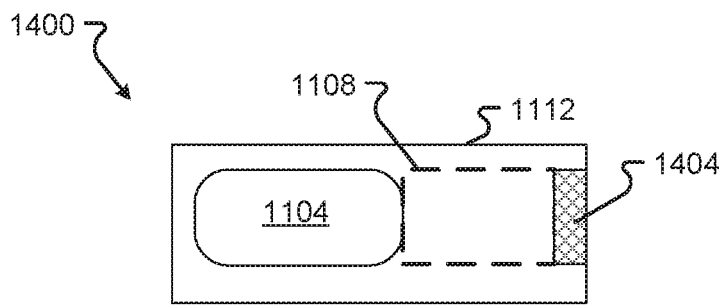
FIG. 14 shows a warning event in accordance with embodiments of the present disclosure.

FIG. 14 shows diagram 1400 illustrating a warning event in accordance with embodiments of the present disclosure. Diagram 1400 illustrates vehicle 1104, vehicle path 1108, and safe zone 1112. In one embodiment, safe zone 1112 that has been resized, such as due to a sensed obstacle 1134, pedestrian 1220, other vehicle 1212, cyclist 1216, etc. Vehicle path 1108 is within a distance defined by warning area 1404 of safe zone 1404. Warning area 1404 may be determined in accordance with the type of hazard, such as a box that has blown into traffic may allow a greater size of warning area 1404 as opposed to pedestrian 1220. Additionally, other hazards, such as a tailgating vehicle (e.g., 1212C) may cause warning area 1404 to be increased, such as when the hazard associated with hitting a box is less than that of being rear ended. The warning message may be send according to process 1300.

Figure 15:
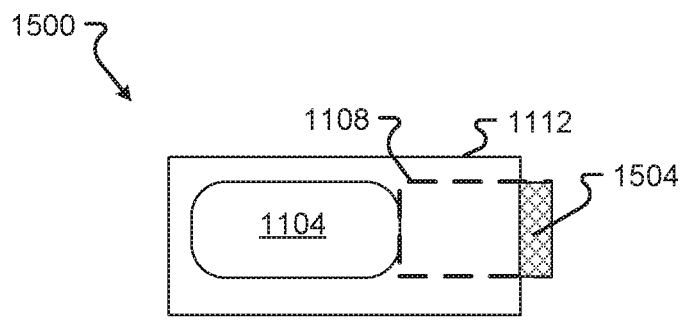
FIG. 15 shows a first failure event in accordance with embodiments of the present disclosure.
Figure 16:
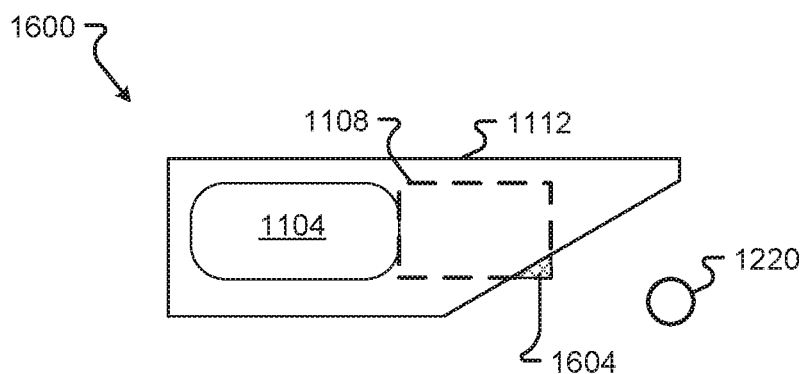
FIG. 16 shows a second failure event in accordance with embodiments of the present disclosure.

FIGS. 15-16 show diagrams 1500 and 1600, respectively, each illustrating vehicle 1104, vehicle path 1108, and safe zone 1112. Diagram 1500 illustrates safe zone 1112 that has been resized such that vehicle path 1108 is within failure area 1504. Diagram 1600 illustrates failure area 1604 caused by pedestrian 1220. Accordingly, as vehicle path 1108 overlaps with safe zone 1112, by failure area 1504 in diagram 1500 and by failure area 1604 in diagram 1600, a failure message may then be sent accordingly to process 1300.

Figure 17:
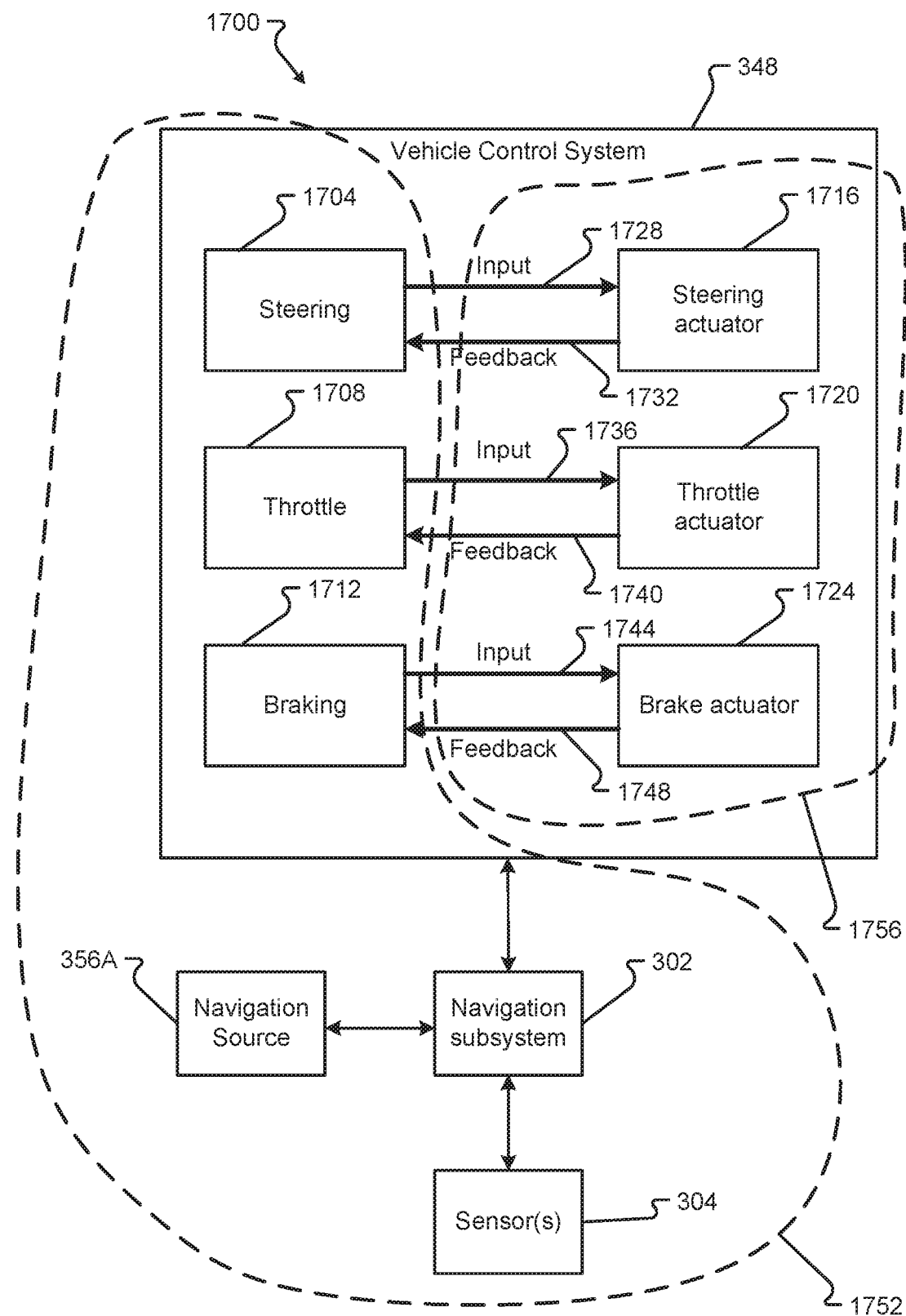
FIG. 17 shows a block diagram of a portion of a motion control system in accordance with embodiments of the present disclosure.

FIG. 17 shows block diagram 1700 illustrating motion control system 1752 and actuator control 1756 in accordance with embodiments of the present disclosure. In one embodiment, the motion control system 1752 comprises computing and physical components of vehicle 100 to navigate vehicle 100 on roadway 1120 or other surface in a manner that causes vehicle 100 to reach its destination, waypoint, or follow a path while avoiding obstacles 1134 and/or other hazards. In another embodiment, the motion control system comprises navigation subsystem 302, sensors 304, vehicle control subsystem 348 and navigation source 356A. Additionally or alternatively, motion control system may utilize few components or additional components, such as control source 356B, control data 364, communications subsystem 350, and/or other components.

In another embodiment, actuator control comprises components 1756 comprise components that may cause a change in the speed and/or direction of vehicle 100. In one embodiment, vehicle control system 348 comprises at least a portion of actuator control components 1756.

In one embodiment, the motion control system 1752 may comprise steering controller 1704, throttle controller 1708, and/or breaking controller 1712 are provided to translate speed and/or direction changes provided by an input, such as navigation subsystem 302, into command signals for steering actuator 1716, throttle actuator 1720, and/or brake actuator 1724, respectively. More specifically, steering controller provides input 1728 to steering actuator 1716 and receives feedback 1732, throttle actuator 1708 provides input 1736 to throttle actuator 1720 and receives feedback 1740, and brake controller 1712 provides input 1744 to brake actuator 1724 and receives feedback 1748. It should be appreciated that throttle controller 1708 and throttle actuator 1720 may manipulate a true throttle (e.g., carburetor butterfly valve) or other speed-regulating component (e.g., a rheostat or other electrical controller providing power to a motor of vehicle 100 utilized for locomotion) of vehicle 100. Regenerative braking may also be implemented in vehicle 100 and thereby combine throttle controller 1708 with brake controller 1712, which may further utilize throttle actuator 1720 and brake actuator 1724 individually or as a combination.

An actuator fault may occur when an intended response is not observed via a feedback. For example, steering controller 1704 may receive a navigation input from navigation subsystem 302 to turn vehicle 100 requiring a ten degree turn of the angle of the tires. Steering controller 1704 provides input 1728 to steering actuator in the form of an encoded signal, voltage, or other input selected in accordance with steering actuator 1716. Continuing the example, feedback 1732 may indicate steering actuator has applied a force to the steering linkage that resulted in a three degree turn. Accordingly, the actuator feedback will be determined to deviate from the motion control commands (e.g., step 1336 will be determined in the affirmative). Should vehicle path 1108 transgress too close to safe zone 1112, or extend beyond safe zone 1112 (e.g., areas 1404, 1504, and/or 1604, etc.) but feedback signals 1732 indicate the steering operation was correctly executed by steering actuator 1716 (e.g., step 1336 will be determined in the negative), motion control system 1752 is notified of the failure which, as described more completely with respect to FIG. 13, may cause components to switch to a backup, omit or include certain inputs, or other operation to cause vehicle path 1108 to be recalculated and executed by motion control system 1756 and thereby maintain vehicle path 1108 within safe zone 1112.

Any of the steps, functions, and operations discussed herein can be performed continuously and automatically.

The exemplary systems and methods of this disclosure have been described in relation to vehicle systems and electric vehicles. However, to avoid unnecessarily obscuring the present disclosure, the preceding description omits a number of known structures and devices. This omission is not to be construed as a limitation of the scope of the claimed disclosure. Specific details are set forth to provide an understanding of the present disclosure. It should, however, be appreciated that the present disclosure may be practiced in a variety of ways beyond the specific detail set forth herein.

Furthermore, while the exemplary embodiments illustrated herein show the various components of the system collocated, certain components of the system can be located remotely, at distant portions of a distributed network, such as a LAN and/or the Internet, or within a dedicated system. Thus, it should be appreciated, that the components of the system can be combined into one or more devices, such as a server, communication device, or collocated on a particular node of a distributed network, such as an analog and/or digital telecommunications network, a packet-switched network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire, and fiber optics, and may take the form of acoustic or light waves, such as those generated during radio-wave and infra-red data communications.

While the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

In yet another embodiment, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the present disclosure includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as a program embedded on a personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the embodiments with reference to particular standards and protocols, the disclosure is not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various embodiments, configurations, and aspects, includes components, methods, processes, systems and/or apparatus substantially as depicted and described herein, including various embodiments, subcombinations, and subsets thereof. Those of skill in the art will understand how to make and use the systems and methods disclosed herein after understanding the present disclosure. The present disclosure, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease, and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments, configurations, or aspects for the purpose of streamlining the disclosure. The features of the embodiments, configurations, or aspects of the disclosure may be combined in alternate embodiments, configurations, or aspects other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the disclosure.

Moreover, though the description of the disclosure has included description of one or more embodiments, configurations, or aspects and certain variations and modifications, other variations, combinations, and modifications are within the scope of the disclosure, e.g., as may be within the skill and knowledge of those in the art, after understanding the present disclosure. It is intended to obtain rights, which include alternative embodiments, configurations, or aspects to the extent permitted, including alternate, interchangeable and/or equivalent structures, functions, ranges, or steps to those claimed, whether or not such alternate, interchangeable and/or equivalent structures, functions, ranges, or steps are disclosed herein, and without intending to publicly dedicate any patentable subject matter.

Embodiments include an autonomous driving system, comprising: a processor, the processor further comprising circuitry and a memory; a sensor, in communication with the processor; an actuator control, the actuator control receiving a motion control command, converting the motion control command into an actuator command; an actuator, in response to receiving an actuator command, the actuator executes an operation controlling an aspect of locomotion for the vehicle and further provides an actuator feedback signal; a motion control system determining a planned path and providing motion control commands to the actuator to cause the vehicle to traverse the planned path; and wherein the processor, in communication with the actuator control and the motion control system: accesses a safety envelope for the vehicle; receives indicia of an observed path from the vehicle from the sensor; determines the observed path has breached the safety envelope; in response to determining the safety envelope has been breached, determine whether the actuator feedback is divergent from the motion control commands; in response to determining the actuator feedback is divergent from the motion control command, processing a failure in accord with an actuator failure; and wherein processing the failure comprises executing a mitigating action to mitigate the vehicle's breach of the safety envelope.

A method, comprising: accessing a safety envelope for the vehicle; receiving indicia of an observed path of the vehicle; determining the observed path has breached the safety envelope; in response to determining the safety envelope has been breached, determining whether the actuator feedback is divergent from the motion control commands; in response to determining the actuator feedback is divergent from the motion control command, processing a failure in accord with an actuator failure; and in response to determining the actuator feedback is not divergent from the motion control command, processing the failure in accord with a motion control failure; and performing a mitigating action to mitigate the vehicle's breach of the safety envelope.

A system for autonomous driving a vehicle, comprising: a processor, the processor further comprising circuitry and a memory; a sensor, in communication with the processor; an actuator control, the actuator control receiving a motion control command, converting the motion control command into an actuator command; an actuator, in response to receiving an actuator command, the actuator executes an operation controlling an aspect of locomotion for a vehicle and further provides an actuator feedback signal; a motion control system determining a planned path and providing motion control commands to the actuator to cause the vehicle to traverse the planned path; and wherein the processor, in communication with the actuator control and the motion control system: accesses a safety envelope for the vehicle; receives indicia of an observed path from the vehicle from the sensor; determines the observed path has breached the safety envelope; in response to determining the safety envelope has been breached, determine whether the actuator feedback is divergent from the motion control commands; in response to determining the actuator feedback is divergent from the motion control command, processing a failure in accord with an actuator failure; in response to determining the actuator feedback is not divergent from the motion control command, processing the failure in accord with a motion control failure; and wherein processing the failure comprises executing a mitigating action to mitigate the vehicle's breach of the safety envelope.

Aspects of the above vehicle, method, and/or system may include:

Wherein the processor, in response to determining the actuator feedback is not divergent from the motion control command, processing the failure in accord with a motion control failure.

Wherein processing the failure, when in accord with the motion control failure, is further processed by the motion control system to cause the motion control system to execute a motion control failure protocol.

Wherein processing the failure, when in accord with the actuator failure, is further processed by the actuator control to cause the actuator control system to execute an actuator control failure protocol.

Wherein the processor further: accesses a path envelope for the vehicle; receives indicia of an observed path from the vehicle from the sensor; determines the observed path has breached the path envelope; in response to determining the path envelope has been breached, determine whether the actuator feedback is divergent from the motion control commands; in response to determining the actuator feedback is divergent from the motion control command, processing a warning in accord with the actuator failure; and wherein processing the warning comprises executing the mitigating action to mitigate the vehicle's breach of the path envelope.

Wherein the processor, in response to determining the actuator feedback is not divergent from the motion control command, processing the warning in accord with a motion control warning.

Wherein processing the warning, when in accord with the motion control warning, is further processed by the motion control system to cause the motion control system to execute a motion control warning protocol.

Wherein processing the warning, when in accord with the actuator failure, is further processed by the actuator control system to cause the actuator control system to execute an actuator control warning protocol.

Wherein the processor determines the observed path has breached the path envelope, further comprises the processor determining the observed path, absent a corrective action, will breach the safety envelope.

Wherein the processor determines the observed path has breached the safety envelope, further comprises the processor determining the observed path, absent a corrective action, will breach the safety envelope.

Wherein at least one of the path envelope or the safety envelope is dynamically generated by the processor comprising inputs from at least one of stored data comprising static roadway features or sensor data comprising observed roadway features.

Wherein the mitigating action comprises at least one of, alerting an occupant of the vehicle to resume manual control, alerting persons nearby with a visual and/or audible distress signal, applying the brakes, or navigating the vehicle to a portion of the roadway having reduced hazard.

Wherein the mitigating action, when the failure is in accord with the motion control warning, is provided to a motion control system to execute a motion control failure protocol; and the mitigating action, when the failure is in accord with the actuator control warning, is provided to an actuator control system to execute a motion control failure protocol.

Accessing a path envelope for the vehicle; receiving indicia of an observed path from the vehicle from the sensor; determining the observed path has breached the path envelope; in response to determining the path envelope has been breached, determining whether the actuator feedback is divergent from the motion control commands; in response to determining the actuator feedback is divergent from the motion control command, processing a warning in accord with the actuator failure; and in response to determining the actuator feedback is not divergent from the motion control command, processing a warning in accord with the motion control failure; and performing a mitigating action to mitigate the vehicle's breach of the path envelope.

Wherein the mitigating action, when the warning is in accord with the motion control warning, is provided to a motion control system to execute a motion control warning protocol; and the mitigating action, when the warning is in accord with the actuator control warning, is provided to an actuator control system to execute an actuator warning protocol.

Wherein the mitigating action comprises a limit on at least one of the vehicle's speed, rate of speed change, turning, and/or rate of turn.

Wherein the mitigating action comprises at least one of alerting an occupant of the vehicle to resume manual control, alerting persons nearby with a visual and/or audible distress signal, applying the brakes, or navigating the vehicle to a portion of the roadway having reduced hazard.

Wherein the processor accesses a path envelope for the vehicle; receives indicia of an observed path from the vehicle from the sensor; determines the observed path has breached the path envelope; in response to determining the path envelope has been breached, determine whether the actuator feedback is divergent from the motion control commands; in response to determining the actuator feedback is divergent from the motion control command, processing a warning in accord with the actuator failure; and wherein processing the warning comprises executing the mitigating action to mitigate the vehicle's breach of the path envelope.

Any one or more of the aspects/embodiments as substantially disclosed herein.

Any one or more of the aspects/embodiments as substantially disclosed herein optionally in combination with any one or more other aspects/embodiments as substantially disclosed herein.

One or means adapted to perform any one or more of the above aspects/embodiments as substantially disclosed herein.

The phrases "at least one," "one or more," "or," and "and/or" are open-ended expressions that are both conjunctive and disjunctive in operation. For example, each of the expressions "at least one of A, B and C," "at least one of A, B, or C," "one or more of A, B, and C," "one or more of A, B, or C," "A, B, and/or C," and "A, B, or C" means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an embodiment that is entirely hardware, an embodiment that is entirely software (including firmware, resident software, micro-code, etc.) or an embodiment combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

The term "electric vehicle" (EV), also referred to herein as an electric drive vehicle, may use one or more electric motors or traction motors for propulsion. An electric vehicle may be powered through a collector system by electricity from off-vehicle sources, or may be self-contained with a battery or generator to convert fuel to electricity. An electric vehicle generally includes a rechargeable electricity storage system (RESS) (also called Full Electric Vehicles (FEV)). Power storage methods may include: chemical energy stored on the vehicle in on-board batteries (e.g., battery electric vehicle or BEV), on board kinetic energy storage (e.g., flywheels), and/or static energy (e.g., by on-board double-layer capacitors). Batteries, electric double-layer capacitors, and flywheel energy storage may be forms of rechargeable on-board electrical storage.

The term "hybrid electric vehicle" refers to a vehicle that may combine a conventional (usually fossil fuel-powered) powertrain with some form of electric propulsion. Most hybrid electric vehicles combine a conventional internal combustion engine (ICE) propulsion system with an electric propulsion system (hybrid vehicle drivetrain). In parallel hybrids, the ICE and the electric motor are both connected to the mechanical transmission and can simultaneously transmit power to drive the wheels, usually through a conventional transmission. In series hybrids, only the electric motor drives the drivetrain, and a smaller ICE works as a generator to power the electric motor or to recharge the batteries. Power-split hybrids combine series and parallel characteristics. A full hybrid, sometimes also called a strong hybrid, is a vehicle that can run on just the engine, just the batteries, or a combination of both. A mid hybrid is a vehicle that cannot be driven solely on its electric motor, because the electric motor does not have enough power to propel the vehicle on its own.

The term "rechargeable electric vehicle" or "REV" refers to a vehicle with on board rechargeable energy storage, including electric vehicles and hybrid electric vehicles.

What is claimed is:

1. An autonomous driving system, comprising:
a processor;
an actuator control that receives a motion control command and converts the motion control command into an actuator command;
an actuator that, in response to receiving the actuator command, executes an operation controlling an aspect of locomotion for a vehicle and further provides an actuator feedback signal;
a motion control system that determines a path boundary and provides the motion control command to the actuator to cause the vehicle to traverse the path boundary, wherein the path boundary defines an expected location of the vehicle for a particular timeframe; and
a memory comprising a set of instructions that, when executed by the processor, cause the processor to:
access a safe zone boundary for the vehicle, wherein the safe zone boundary defines a dynamic envelope that the vehicle may operate in to avoid an identified object while traversing the path boundary;
recalculate the safe zone boundary upon observing a movement of the identified object;
determine that the path boundary has breached the safe zone boundary as recalculated;
in response to determining that the safe zone boundary has been breached, further determine that the actuator feedback signal is divergent from the motion control command; and in response to determining that the actuator feedback signal is divergent from the motion control command, process a failure in accordance with an actuator failure; and wherein processing the failure comprises executing a mitigating action to mitigate the vehicle's breach or potential breach of the safe zone boundary.

2. The autonomous driving system of claim 1, wherein the processor, in response to determining the actuator feedback signal is not divergent from the motion control command, processing the failure in accordance with a motion control failure.

3. The autonomous driving system of claim 2, wherein processing the failure, in accordance with the motion control failure, is further processed by the motion control system to cause the motion control system to execute the mitigating action.

4. The autonomous driving system of claim 1, wherein processing the failure, in accordance with the actuator failure, is further processed by the actuator control to cause the actuator control to execute the mitigating action.

5. The autonomous driving system of claim 1, further comprising:
- a sensor in communication with the processor; and
- wherein the processor further:
  - receives a current location of the vehicle from the sensor; and
  - wherein the processor determines that the path boundary has breached the safe zone boundary further comprises the processor further determining that the current location of the vehicle has breached the safe zone boundary.

6. The autonomous driving system of claim 5, wherein the processor, in response to determining the actuator feedback signal is not divergent from the motion control command, executing a motion control warning.

7. The autonomous driving system of claim 6, wherein in accordance with the motion control warning, further causes the motion control system to utilize an alternate motion control system or portion thereof.

8. The autonomous driving system of claim 5, wherein processing the mitigating action, in accordance with the actuator failure, is further processed by the actuator control to cause the actuator control to execute an actuator control warning to further limit the vehicle's position within the safe zone boundary.

9. The autonomous driving system of claim 5, wherein the processor determines an observed path has breached the dynamic envelope, further comprises the processor determining that the observed path, absent a corrective action, breaches the safe zone boundary.

10. The autonomous driving system of claim 1, wherein the processor determines an observed path has breached the safe zone boundary, further comprises the processor determining that the observed path, absent a corrective action, breaches the safe zone boundary.

11. The autonomous driving system of claim 1, wherein at least one of the dynamic envelope or the safe zone boundary is dynamically generated by the processor comprising inputs from at least one of stored data comprising static roadway features or sensor data comprising observed roadway features.

12. The autonomous driving system of claim 1, wherein the mitigating action comprises at least one of, alerting an occupant of the vehicle to resume manual control, alerting persons nearby with a visual and/or audible distress signal, applying brakes of the vehicle, or navigating the vehicle to a portion of a roadway having reduced hazard.

13. A method, comprising:
accessing, by a processor, a safe zone boundary, wherein the safe zone boundary defines a dynamic envelope that a vehicle may operate in to avoid identified hazards comprising an identified object while traversing a path boundary, wherein the path boundary defines an expected location of the vehicle for a particular timeframe;

receiving, by the processor, indicia of a current location of the vehicle relative to the safe zone boundary;

recalculating the safe zone boundary upon observing a movement of the identified object;

determining, by the processor, that the current location has breached the safe zone boundary as recalculated;

in response to determining that the safe zone boundary has been breached, further determining, by the processor, that an actuator feedback signal is divergent from a motion control command;

in response to determining that the actuator feedback signal is divergent from the motion control command, processing, by the processor, a failure in accordance with an actuator failure;

in response to determining that the actuator feedback signal is not divergent from the motion control command, processing, by the processor, the failure in accordance with a motion control failure; and performing, by the processor, a mitigating action to mitigate the vehicle's breach or potential breach of the safe zone boundary.

14. The method of claim 13, wherein:
the mitigating action, in accordance with the motion control failure, is provided to a motion control system to execute the mitigating action comprising utilization of an alternate motion control system or portion thereof; and the mitigating action, in accordance with the actuator failure, is provided to an actuator control system to execute the mitigating action to further limit the vehicle's position within the safe zone boundary.

15. The method of claim 13, further comprising:
accessing a current path of the vehicle from a sensor; and
wherein determining that the path boundary has breached the safe zone boundary further comprises determining that the current location of the vehicle has breached the safe zone boundary.

16. The method of claim 15, wherein:
the mitigating action, associated with the motion control failure, further comprises utilization of an alternate motion control system or portion thereof; and the mitigating action, associated with the actuator failure, further comprises applying a distance limit to the vehicle's position within the safe zone boundary.

17. The method of claim 15, wherein the mitigating action comprises a limit on at least one of the vehicle's speed, rate of speed change, turning, and/or rate of turn.

18. The method of claim 13, wherein the mitigating action comprises at least one of alerting an occupant of the vehicle to resume manual control, alerting persons nearby with a visual and/or audible distress signal, applying brakes of the vehicke, or navigating the vehicle to a portion of a roadway having reduced hazard.

19. A system for autonomously driving a vehicle, comprising:
a processor comprising circuitry and a memory;

an actuator control configured to receive a motion control command and convert the motion control command into an actuator command;

an actuator configured, in response to receiving the actuator command, to execute an operation controlling an aspect of locomotion for a vehicle and further provide an actuator feedback signal;

a motion control system programmed to determine a path boundary and provide the motion control command to the actuator to cause the vehicle to traverse the path boundary, wherein the path boundary defines an expected location of the vehicle for a particular timeframe; and wherein the processor, in communication with the actuator control and the motion control system, is programmed to:

access a safe zone boundary for the vehicle wherein the safe zone boundary defines a dynamic envelope that the vehicle may operate in to avoid identified hazards while traversing the path boundary;

recalculate the safe zone boundary upon observing a movement of an identified object, wherein the identified object is one of the identified hazards;

determine that the path boundary has breached the safe zone boundary as recalculated;

in response to determining that the safe zone boundary has been breached, further determine that the actuator feedback signal is divergent from the motion control command;

in response to determining that the actuator feedback signal is divergent from the motion control command, process a failure in accordance with an actuator failure; and in response to determining that the actuator feedback signal is not divergent from the motion control command, process the failure in accordance with a motion control failure; and wherein processing the failure comprises executing a mitigating action to mitigate the vehicle's breach of the safe zone boundary.

20. The system for autonomously driving the vehicle of claim 19, further comprising:

a sensor in communication with the processor; and wherein the processor:

accesses a current location of the vehicle from a sensor; and wherein the processor determining that the path boundary has breached the safe zone boundary further comprises the processor determining that the current location of the vehicle has breached the safe zone boundary.

* * * * *